United States Patent
Robertson et al.

(10) Patent No.: US 11,963,973 B2
(45) Date of Patent: Apr. 23, 2024

(54) DEOXY-CYTIDINE OR URIDINE DERIVATIVES FOR USE IN CANCER THERAPIES

(71) Applicant: HEMISPHERIAN AS, Oslo (NO)

(72) Inventors: Adam Brian Robertson, Oslo (NO); Terezia Prikrylova, Zilina (SK)

(73) Assignee: HEMISPHERIAN AS, Oslo (NO)

( * ) Notice: Subject to any disclaimer, the term of this patent is extended or adjusted under 35 U.S.C. 154(b) by 0 days.

(21) Appl. No.: 17/427,542

(22) PCT Filed: Feb. 3, 2020

(86) PCT No.: PCT/EP2020/052632
§ 371 (c)(1),
(2) Date: Jul. 30, 2021

(87) PCT Pub. No.: WO2020/157335
PCT Pub. Date: Aug. 6, 2020

(65) Prior Publication Data
US 2022/0117992 A1    Apr. 21, 2022

(30) Foreign Application Priority Data
Feb. 1, 2019 (GB) ................................ 1901427

(51) Int. Cl.
| | | |
|---|---|---|
| A01N 43/04 | (2006.01) |
| A61K 31/17 | (2006.01) |
| A61K 31/495 | (2006.01) |
| A61K 31/513 | (2006.01) |
| A61K 31/70 | (2006.01) |
| A61K 31/7068 | (2006.01) |
| A61K 31/7072 | (2006.01) |
| A61P 35/00 | (2006.01) |
| C07H 19/06 | (2006.01) |
| C07H 19/10 | (2006.01) |

(52) U.S. Cl.
CPC .......... *A61K 31/7072* (2013.01); *A61K 31/17* (2013.01); *A61K 31/495* (2013.01); *A61K 31/513* (2013.01); *A61K 31/7068* (2013.01); *A61P 35/00* (2018.01); *C07H 19/06* (2013.01); *C07H 19/10* (2013.01)

(58) Field of Classification Search
None
See application file for complete search history.

(56) References Cited

U.S. PATENT DOCUMENTS

| | | |
|---|---|---|
| 4,148,889 A | 4/1979 | Gupta |
| 2010/0266565 A1 | 10/2010 | Matsumoto |
| 2011/0230433 A1 | 9/2011 | Loeb et al. |
| 2015/0142867 A1 | 5/2015 | Oplinger et al. |
| 2016/0101188 A1 | 4/2016 | Litosh et al. |
| 2018/0125875 A1 | 5/2018 | Matsumoto et al. |

FOREIGN PATENT DOCUMENTS

| | | |
|---|---|---|
| CN | 1205640 A | 1/1999 |
| CN | 102125579 A | 7/2011 |
| CN | 104592333 A | 5/2015 |
| DE | 114949 C | 9/1975 |
| DE | 102014113936 A | 3/2016 |
| EA | 026341 B1 | 3/2017 |
| WO | 95/27493 A1 | 10/1995 |
| WO | 96/26743 A1 | 9/1996 |
| WO | 97/23230 A1 | 7/1997 |
| WO | 00/51639 A2 | 9/2000 |
| WO | 01/14345 A1 | 3/2001 |
| WO | 2008085611 A2 | 7/2008 |
| WO | 2010115847 A1 | 10/2010 |
| WO | 2011106997 A1 | 9/2011 |

(Continued)

OTHER PUBLICATIONS

PCT International Search Report and Written Opinion dated Apr. 30, 2020, PCT International Application No. PCT/EP2020/052632, pp. 1-19.
Kyung Noo Kim et al., "A new synthetic analogue of thymidine, 7-(3-bromo-phenoxy)-thymidine, inhibits the proliferation of tumor cells," Bioorganic & Medicinal Chemistry Letters, vol. 15, 2005, pp. 77-79.
Melania Zauri et al., "CDA directs metabolism of epigenetic nucleosides revealing a therapeutic window in cancer," Nature, vol. 524, No. 7563, Aug. 2015, pp. 114-118.
J. Balzarini et al., "Role of Thymidine Kinase in the Inhibitory Activity of 5-Substituted-2'-Deoxyuridines on the Growth of Human and Murine Tumor Cell Lines," Biochemical Pharmacology, vol. 31, No. 6, 1982, pp. 1089-1095.

(Continued)

*Primary Examiner* — Patrick T Lewis
(74) *Attorney, Agent, or Firm* — Siepmann IP, PLLC

(57) ABSTRACT

The present invention relates to a compound of Formula (I), or a stereoisomer, solvate, tautomer or pharmaceutically acceptable salt thereof, wherein X, $W_1$, $W_2$, Y, Z, $R_1$, $R_2$ and $R_3$ are as defined in the disclosure herein, for use in therapy, particularly for use in the treatment of cancer. The present invention also relates to methods of treating cancer comprising the administration of a compound of Formula (I) to a subject in need thereof, and to pharmaceutical compositions and kits comprising such compounds.

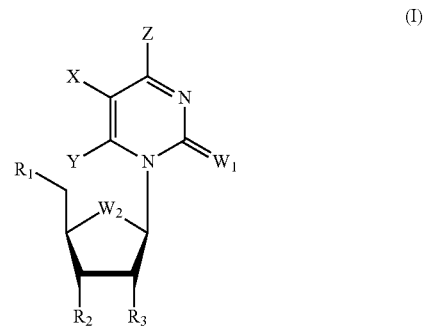

16 Claims, 20 Drawing Sheets

(56) References Cited

FOREIGN PATENT DOCUMENTS

| WO | 2011123645 A2 | 10/2011 |
|---|---|---|
| WO | 2012023572 A1 | 2/2012 |
| WO | 2012062907 A1 | 5/2012 |
| WO | 2013052523 A1 | 4/2013 |
| WO | 2014/194250 A2 | 12/2014 |
| WO | 2015/142867 A1 | 9/2015 |
| WO | 2016029889 A1 | 3/2016 |
| WO | 2017/178586 A1 | 10/2017 |
| WO | 2018085156 A1 | 5/2018 |
| WO | 2021048235 A1 | 3/2021 |

OTHER PUBLICATIONS

J. Balzarini et al., "Structure-Function Relationship of the Antitumor Cell Activity of Pyrimidine and Pyridine Derivatives," Proceedings of the 4th International Round Table Nucleosides, Nucleotides and Their Biological Applications, vol. 4, Feb. 1981, pp. 275-291.

Kayla M. Borland et al., "Base-modified thymidines capable of terminating DNA synthesis are novel bioactive compounds with activity in cancer cells," Bioorganic & Medicinal Chemistry, vol. 23, No. 8, 2015, pp. 1869-1881.

Walter+Eliza Hall Bioinformatics Institute of Medicinal Research, "LIMMA: Linear Models for Microarray and RNA-seq Data," Retrieved from the Internet on Jun. 30, 2021: http://bioinf.wehi.edu.au/limma/, pp. 1-2.

Rafael A. Irizarry et al., "Exploration, normalization, and summaries of high density oligonucleotide array probe level data," Biostatistics, vol. 4, No. 2, 2003, pp. 249-264.

Expression Atlas: Gene expression across species and biological conditions, Retrieved from the Internet Jun. 30, 2021: https://www.ebi.ac.uk/gxa/home, pp. 1-5.

Genvestigator: shaping biological discovery, Retrieved from Internet on Jun. 30, 2021: https://genevestigator.com/, pp. 1-6.

Cancer Cell Line Encyclopedia (CCLE), Retrieved from the Internet on Jun. 30, 2021: https://sites.broadinstitute.org/ccle, pp. 1-10.

The Human Protein Atlas, Retrieved from the Internet on Jun. 30, 2021: https://www.proteinatlas.org/, pp. 1-2.

Anroop B. Nair et al., "A simple practice guide for dose conversion between animals and human," Journal of Basic and Clinical Pharmacy, vol. 7, Issue 2, Mar.-May 2016, pp. 27-31.

Jordi Barretina et al., "The Cancer Cell Line Encyclopedia enables predictive modeling of anticancer drug sensativity," Nature, vol. 483, No. 7391, Mar. 2012, pp. 603-607.

Benjamin C. Creelan, "Update on Immune Checkpoint Inhibitors in Lung Cancer," Cancer Control, vol. 21, No. 1, 2014, pp. 80-89.

Gunter P. Wagner et al., "Measurement of mRNA abundance using RNA-seq data: RPKM measure is inconsistent among samples," Theory in Biosciences, vol. 131, No. 4, 2012, pp. 281-285.

Ali Mortazavi et al., "Mapping and quantifying mammalian transcriptomes by RNA-Seq," Nature Methods, vol. 5, No. 7, Jul. 2008, pp. 621-628.

Cole Trapnell et al., "Transcript assembly and abundance estimation from RNA-Seq reveals thousands of new transcripts and switching among isoforms," Nature Biotechnology, vol. 28, No. 5, 2010, pp. 511-515.

Sheldon Greer et al., "Five-chlorodeoxycytidine, a tumor-selective enzyme-driven radiosensitizer, effectively controls five advanced human tumors in nude mice." International Journal of Radiation Oncology* Biology* Physics 51.3 (2001): 791-806.

Martin De Kort et al., "Synthesis of Oligodeoxynucleotides Containing 5-(β-D-Glucopyranosyloxymethyl)-2'-deoxyuridine, a Modified Nucleoside in the DNA of Trypanosoma Brucei," European journal of organic chemistry 1999.9 (1999): 2337-2344.

Martin Munzel et al., "Quantification of the Sixth DNA Base Hydroxymethylcytosine in the Brain," Angewandte Chemie International Edition 49.31 (2010): 5375-5377.

Notice of Reasons for Rejection dated Oct. 17, 2022, Japanese Application No. 2021-544852, pp. 1-6. (English Translation of Document Provided).

A

B

** Animal did not survive       * No tumor mass detected

H

◆ X=CHO, Y=H, Z=OH
■ X=CHO, Y=H, Z=H
▲ X=Cl, Y=H, Z=H 5-methoxymethyl-2'-deoxyuridine 5-acetoxymethyl-2'-deoxyuridine

DEOXY-CYTIDINE OR URIDINE DERIVATIVES FOR USE IN CANCER THERAPIES

CROSS-REFERENCE TO RELATED APPLICATIONS

This application is a U.S. National Stage Application of PCT/EP2020/052632, filed on Feb. 3, 2020, which claims the benefit of GB 1901427.3, filed on Feb. 1, 2019, each of which is herein incorporated by reference in its entirety.

The present invention relates to compounds for use in therapy, particularly in the treatment or prevention of cancer. The invention also relates to pharmaceutical formulations comprising such compounds and to the use of such pharmaceutical formulations in therapy, particularly in the treatment or prevention of cancer. This invention also relates to such compounds for combined treatment with known anticancer agents. Thus, the invention relates to the use in cancer treatment or prevention of the compounds of the invention both alone, and in combination with one or more additional or further anticancer agents. The invention also relates to methods of treating or preventing cancer using the compounds of the invention, either alone or in combination with one or more further anticancer agents.

Cancer is a disease characterized by the loss of appropriate control of cell growth and proliferation. The American Cancer Society has estimated that there were in excess of 1.5 million new cases of cancer within the United States of America in 2010 and approximately 570,000 deaths that year estimated to be attributable to cancer. The World Health Organization has estimated that cancer was the leading cause of death globally in 2010, with the number of deaths caused by cancer growing to 12 million per year by 2030.

Whilst there are numerous therapies available, resistance to known anticancer drugs can be a problem in the successful treatment of cancer in patients. There remains a need for additional cancer therapies.

In some contexts, anticancer agents capable of killing a wide range of cancer cell types are desirable. Fluorouracil (5-FU) is one such anticancer agent, routinely administered for the treatment of a wide range of cancers.

However, many anticancer agents which are capable of killing a wide range of cancer cell types also kill non-cancerous cells, for instance normal, healthy cells which are dividing. This is problematic in some contexts, so there is also a need for broadly cytotoxic anticancer agents which are not cytotoxic against non-cancerous cells. Additionally, there is a need for anticancer agents with more specific cytotoxicity, i.e. which kill a smaller range of cancer cell types. Such more specific anticancer agents are less likely to have undesirable off-target effects.

Glioblastoma multiforme is the most common and aggressive cancer of the central nervous system. Glioblastoma multiforme is the second most common cancer in children. Adults diagnosed with glioblastoma multiforme have some of the highest unmet needs in oncology. With currently available treatments, mean survival from diagnosis is 14.6 months. Less than 5% of patients diagnosed with glioblastoma multiforme survive longer than 5 years. Long-term survival after glioblastoma multiforme diagnosis is rare and is more common in children.

Present therapies are largely palliative and designed to improve quality of life. After diagnosis, current glioblastoma multiforme treatment follows a similar course: surgical resection of the affected brain area, where the patient is expected to survive the surgery, followed by radiation and chemotherapies. Glioblastoma multiforme forms tentacle like structures in the afflicted brain; therefore, even where indicated complete surgical resection is challenging and often impossible. Aside from surgical intervention and radiation therapy, three drugs are approved for glioblastoma multiforme treatment:

1) Avastin® (bevacizumab)—an angiogenesis inhibitor with multiple oncology indications. Avastin® is thought to inhibit tumour growth by inhibiting the development of new blood vessels within tumours, effectively starving the tumour. Avastin® is approved in the USA and in Japan; however, Avastin® is not approved for GBM treatment in the EU. Indeed, Phase II trials indicated that Avastin® did not yield an overall survival benefit (NCI 06-C-0064E). While Avastin® slightly improves progression free survival in some trials, the patient benefit is often nominal and there is no benefit afforded by Avastin® treatment in recurrent glioblastoma multiforme patients.

2) Temozolomide (Temodal®/Temodar®)(4-methyl-5-oxo-2,3,4,6,8-pentazabicyclo[4.3.0]nona-2,7,9-triene-9-carboxamide)—a mutagenic DNA alkylating agent; generic formulations are also available. Temozolomide is believed to inhibit glioblastoma multiforme growth by severely mutating tumour DNA inducing cell death. Due to the mechanism of action, cells that express the DNA repair protein MGMT are almost universally resistant to temozolomide treatment. Temozolomide treatment improves overall survival by 2.5 months. At the same time, temozolomide treatment often causes significant side-effects. Temozolomide is the primary treatment for glioblastoma multiforme.

3) Gliadel® (Carmustine wafer)(1,3-Bis(2-chloroethyl)-1-nitrosourea)—a cytotoxic nitrogen mustard. It is delivered as a biodegradable disc implanted directly into the brain after surgical resection. A randomized trial demonstrated that Gliadel® improves median survival by 2.1 months. Patients treated with Gliadel® report fewer and less severe side-effects than temozolomide treated patients; however, compared to temozolomide overall survival is reduced.

There remains a need for further anticancer agents for the treatment of glioblastoma multiforme and other cancers. In particular there remains a need for anticancer agents which effectively treat cancers which are resistant to treatment with Temozolomide.

The human protein cytidine deaminase (CDA) catalyses hydrolytic deamination of cytidine and deoxycytidine into uridine and deoxyuridine, respectively. Some known anticancer agents are nucleoside/nucleotide analogs, for instance gemcitabine (2,2-difluorodeoxycytidine) and cytarabine (Ara-C, cytosine arabinoside). CDA problematically inactivates such anticancer agents, including gemcitabine and cytarabine. There remains a need for further anticancer agents which are not inactivated by CDA.

The present inventors have found a selected class of compounds which exhibit an activity in treating glioblastoma multiforme and a wide range of other cancers. Such compounds are suitable for inhibiting the proliferation of tumour cells in general and, in particular, those associated with cancers of the brain, particularly glioblastoma multiforme.

In a first aspect, the invention provides a compound of Formula (I):

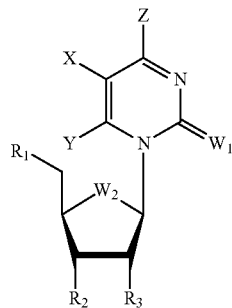

Formula (I)

or a stereoisomer, solvate, tautomer or pharmaceutically acceptable salt thereof for use in therapy;
wherein:
X is a group containing from 1 to 20 non-hydrogen atoms, which contains at least one functional group selected from an aldehyde, an alcohol, a protected alcohol, an ether, an ester and a carboxylic acid, with the proviso that X is not —COOH;
$W_1$ and $W_2$ are each independently O, S or NH;
Y is H or a group containing from 1 to 15 non-hydrogen atoms;
Z is —OPG, —OR, or —N($R_x R_y$), where $R_x$, $R_y$ and $R_z$ are independently H or a group containing from 1 to 10 non-hydrogen atoms;
$R_1$ is H or a group containing from 1 to 15 non-hydrogen atoms;
$R_2$ is H, —OH, —OPG, —F, —Cl, —Br, —I, or —$N_3$; and
$R_3$ is H, —F, —Cl, —Br, —I, or —$N_3$;
where PG is an alcohol protecting group, such as acetyl (Ac), benzyl (Bn) or benzoyl (Bz).

The compounds of the invention are particularly for use in the treatment or prevention of cancer. Thus, in a further aspect the present invention provides a compound of Formula (I):

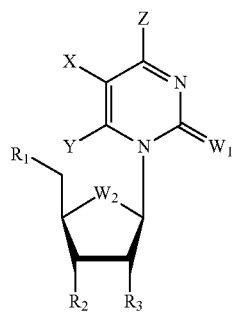

Formula (I)

or a stereoisomer, solvate, tautomer or pharmaceutically acceptable salt thereof for use in the treatment or prevention of cancer;
wherein:
X is a group containing from 1 to 20 non-hydrogen atoms, which contains at least one functional group selected from an aldehyde, an alcohol, a protected alcohol, an ether, an ester and a carboxylic acid, with the proviso that X is not —COOH;
$W_1$ and $W_2$ are each independently O, S or NH;
Y is H or a group containing from 1 to 15 non-hydrogen atoms;
Z is —OPG, —OR, or —N($R_x R_y$), where $R_x$, $R_y$ and $R_z$ are independently H or a group containing from 1 to 10 non-hydrogen atoms;
$R_1$ is H or a group containing from 1 to 15 non-hydrogen atoms;
$R_2$ is H, —OH, —OPG, —F, —Cl, —Br, —I, or —$N_3$; and
$R_3$ is H, —F, —Cl, —Br, —I, or —$N_3$;
where PG is an alcohol protecting group, such as acetyl (Ac), benzyl (Bn) or benzoyl (Bz).

The present invention is applicable to any cancer. Cancer is defined broadly herein to include any neoplastic condition, and includes particularly malignant or pre-malignant conditions. The cancer may cause or result in or manifest in solid tumours, but is not limited to such, and includes also cancers of the haempoietic system. Throughout, the terms "cancer" and "cancer cells" are used interchangeably. Throughout, the terms "tumour" and "tumour cells" are used interchangeably. Benign tumours and malignant tumours are also included in the term cancer as used herein, i.e. the terms cancer and tumour are used interchangeably. The treatment of malignant tumours is preferred.

Thus, alternatively viewed, the present invention provides a compound of Formula (I) for use in the treatment or prevention of a tumour.

Alternatively viewed, the present invention provides a compound of Formula (I) for use as an anticancer agent. Alternatively viewed, the present invention provides the use of a compound of Formula (I) for treating or preventing cancer.

Alternatively viewed, the present invention provides a compound of Formula (I) for use as an anti-tumour agent. Alternatively viewed, the present invention provides the use of a compound of Formula (I) for treating or preventing a tumour.

Alternatively viewed, this aspect of the present invention provides use of a compound of Formula (I) in the manufacture of an anticancer therapeutic product (i.e. a preparation or medicament, for example a pharmaceutical composition, formulation, combined product, co-formulated product, or kit), or alternatively put, for the manufacture of a medicament for use as an anticancer agent or in the treatment or prevention of cancer.

Alternatively viewed, this aspect of the present invention provides use of a compound of Formula (I) in the manufacture of an anti-tumour therapeutic product (i.e. a preparation or medicament, for example a pharmaceutical composition, formulation, combined product, co-formulated product, or kit), or alternatively put, for the manufacture of a medicament for use as an anti-tumour agent or in the treatment or prevention of a tumour.

In a further aspect, the present invention also provides a method of treating or preventing cancer in a subject which method comprises administering a compound of Formula (I) to said subject.

In a further aspect, the present invention also provides a method of treating or preventing a tumour in a subject which method comprises administering a compound of Formula (I) to said subject.

In some preferred embodiments of the present invention the compound of Formula (I) is used as the sole active agent (sole active agent in the treatment regimen). Thus, in some preferred embodiments the treatment is a monotherapy. Monotherapy refers to the use of a single drug to treat a disease or condition, in this cancer (i.e. a tumour). Thus, in some preferred embodiments the compound of Formula (I) is used alone. By "sole active agent" (or sole active ingredient) is meant the sole agent or ingredient that is therapeutically active (or biologically active). Thus, components such as preservatives or excipients or agents that are not relevant to the disease being treated are not considered to be active agents.

In the treatment or prevention of cancer (i.e. a tumour) the compound of Formula (I) may be used alone or optionally in combination with a further, i.e. one or more other, anticancer agent(s) (i.e. an additional or second anticancer agent(s)).

The compound of Formula (I), either alone or in combination with a further anticancer agent, may be used according to the present invention in any method of treatment or prevention of cancer (i.e. of a tumour) in a subject.

As demonstrated in the Examples, the use of a compound of Formula (I) in combination with one or more further anticancer agents results in synergistic cytotoxic effects.

Accordingly, in a further aspect, the present invention provides a compound of Formula (I) together with a further anticancer agent for use in treating or preventing cancer(i.e. a tumour), or alternatively put, a compound of Formula (I) for use together with a further anticancer agent for treating or preventing cancer (i.e. a tumour).

Alternatively viewed, this aspect of the present invention provides use of a compound of Formula (I) in the manufacture of an anticancer (i.e. anti-tumour) therapeutic product (i.e. a preparation or medicament, for example a pharmaceutical composition, formulation, combined product or kit), or alternatively put, for the manufacture of a medicament for use as an anticancer agent (i.e. anti-tumour agent) or in the treatment or prevention of cancer (i.e of a tumour), wherein said treatment further comprises the administration of a further anticancer agent.

In a further aspect, the present invention also provides a method of treating or preventing cancer (i.e a tumour) in a subject, which method comprises administering a compound of Formula (I), optionally together with a further (i.e. second) anticancer agent, to said subject. Particularly, in this aspect the method comprises administering an effective amount of said compound of Formula (I) and the optional further anticancer agent.

The compound of Formula (I) and the further anticancer agent(s) may be co-formulated into a single composition. However, this is not necessary. The medicament may be a combined preparation, composition or kit etc. and it is not necessary in any of the aspects of the invention for the compound of Formula (I) and the further anticancer agent(s) to be co-formulated in a single composition—they may be separately formulated and may be administered separately, including sequentially or simultaneously.

Accordingly, the invention also provides a kit comprising a compound of Formula (1) and a further (i.e. one or more further or second) anticancer agent(s) for using in the treatment or prevention of cancer (i.e. of a tumour).

More particularly, the invention provides a product (particularly a pharmaceutical product) comprising a compound of Formula (I) and a further (i.e. one or more further or second) anticancer agent(s) as a combined preparation for separate, sequential or simultaneous use in the treatment or prevention of cancer. (i.e. of a tumour).

Additionally, the present invention provides a product (particularly a pharmaceutical product) comprising a compound of Formula (I) co-formulated with a further (i.e. one or more further or second) anticancer agent(s).

The present invention provides a pharmaceutical composition comprising a compound of Formula (I) and one or more pharmaceutically acceptable excipients, optionally further comprising a further anticancer agent.

In relation to all aspects of the invention, the compound of the invention is the compound of Formula (I) as described elsewhere herein, and the preferred and optional embodiments concerning the compound described in relation to one aspect of the invention apply mutatis mutandis to each and every other aspect of the invention.

In all aspects and embodiments of the invention, the treatment of malignant tumours is preferred.

X

X is a group containing from 1 to 20 non-hydrogen atoms, which contains at least one functional group selected from an aldehyde, an alcohol, a protected alcohol, an ether, an ester and a carboxylic acid, with the proviso that X is not —COOH.

Preferably, X is a group containing from 1 to 10 non-hydrogen atoms, more preferably from 1 to 5 non-hydrogen atoms, even more preferably from 1 to 3 non-hydrogen atoms, and most preferably 2 non-hydrogen atoms.

More preferably, X is a group containing at least 2 non-hydrogen atoms, i.e. a group containing from 2 to 20 non-hydrogen atoms. Thus, preferably X is a group containing from 2 to 10 non-hydrogen atoms, even more preferably from 2 to 5 non-hydrogen atoms, even more preferably from 2 to 3 non-hydrogen atoms, and most preferably 2 non-hydrogen atoms.

Preferably, X contains at least one functional group selected from an aldehyde, an alcohol, a protected alcohol, an ether and an ester. More preferably, X contains at least one functional group selected from an aldehyde, an alcohol, an ether and an ester. Most preferably, X contains at least one functional group selected from an aldehyde and an alcohol. For example X preferably contains an aldehyde functional group. For example X preferably contains an alcohol functional group.

Preferably, X contains just one functional group.

Preferably, X is a group as defined herein, with the proviso that X is not —COOH or —OH.

X may be defined as -L-X', wherein:

L is a bond, alkyl, alkenyl, alkynyl, haloalkyl, alkoxy, haloalkoxy; and

X' is —CHO, —OH, —OPG, —COOH, —OR, —OC(=O)R or —C(=O)OR, wherein PG is an alcohol protecting group, such as acetyl (Ac), benzyl (Bn) or benzoyl (Bz), and wherein R is an alkyl group, preferably methyl.

The term "alkyl" refers to straight and branched saturated aliphatic hydrocarbon chains. Preferably, alkyl refers to $C_{1-10}$ alkyl. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

R may be any alkyl group, such those exemplified above. For example, R may be —$(CH_2)_n$H, where n is from 1 to 10, preferably from 1 to 5, more preferably from 1 to 3, and most preferably 1. When n is 1, R is $CH_3$.

The term "alkenyl" refers to straight and branched hydrocarbon chains having one or more, preferably one or two, carbon-carbon double bonds. Preferably, alkenyl refers to $C_{2-10}$ alkenyl. Examples of alkenyl groups include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

The term "alkynyl" refers to straight and branched hydrocarbon chains having one or more, preferably one or two, carbon-carbon triple bonds. Preferably, alkynyl refers to $C_{2-10}$ alkynyl. Examples of alkynyl groups include, but are not limited to, ethynyl, propynyl, and propargyl.

The term "haloalkyl" refers to straight and branched saturated aliphatic hydrocarbon chains substituted with 1 or more halogens (fluoro (F), chloro (Cl), bromo (Br), and iodo (I)). Preferably, haloalkyl refers to $C_{1-10}$ haloalkyl. Examples of haloalkyl groups include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl.

The term "alkoxy" refers to an —O-alkyl group. Preferably, alkoxy refers to $C_{1-10}$ alkoxy. Example alkoxy groups include, but are not limited to, methoxy, ethoxy, propoxy (e.g., n-propoxy and isopropoxy), and t-butoxy.

The term "haloalkoxy" refers to a haloalkyl group as defined above attached through an oxygen bridge. Preferably, haloalkoxy refers to $C_{1-10}$ haloalkoxy.

Examples of haloalkoxy groups include, but are not limited to, trifluoromethoxy, 2,2,2-trifluoroethoxy, and pentafluorothoxy.

When X is -L-X', the X group must still contain the required number of non-hydrogen atoms.

Preferably, L is a bond, alkyl, alkenyl or alkynyl, more preferably a bond or alkyl. For example, L may be a bond or $C_{1-6}$ alkyl. More preferably, L is a bond or $C_{1-4}$ alkyl. Most preferably, L is a bond or $C_1$ alkyl (—$CH_2$—).

X' is preferably —CHO, —OH, —OPG, —OR, —OC(=O)R or —C(=O)OR, more preferably —CHO, —OH, —OR, —OC(=O)R or —C(=O)OR, most preferably —CHO, —OH, —OR or —OC(=O)R.

Thus, preferably X is —$(CH_2)_n$—X', wherein n is from 0 to 6, preferably from 0 to 4 and more preferably 0 or 1, and X is as defined above, preferably —CHO, —OH, —OR or —OC(=O)R, where R is as defined above.

Preferably X is —$(CH_2)_n$—X', wherein n is from 0 to 6 and X is —OH or —CHO. Preferably X is —$(CH_2)_n$—X', wherein n is from 0 to 6 and X' is —OH. Preferably X is —$(CH_2)_n$—X', wherein n is from 0 to 6 and X is —CHO.

More preferably X is —$(CH_2)_n$—X', wherein n is from 0 to 4 and X is —OH or —CHO. Preferably X is —$(CH_2)_n$—X', wherein n is from 0 to 4 and X' is —OH. Preferably X is —$(CH_2)_n$—X', wherein n is from 0 to 4 and X is —CHO.

More preferably X is —$(CH_2)_n$—X', wherein n is from 0 to 2 and X is —OH or —CHO. Preferably X is —$(CH_2)_n$—X', wherein n is from 0 to 2 and X' is —OH. Preferably X is —$(CH_2)_n$—X', wherein n is from 0 to 2 and X is —CHO.

More preferably X is —$(CH_2)_n$—X', wherein n is 0 or 1 and X is —OH or —CHO. Preferably X is —$(CH_2)_n$—X', wherein n is 0 or 1 and X' is —OH. Preferably X is —$(CH_2)_n$—X', wherein n is 0 or 1 and X is —CHO.

More preferably, X is —CHO, —$CH_2OH$, —$CH_2OCH_3$ or —$CH_2OC(=O)CH_3$.

More preferably, X is a) —CHO or —$CH_2OH$; or b) —$CH_2OCH_3$ or —$CH_2OC(=O)CH_3$.

More preferably X is —CHO or —$CH_2OH$, most preferably $CH_2OH$.

In all of the above definitions of X, it is preferred that X is not —OH. Thus, when X' is —OH, it is preferred that L is not a bond (i.e. n is not 0). In this case, n may be from 1 to 6, preferably from 1 to 4, more preferably from 1 to 2, and most preferably 1.

$W_1$ and $W_2$ $W_1$ and $W_2$ are each independently O, S or NH, preferably O or S, more preferably O.

Thus, preferably $W_1$ is O or S and $W_2$ is O, S or NH; or $W_2$ is O or S and $W_1$ is O, S or NH.

More preferably, $W_1$ and $W_2$ are both O or S, and even more preferably $W_1$ is O and $W_2$ is O or S; or $W_2$ is O, and $W_1$ is O or S.

Most preferably, $W_1$ and $W_2$ are both O.

Y

Y is H or a group containing from 1 to 15 non-hydrogen atoms. Preferably, Y is H or a group containing from 1 to 10 non-hydrogen atoms. More preferably, Y is H or a group containing from 1 to 5 non-hydrogen atoms.

For example, Y may be H, —OH, —OPG, —F, —Cl, —Br, —I, or —$N_3$, where PG is an alcohol protecting group, such as acetyl, benzyl or benzoyl.

When Y is H or a group containing from 1 to 5 non-hydrogen atoms, Y may be H, —OH, —OAc, —F, —Cl, —Br, —I, or —$N_3$.

Most preferably, Y is H.

Z

Z is —OPG, —OR, or —$N(R_xR_y)$, where Rx, $R_y$ and $R_z$ are independently H or a group containing from 1 to 10 non-hydrogen atoms, and where PG is an alcohol protecting group, such as acetyl, benzyl or benzoyl.

Preferably, Z is —$OR_z$ or —$N(R_xR_y)$.

Preferably, $R_z$ is H or a group containing from 1 to 5 non-hydrogen atoms, more preferably H or a group containing from 1 to 3 non-hydrogen atoms, and most preferably H.

Preferably, $R_x$ and $R_y$ are independently H or a $C_{1-8}$ ester. More preferably, RX and $R_y$ are independently H or —C(O)O$(CH_2)_nCH_3$, where n is from 1 to 4, preferably 4.

Preferably, at least one of $R_x$ and $R_y$ are H. For example, preferably $R_x$ is H and $R_y$ is independently H or —C(O)O$(CH_2)_nCH_3$, where n is from 1 to 4, preferably 4. More preferably, $R_x$ and $R_y$ are both H.

Z is therefore preferably —$NH_2$ or —OH. More preferably, Z is —$NH_2$ when X is —CHO or —$CH_2OH$, most preferably —$CH_2OH$; and Z is —OH when X is —$CH_2OCH_3$ or —$CH_2OC(=O)CH_3$.

When Z is —OH, the compound of formula (I) can be drawn in a tautomeric form, as shown below:

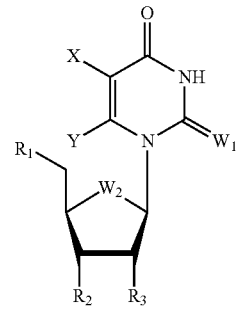

A tautomeric form of Formula (I), when Z is —OH

Alternatively, Z is preferably —OPG, —$OR_z$ or —$N(R_xR_y)$, where PG, $R_x$ and $R_y$ are as defined above, and where $R_z$ is a group containing from 1 to 10 non-hydrogen atoms.

In this case, $R_z$ is preferably a group containing from 1 to 5 non-hydrogen atoms, more preferably a group containing from 1 to 3 non-hydrogen atoms.

In this case, Z is preferably —OPG or —$N(R_xR_y)$, wherein PG, $R_x$ and $R_y$ are as defined above.

Most preferably, Z is —N($R_x R_y$), wherein $R_x$ and $R_y$ are as defined above.

Z is therefore preferably —$NH_2$.

$R_1$ $R_1$ is H or a group containing from 1 to 15 non-hydrogen atoms, preferably H or a group containing from 1 to 13 non-hydrogen atoms.

Preferably, $R_1$ is H, —OH, —OPG, —F, —Cl, —Br, —I, —$N_3$, or —O(P(=O)(OH)O)$_n$H, where n is from 1 to 3, and where PG is an alcohol protecting group, such as acetyl, benzyl or benzoyl.

Preferably, $R_1$ is H, —OH, —F, —Cl, —Br, —I, —$N_3$, or —O(P(=O)(OH)O)$_n$H, where n is from 1 to 3, preferably 3. More preferably, $R_1$ is H, —OH or —O(P(=O)(OH)O)$_n$H, where n is from 1 to 3, preferably 3. Even more preferably, $R_1$ is —OH or —O(P(=O)(OH)O)$_n$H, where n is from 1 to 3, preferably 3. Most preferably $R_1$ is —OH.

$R_2$ $R_2$ is H, —OH, —OPG, —F, —Cl, —Br, —I, or —$N_3$, where PG is an alcohol protecting group, such as acetyl, benzyl or benzoyl.

Preferably, $R_2$ is H, —OH, —F, —Cl, —Br, —I, or —$N_3$. More preferably, $R_2$ is H or —OH, and most preferably $R_2$ is —OH.

$R_3$ $R_3$ is H, —F, —Cl, —Br, —I, or —$N_3$, preferably H.

Most preferably, $R_1$ is —OH or —O(P(=O)(OH)O)$_n$H where n is from 1 to 3, preferably 3; $R_2$ is —OH; and $R_3$ is H.

PREFERRED EMBODIMENTS

Preferably, the compound of Formula (I) is a compound of Formula (IIa) or Formula (IIb), or a stereoisomer, solvate, tautomer or pharmaceutically acceptable salt thereof:

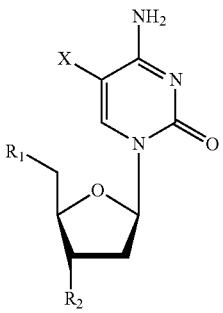

Formula (IIa)

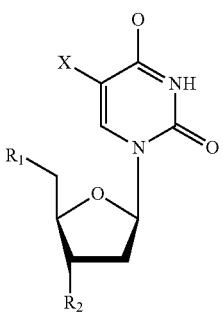

Formula (IIb)

wherein X, $R_1$ and $R_2$ are as defined above.

More preferably, the compound of Formula (I) is a compound of Formula (IIa), or a stereoisomer, solvate, tautomer or pharmaceutically acceptable salt thereof.

In these preferred embodiments, particularly in Formula (IIa), preferably X is —($CH_2$)$_n$—X', wherein n is from 0 to 6 and X is —OH or —CHO. Preferably X is —($CH_2$)$_n$—X', wherein n is from 0 to 6 and X' is —OH. Preferably X is —($CH_2$)$_n$—X', wherein n is from 0 to 6 and X is —CHO.

More preferably X is —($CH_2$)$_n$—X', wherein n is from 0 to 4 and X is —OH or —CHO. Preferably X is —($CH_2$)$_n$—X', wherein n is from 0 to 4 and X' is —OH. Preferably X is —($CH_2$)$_n$—X', wherein n is from 0 to 4 and X is —CHO.

More preferably X is —($CH_2$)$_n$—X', wherein n is from 0 to 2 and X is —OH or —CHO. Preferably X is —($CH_2$)$_n$—X', wherein n is from 0 to 2 and X' is —OH. Preferably X is —($CH_2$)$_n$—X', wherein n is from 0 to 2 and X is —CHO.

More preferably X is —($CH_2$)$_n$—X', wherein n is 0 or 1 and X is —OH or —CHO. Preferably X is —($CH_2$)$_n$—X', wherein n is 0 or 1 and X is —OH. Preferably X is —($CH_2$)$_n$—X', wherein n is 0 or 1 and X is —CHO.

More preferably X is —CHO, —$CH_2$OH, —$CH_2$O$CH_3$ or —$CH_2$OC(=O)$CH_3$. More preferably, X is a) —CHO or —$CH_2$OH; or b) —$CH_2$O$CH_3$ or —$CH_2$OC(=O)$CH_3$. More preferably X is —CHO or —$CH_2$OH, most preferably $CH_2$OH In Formula (IIa), preferably X is —CHO or —$CH_2$OH, most preferably —$CH_2$OH. In Formula (IIb), preferably X is —$CH_2$O$CH_3$ or —$CH_2$OC(=O)$CH_3$.

In all of these preferred embodiments, it is preferred that X is not —OH. Thus, when X' is —OH, it is preferred that n is not 0. In this case, n may be from 1 to 6, preferably from 1 to 4, more preferably from 1 to 2, and most preferably 1.

In Formula (IIa) and (IIb), preferably $R_1$ is —OH or —O(P(=O)(OH)O)$_n$H where n is from 1 to 3, preferably 3; and $R_2$ is —OH.

More preferably, the compound of Formula (I) is a compound of Formula (IIIa), (IIIb), (IIIc) or (IIId) or a stereoisomer, solvate, tautomer or pharmaceutically acceptable salt thereof:

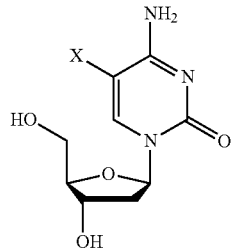

Formula (IIIa)

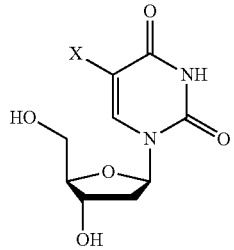

Formula (IIIb)

Formula (IIIc)

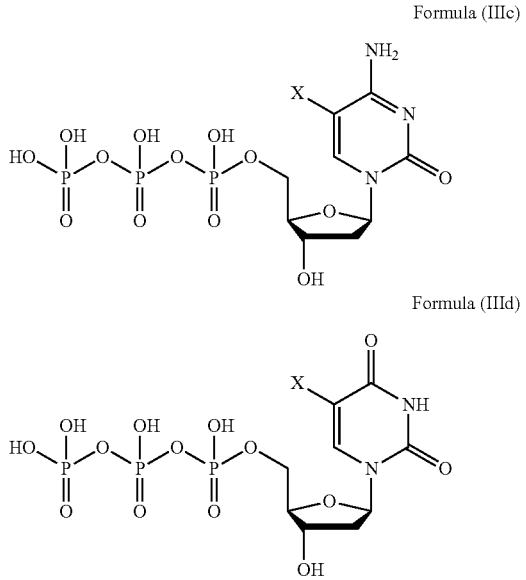

Formula (IIId)

wherein X is as defined above.

More preferably, the compound of Formula (I) is a compound of Formula (IIIa), (IIIb) or (IIIc) or a stereoisomer, solvate, tautomer or pharmaceutically acceptable salt thereof.

Even more preferably, the compound of Formula (I) is a compound of Formula (IIIa) or (IIIc), or a stereoisomer, solvate, tautomer or pharmaceutically acceptable salt thereof.

In Formula (IIIa), (IIIb), (IIIc) and (IIId), particularly in Formula (IIIa) and (IIIc), preferably X is —(CH$_2$)$_n$—X', wherein n is from 0 to 6 and X is —OH or —CHO.

Preferably X is —(CH$_2$)$_n$—X', wherein n is from 0 to 6 and X' is —OH. Preferably X is —(CH$_2$)$_n$—X', wherein n is from 0 to 6 and X is —CHO.

More preferably X is —(CH$_2$)$_n$—X', wherein n is from 0 to 4 and X is —OH or —CHO.

Preferably X is —(CH$_2$)$_n$—X', wherein n is from 0 to 4 and X' is —OH. Preferably X is —(CH$_2$)$_n$—X', wherein n is from 0 to 4 and X is —CHO.

More preferably X is —(CH$_2$)$_n$—X', wherein n is from 0 to 2 and X is —OH or —CHO.

Preferably X is —(CH$_2$)$_n$—X', wherein n is from 0 to 2 and X' is —OH. Preferably X is —(CH$_2$)$_n$—X', wherein n is from 0 to 2 and X is —CHO.

More preferably X is —(CH$_2$)$_n$—X', wherein n is 0 or 1 and X is —OH or —CHO. Preferably X is —(CH$_2$)$_n$—X', wherein n is 0 or 1 and X is —OH. Preferably X is —(CH$_2$)$_n$—X', wherein n is 0 or 1 and X is —CHO.

More preferably X is —CHO, —CH$_2$OH, —CH$_2$OCH$_3$ or —CH$_2$OC(=O)CH$_3$. More preferably, X is a) —CHO or —CH$_2$OH; or b) —CH$_2$OCH$_3$ or —CH$_2$OC(=O)CH$_3$. More preferably X is —CHO or —CH$_2$OH, most preferably CH$_2$OH In Formula (IIIa) and Formula (IIIc), preferably X is —CHO or —CH$_2$OH, most preferably —CH$_2$OH. In Formula (IIIb) and Formula (IIId), preferably X is —CH$_2$OCH$_3$ or —CH$_2$OC(=O)CH$_3$.

In all of these preferred embodiments, it is preferred that X is not —OH. Thus, when X' is —OH, it is preferred that n is not 0. In this case, n may be from 1 to 6, preferably from 1 to 4, more preferably from 1 to 2, and most preferably 1.

Most preferably, the compound of Formula (I) is a compound of Formula (IVa), (IVb), (IVc), (IVd), (IVe) or (IVf) or a stereoisomer, solvate, tautomer or pharmaceutically acceptable salt thereof:

Formula (IVa)

Formula (IVb)

Formula (IVc)

Formula (IVd)

Formula (IVe)

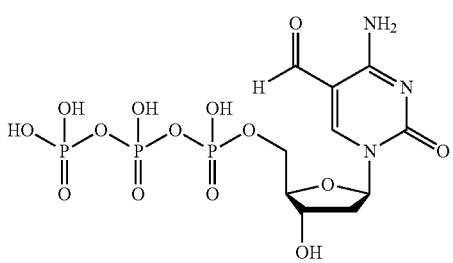

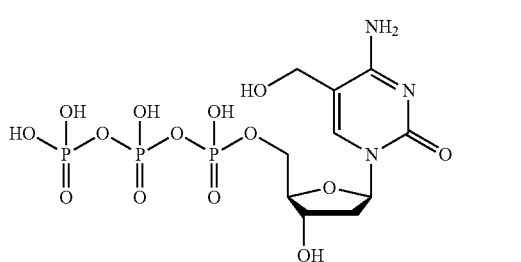

Formula (IVf)

Formula (IVa) is 5-formyl-2'-deoxycytidine (also termed 5f2dC, 5fdC, 2d5fC and d5fC herein). Formula (IVb) is 5-hydroxymethyl-2'-deoxycytidine (also termed 5hm2dC, 5hmdC, 2d5hmC and d5hmC herein). Formula (IVc) is 5-methoxymethyl-2'-deoxyuridine. Formula (IVd) is 5-acetoxymethyl-2'-deoxyuridine Formula (IVe) is 5-formyl-2'-deoxycytidine-5'-triphosphate. Formula (IVf) is 5-hydroxymethyl-2'-deoxycytidine-5'-triphosphate.

Thus, preferably, the compound of use in the invention is selected from is 5-formyl-2'-deoxycytidine, 5-hydroxymethyl-2'-deoxycytidine, 5-methoxymethyl-2'-deoxyuridine, 5-acetoxymethyl-2'-deoxyuridine, 5-formyl-2'-deoxycytidine-5'-triphosphate and 5-hydroxymethyl-2'-deoxycytidine-5'-triphosphate or a stereoisomer, solvate, tautomer or pharmaceutically acceptable salt thereof. More preferably the compound is a) 5-formyl-2'-deoxycytidine or 5-hydroxymethyl-2'-deoxycytidine or a stereoisomer, solvate, tautomer or pharmaceutically acceptable salt thereof; or b) 5-methoxymethyl-2'-deoxyuridine or 5-acetoxymethyl-2'-deoxyuridine or a stereoisomer, solvate, tautomer or pharmaceutically acceptable salt thereof Alternatively, the compound of use in the invention is preferably selected from 5-formyl-2'-deoxycytidine, 5-hydroxymethyl-2'-deoxycytidine, 5-formyl-2'-deoxycytidine-5'-triphosphate and 5-hydroxymethyl-2'-deoxycytidine-5'-triphosphate or a stereoisomer, solvate, tautomer or pharmaceutically acceptable salt thereof.

Most preferably, the compound is 5-formyl-2'-deoxycytidine or 5-hydroxymethyl-2'-deoxycytidine or a stereoisomer, solvate, tautomer or pharmaceutically acceptable salt thereof, most preferably 5-hydroxymethyl-2'-deoxycytidine or a stereoisomer, solvate, tautomer or pharmaceutically acceptable salt thereof.

The term "treatment" or "therapy" includes any treatment or therapy which results in an improvement in the health or condition of a patient, or of a symptom of the cancer they are suffering. "Treatment" is not limited to curative therapies (e.g. those which result in the elimination of cancer cells or tumours or metastases from the patient), but includes any therapy which has a beneficial effect on the cancer or the patient, for example, tumour regression or reduction, reduction of metastatic potential, increased overall survival, extension or prolongation of life or remission, induction of remission, a slow-down or reduction of disease progression or the rate of disease progression, or of tumour development, subjective improvement in quality of life, reduced pain or other symptoms related to the disease, improved appetite, reduced nausea, or an alleviation of any symptom of the cancer.

Thus, as used herein 'treatment' may refer to reducing, alleviating, ameliorating or eliminating the cancer, or one or more symptoms thereof, which is being treated, relative to the cancer or symptom prior to the treatment. Treatment may include a reduction or elimination of cancer cells, for example in tumours, e.g. in solid tumours. Treatment is treatment of a subject, i.e. a subject in need thereof. Thus, treatment may include a reduction in tumour size, or the prevention of tumour growth or further tumour growth, i.e. stabilization of tumour size.

"Prevention" refers to delaying or preventing the onset of the symptoms of the cancer, e.g. in the development of a tumour.

Preferably, the compounds of the invention have a direct effect on cancer/tumour cells. A "direct effect" as used herein means that the compounds of the invention interact directly with cancer/tumour cells in order to exert their anti-cancer/anti-tumour effects. In other words, preferably the compounds of the invention, i.e. the compounds of Formula (I) are cytotoxic to cancer/tumour cells. Preferably, the compounds of the invention are administered to a subject in order to exert a direct effect against cancer/tumour cells.

Preferably, the methods of the invention do not comprise administration of the compounds of the invention in order to deplete a population of cells which has been administered as part of a cell-based therapy. Cell based therapies are well-known as therapies in which a population of cells is administered to a subject in order to elicit a particular therapeutic effect. Well-known cell-based therapies include T-cell therapy, e.g. CAR T-cell therapy.

Preferably, the methods of the invention do not comprise administration of the compounds of the invention after administration of a population of cells which has been administered as part of a cell-based therapy.

Preferably, the methods of the invention do not comprise CAR T-cell therapy. Preferably, the methods of the invention do not comprise T-cell therapy. Preferably the methods of the invention do not comprise cell-based therapies.

Preferably the methods of the invention comprise administration of the compound of the invention to a subject not undergoing CAR T-cell therapy, preferably T-cell therapy, preferably cell-based therapy. In other words, preferably the subject has not received and will not receive CAR-T cell therapy, preferably T-cell therapy, preferably cell-based therapy as part of the their treatment.

As referred to herein a subject may be any human or non-human animal, preferably a mammalian animal, e.g. a cow, horse, sheep, pig, goat, rabbit, cat, dog, especially preferably a human. Thus, preferably the cancers referred to herein are human cancers, and the tumours referred to herein are preferably present in a human subject.

In some embodiments, treatments in accordance with the present invention may be used in subjects at risk of cancer relapse or recurrence or metastasis. Thus, alternatively viewed, the compounds of Formula (I) may be used in the prevention of cancer relapse or recurrence or metastasis.

In particular embodiments the invention may involve first identifying or determining that the subject to be treated has cancer (i.e. a tumour) or is susceptible to or at risk of developing cancer.

Alternatively or additionally, the invention may involve assessing or monitoring the effect of the administration of the compound of Formula (I) and/or the other anticancer agent(s) on the subject, or more particularly on the cancer (tumour), or on the development or progress of the cancer (tumour). Procedures and means for assessing and/or monitoring an anticancer effect are well known in the art, for example by determining or monitoring symptoms, clinical condition, tumour size or spread (e.g. by imaging techniques) or other cancer or tumour indicators e.g. cancer/tumour markers etc.

As mentioned above, the present invention is applicable to any cancer. Cancer is defined broadly herein to include any neoplastic condition, and includes particularly malignant or pre-malignant conditions. The cancer may cause or result in or manifest in solid tumours, but is not limited to such, and includes also cancers of the haempoietic system. Benign tumours and malignant tumours are also included in the term cancer as used herein, i.e. the terms cancer and tumour are used interchangeably. The treatment of malignant tumours is preferred.

The cancer/may occur in any tissue or organ of the body. For example, the present invention can be used in the treatment or prevention of any of the following cancers in a patient or subject:

Cancer of the Central Nervous System, preferably Brain Cancer, preferably Glioma; Acute Lymphoblastic Leukaemia (ALL); Acute Myeloid Leukaemia (AML); Adrenocortical Carcinoma; AIDS-Related Cancer (e.g. Kaposi Sarcoma and Lymphoma); Anal Cancer; Appendix Cancer; Basal Cell Carcinoma; Bile Duct Cancer; Extrahepatic Bladder Cancer; Bone Cancer (e.g. Ewing Sarcoma; Osteosarcoma and Malignant Fibrous Histiocytoma); Breast Cancer; Bronchial Tumours; Burkitt Lymphoma; Carcinoid Tumour; Cardiac (Heart) Tumours; Cervical Cancer (Cervical Adenocarcinoma); Chordoma; Acute Promyelocytic Leukemia; Chronic Lymphocytic Leukemia (CLL); Chronic Myelogenous Leukaemia (CML); Chronic Myeloproliferative Disorder; Colon Cancer; Colorectal Cancer; Cutaneous T-Cell Lymphoma; Bile Duct Cancer; Extrahepatic Ductal Carcinoma In Situ (DCIS); Embryonal Tumours; Endometrial Cancer; Esophageal Cancer; Esthesioneuroblastoma; Ewing Sarcoma; Extracranial Germ Cell Tumour; Extragonadal Germ Cell Tumour; Extrahepatic Bile Duct Cancer; Eye Cancer (including Intraocular Melanoma and Retinoblastoma); Fibrous Histiocytoma of Bone; Gallbladder Cancer; Gastric (Stomach) Cancer; Gastrointestinal Carcinoid Tumour; Gastrointestinal Stromal Tumours (GIST); Germ Cell Tumor; Gestational Trophoblastic Disease; Hairy Cell Leukaemia; Head and Neck Cancer; Heart Cancer; Hepatocellular (Liver) Cancer; Histiocytosis; Langerhans Cell; Hodgkin Lymphoma; Hypopharyngeal Cancer; Intraocular Melanoma; Islet Cell Tumours; Pancreatic Neuroendocrine Tumours; Kaposi Sarcoma; Kidney Cancer (including Renal Cell and Wilms Tumour); Langerhans Cell Histiocytosis; Laryngeal Cancer; Leukaemia (including Acute Lymphoblastic (ALL); Acute Myeloid (AML); Chronic Lymphocytic (CLL); Chronic Myelogenous (CML); Lip and Oral Cavity Cancer; Liver Cancer (Primary); Lobular Carcinoma In Situ (LCIS); Lung Cancer; Lymphoma; Macroglobulinemia; Waldenström; Melanoma (Malignant Melanoma); Merkel Cell Carcinoma; Mesothelioma; Metastatic Squamous Neck Cancer with Occult Primary; Midline Tract Carcinoma Involving NUT Gene; Mouth Cancer; Multiple Endocrine Neoplasia Syndromes; Childhood; Multiple Myeloma/Plasma Cell Neoplasm; Mycosis Fungoides; Myelodysplastic Syndromes; Myelodysplastic/Myeloproliferative Neoplasms; Multiple Myeloma; Myeloproliferative Disorders; Nasal Cavity and Paranasal Sinus Cancer; Nasopharyngeal Cancer; Neuroblastoma; Non-Hodgkin Lymphoma; Non-Small Cell Lung Cancer; Oral Cancer; Oral Cavity Cancer; Oropharyngeal Cancer; Osteosarcoma; Ovarian Cancer (Ovarian Adenocarcinoma); Pancreatic Cancer; Pancreatic Neuroendocrine Tumours (Islet Cell Tumors); Papillomatosis; Paraganglioma; Paranasal Sinus and Nasal Cavity Cancer; Parathyroid Cancer; Penile Cancer; Pharyngeal Cancer; Pheochromocytoma; Epithelial Adenocarcinoma; Plasma Cell Neoplasm/Multiple Myeloma; Pleuropulmonary Blastoma; Pregnancy and Breast Cancer; Prostate Cancer; Rectal Cancer; Renal Cell (Kidney) Cancer; Renal Pelvis and Ureter; Transitional Cell Cancer; Retinoblastoma; Rhabdomyosarcoma; Salivary Gland Cancer; Sarcoma; Sézary Syndrome; Skin Cancer; Small Cell Lung Cancer; Small Intestine Cancer; Soft Tissue Sarcoma; Squamous Cell Carcinoma; Squamous Neck Cancer with Occult Primary; Metastatic; Stomach (Gastric) Cancer; T-Cell Lymphoma; Testicular Cancer; Throat Cancer; Thymoma and Thymic Carcinoma; Thyroid Cancer; Transitional Cell Cancer of the Renal Pelvis and Ureter; Urethral Cancer; Uterine Cancer; Endometrial; Uterine Sarcoma; Vaginal Cancer; Vulvar Cancer; Waldenström Macroglobulinemia; and Wilms Tumour.

The cells of a human embryo are arranged into distinct germ layers: an outer ectoderm an inner endoderm, and the mesoderm, which develops between the ectoderm and the endoderm. All the organs of the body develop or differentiate in an orderly fashion from these three primary germ layers.

In the present invention, preferably the cancer/tumour is a cancer/tumour of a tissue derived from the ectoderm, paraxial mesoderm, or lateral plate mesoderm, preferably from the ectoderm.

Preferably, the cancer is a cancer of the central nervous system, preferably brain cancer. For the avoidance of doubt, brain cancer is considered in the field and herein to be a cancer of the central nervous system. The central nervous system comprises the brain and the spinal cord. Thus, preferably the tumour is a tumour of the central nervous system, preferably a brain tumour. Preferably, the cancers/tumour of the CNS is selected from the group consisting of CNS lymphoma, Rhabdoid Tumour, Embryonal Tumours, Germ Cell Tumour and Chordoma, or is a brain cancer/tumour. Preferably, the brain cancer/tumour is selected from the group consisting of Glioma, Acoustic Neuroma, CNS Lymphoma, Craniopharyngioma, Medulloblastoma, Meningioma, Metastatic Brain Tumor, Pituitary Tumors, Primitive Neuroectodermal (PNET), Schwannoma, Pineal Tumor, Trilateral Retinoblastoma and Rhabdoid Tumor.

Most preferably, the cancer/tumour is brain cancer/a brain tumour, more preferably glioma. The glioma may be any type of glioma, for instance astrocytoma, ependymoma, subependymoma, oligodendroglioma, brainstem glioma, optic nerve glioma or a mixed glioma.

Preferably, the glioma is astrocytoma. The astrocytoma may be Grade I Astrocytoma (preferably Pilocytic Astrocytoma or Subependymal giant cell astrocytoma), Grade II (preferably Low-grade Astrocytoma, Pleomorphic xanthoastrocytoma or Mixed oligoastrocytoma), Grade III (Anaplastic Astrocytoma) or most preferably Grade IV (Glioblastoma).

Grading systems for the classification of tumor of the central nervous system are well-known to the person of ordinary skill in the field. Preferably, the World Health Organization (WHO) grading system is used. The WHO grading scheme is well-known in the field and is based on the appearance of certain characteristics: atypia, mitosis, endothelial proliferation, and necrosis, which reflect the malignant potential of the tumor in terms of invasion and growth rate.

Gliomas may also be classified according to whether they are above or below the tentorium; a membrane which separates the cerebrum from the cerebellum. Supratentorial gliomas are found above the tentorium, in the cerebrum, whilst infratentorial gliomas are found below the tentorium, in the cerebellum. The glioma treated according to the present invention may be supratentorial glioma or infratentorial glioma.

Thus, particularly preferably in the context of the present invention, the cancer/tumour is glioma, most preferably Glioma, Grade IV, i.e. glioblastoma multiforme. Glioblastoma multiforme is a malignant astrocytoma and the most common primary brain tumor among adults. Glioblastoma multiforme is also known as Glioma, Grade IV, glioblastoma and GBM.

Preferably the cancer/tumour is selected from the group consisting of brain cancer (as defined above, preferably glioma, more preferably glioblastoma), stomach cancer, pancreatic cancer, lymphoma, lung cancer, skin cancer, acute promyelocytic leukaemia, ovarian cancer, breast cancer, bone cancer and cervical cancer.

More preferably, the cancer/tumour is selected from the group consisting of brain cancer (as defined above, preferably glioma, more preferably glioblastoma), stomach cancer, lymphoma, breast cancer and cervical cancer.

Preferably, the cancer/tumour is selected from the group consisting of brain cancer (as defined above, preferably glioma, more preferably glioblastoma), stomach cancer, pancreatic cancer, skin cancer, acute promyelocytic leukaemia, breast cancer and cervical cancer.

Preferably, the cancer/tumour is selected from the group consisting of brain cancer (as defined above, preferably glioma, more preferably glioblastoma), skin cancer and breast cancer, more preferably brain cancer (as defined above, preferably glioma, more preferably glioblastoma) and skin cancer.

In these embodiments, the preferred compounds of the invention are those in which X contains an aldehyde functional group, preferably wherein X is —(CH$_2$)$_n$—X', wherein X' is —CHO and n is from 0 to 6, more preferably from 0 to 4, more preferably from 0 to 2, more preferably 0 or 1, most preferably wherein X is —CHO, and preferably wherein Z is —NH$_2$. As demonstrated in the present Examples, such compounds of the invention have advantageously broad cytotoxicity against a wide range of cancer types, with limited cytotoxicity against non-cancerous cells.

Alternatively preferably the cancer/tumour is selected from the group consisting of brain cancer (as defined above, preferably glioma, more preferably glioblastoma) and chronic chronic myelogenous leukemia. In these embodiments, the preferred compounds of the invention are those in which X contains an alcohol functional group, preferably wherein X is —(CH$_2$)$_n$—X', wherein X' is —OH and n is from 0 to 6, more preferably from 0 to 4, more preferably from 0 to 2, more preferably 0 or 1, most preferably wherein X is —CH$_2$OH and preferably wherein Z is —NH$_2$. As demonstrated in the present Examples, such compounds of the invention have advantageously specific cytotoxicity against these preferred cancer types, with limited cytotoxicity against off-target cancerous and non-cancerous cells.

Preferably the stomach tumour is gastric carcinoma. Preferably the pancreatic tumour is pancreatic carcinoma. Preferably, the skin cancer is malignant melanoma. Preferably the ovarian cancer is ovarian adenocarcinoma. Preferably the breast cancer is epithelial adenocarcinoma. Preferably the bone cancer is bone osteosarcoma. Preferably the lung cancer is metastatic adenocarcinoma, preferably metastatic non-small cell adenocarcinoma. Preferably the cervical cancer is cervical adenocarcinoma.

However, preferably the cancer is not lung cancer or breast cancer. Preferably the cancer is also not pancreatic cancer, stomach cancer, testis cancer or vaginal cancer. Preferably the cancer is also not kidney cancer or cancer of the intestine.

Preferably the cancer is not lung cancer. Preferably the cancer is also not prostate cancer, kidney cancer, liver cancer, breast cancer, colon cancer, ovarian cancer or cervical cancer.

Preferably the cancer/tumour is not colon cancer, lung cancer, prostate cancer or kidney cancer. Preferably the cancer/tumour is also not pancreatic cancer.

Preferably the cancer/tumour is also not chronic myelogenous leukaemia, and in this instance the preferred compounds of the invention (i.e. the compounds of Formula (I), (IIa), (IIb), (IIIa), (IIIb), (IIIc), (IIId), (Iva), (IVb), (IVc), (IVd), (IVe) and(IVf)) are those in which X contains an aldehyde functional group, preferably wherein X is —(CH$_2$)$_n$—X', wherein X is —CHO and n is from 0 to 6, more preferably from 0 to 4, more preferably from 0 to 2, more preferably 0 or 1, most preferably wherein X is —CHO and preferably wherein Z is —NH$_2$.

Furthermore, preferably the cancer is also not:
i) breast cancer, preferably also not pancreatic cancer, stomach cancer, testis cancer or vaginal cancer, more preferably also not cancer of the intestine; and/or
ii) liver cancer, breast cancer, ovarian cancer or cervical cancer.

Preferably the cancer is not a cancer selected from the group consisting of lung cancer, prostate cancer, kidney cancer, liver cancer, breast cancer, colon cancer, ovarian cancer, cervical cancer, chronic myelogenous leukemia, pancreatic cancer, stomach cancer, testis cancer, vaginal cancer and cancer of the intestine. Preferably the cancer is not any of these cancers.

Preferably, the breast cancer treated according to the present invention
i) is invasive ductal carcinoma; and/or
ii) expresses wildtype p53; and/or
iii) is not triple negative, i.e. expresses one or more of oestrogen receptor (ER+) progesterone receptor (PR+) and HER2 (HER2+), preferably is ER+ and PR+; and/or
iv) is heterozygous for p53.

The breast cancers preferably not treated according to the present invention are preferably only those breast cancer which:
i) are adenocarcinomas; and/or
ii) are triple negative, i.e. do not express oestrogen receptor (ER−) progesterone receptor (PR−) or HER2 (HER2−); and/or
iii) express a mutant variant of p53; and/or
iv) are homozygous for p53.

The human protein cytidine deaminase (CDA) catalyzes hydrolytic deamination of cytidine and deoxycytidine into uridine and deoxyuridine, respectively. Some known anticancer agents are nucleoside/nucleotide analogs, for instance gemcitabine (2,2-difluorodeoxycytidine) and cytarabine (Ara-C, cytosine arabinoside). CDA problematically inactivate such anticancer agents, including gemcitabine and cytarabine. As demonstrated in the present Examples, the compounds of the invention exert their cytotoxic effects independent of the expression of CDA.

Accordingly, in preferred embodiments, the cancer/tumour is one in which CDA is expressed, preferably in which CDA is:
i) over-expressed;
ii) not over-expressed;
iii) under-expressed;

iv) not under-expressed;
v) over-expressed or under-expressed; or
vi) neither over-expressed nor under-expressed.

Each of cancer/tumour types i) to vi) above represents a preferred embodiment of the present invention. In a particularly preferred embodiment, the cancer/tumour treated according to the present invention is one in which CDA is not over-expressed.

In the context of cancer/tumour cell gene expression, the terms "over-expressed" and "under-expressed" have a clear and widely understood meaning, namely at increased/higher or decreased/lower levels, respectively.

Over-expression (or increased or higher levels) or under-expression (or decreased or lower levels) may be as determined in comparison to any appropriate control (e.g. control level or control sample or biopsy). For example, the control level may be the level in a sample (e.g. blood or serum sample or tissue sample or biopsy) from a healthy subject (e.g. a subject not having cancer). Appropriate control levels (or control samples or values) could be readily chosen by a person skilled in the art. Appropriate control "values" could also be readily determined without running a control "sample" in every test, e.g. by reference to the range for normal subjects.

Preferably, the terms over-expressed and under-expressed mean that the level of RNA transcript from the gene in question in the cancerous cells is higher (over-expressed) or lower (under-expressed) than the level in non-cancerous cells from the same tissue as the cancerous cells, as assessed using the same method and conditions in both cases. Preferred methods and conditions for assessing the level of gene expression, e.g. CDA expression, are as disclosed elsewhere wherein.

Preferably, the over-expression or under-expression is significant. By significantly overexpressed/under-expressed, i.e. significantly higher/lower is meant statistically significantly over/under expressed (statistically significantly higher/lower). By statistically significant is meant that the observed increased or decreased level is greater than what might be expected to happen by chance alone. Statistical significance is determined by any method known in the art. For example statistical significance is determined by probability value (p-value). The p-values is a measure of probability that a difference between groups during an experiment happened by chance. For example, a p-value of 0.01 means that there is a 1 in 100 chance the result occurred by chance. The lower the p-value, the more likely it is that the difference between groups was caused by treatment. Preferably, the probability value is <0.05 or <0.01.

In some embodiments, increased levels (i.e. over-expression) may be an increase of at least 5%, at least 10%, at least 20%, at least 30%, at least 40%, at least 50% (e.g. as compared to a control level). In some embodiments, decreased levels (i.e. under-expression) may be an decrease of at least 5%, at least 10%, at least 20%, at least 30%, at least 40%, at least 50% (e.g. as compared to a control level).

Preferably, the level of gene expression in a cell of interest is determined by reference to a database containing such information. Resources such as The Cancer Genome Atlas (TCGA, https://cancergenome.nih.gov/), the EMBL-EBI expression atlas (https://www.ebi.ac.uk/gxa/home), the human protein atlas (https://www.proteinatlas.org/), GENEVESTIGATOR® (https://genevestigator.com/gv/), the Cancer Cell Line Encyclopaedia (https://portals.broadinstitute.org/ccle) and others contain information on gene expression levels in a wide range of cell types, including cancers, as well as providing statistical data on whether or not the level of gene expression in a particular cancer type is significantly higher or lower than in non-cancerous cells from the same tissue (i.e. whether the gene is over-expressed or under-expressed in the cancer type). These databases are preferred. Thus, cancer types with statistically significant over or under expression of a gene of interest can be readily identified. It is within the abilities of the person of ordinary skill in the art to utilise such resources for this purpose.

Thus preferably, the cancer/tumour is as defined anywhere herein wherein the CDA expression within said cancer/tumour is determined by reference to a database selected from the EMBL-EBI expression atlas database (https://www.ebi.ac.uk/gxa/home), the GENEVESTIGATOR® database (https://genevestigator.com/gv/), the Cancer Cell Line Encyclopaedia (https://portals.broadinstitute.org/ccle) and the human protein atlas (https://www.proteinatlas.org/).

Preferably, the cancer/tumour does not express CDA to a higher level than the expression level in non-cancerous cells from the same tissue as cancer/tumour, wherein said over-expression is determined by reference to a database selected from the EMBL-EBI expression atlas database (https://www.ebi.ac.uk/gxa/home), the GENEVESTIGATOR® database (https://genevestigator.com/gv/), the Cancer Cell Line Encyclopaedia (https://portals.broadinstitute.org/ccle) and the human protein atlas (https://www.proteinatlas.org/).

Preferably, the cancer/tumour is one wherein the CDA expression level is not greater than 90% of the CDA expression level in a reference cancer cell line as determined using the same method under the same conditions, wherein said reference cancer cell line is MDA-MB-231.

MDA-MB-231 is a well-characterised cell line which is widely available commercially. The MDA-MB-231 cell line is an epithelial, human breast cancer cell line that was established from a pleural effusion of a 51-year-old caucasian female with a metastatic mammary adenocarcinoma and is one of the most commonly used breast cancer cell lines in medical research laboratories. It can be obtained, for instance, from the European Collection of Authenticated Cell Cultures (ECACC), catalogue no. 92020424. As shown in Table 4A, the expression level of CDA in the MDA-MB-231 cell line is 153 TPM.

MDA-MB-231 is a highly aggressive, invasive and poorly differentiated triple-negative breast cancer (TNBC) cell line as it lacks oestrogen receptor (ER) and progesterone receptor (PR) expression, as well as HER2 (human epidermal growth factor receptor 2) amplification. The cell line is recognised as belonging to the claudin-low molecular subtype as it exhibits down-regulation of claudin-3 and claudinin-4, low expression of the Ki-67 proliferation marker, enrichment for markers associated with the epithelial-mesenchymal transition and the expression of features associated with mammary cancer stem cells (CSCs), such as the CD44+CD24−/low phenotype. In 3D culture, the cell line displays endothelial-like morphology and is distinguished by its invasive phenotype, having stellate projections that often bridge multiple cell colonies. Standard conditions for the culturing of this cell line are well-known. Preferred culture conditions are growth at 37° C. in Leibovitz's L-15 medium supplemented with 2 mM glutamine and 15% foetal bovine serum (FBS). This medium supports the growth of cells in environments without CO2 equilibration. MDA-MB-231 cells are preferably seeded at a density between $1-3\times10^4$ cells/cm$^2$ and subcultured when 70-80% confluent.

Preferably, the cancer/tumour is one wherein the CDA expression level is not greater than 80%, preferably not greater than 70%, preferably not greater than 60%, preferably not greater than 50%, preferably not greater than 40%, preferably not greater than 30%, preferably not greater 25% of the CDA expression level in a reference cancer cell line as determined using the same method under the same conditions, wherein said reference cancer cell line is MDA-MB-231.

Preferably, the cancer/tumour is one wherein the CDA expression level is at least 2-fold lower, preferably at least 2.5-fold lower, preferably at least 3-fold lower, preferably at least 3.5 fold lower, preferably at least 4 fold lower, preferably at least 4.5 fold lower than the CDA expression level in a reference cancer cell line as determined using the same method under the same conditions, wherein said reference cancer cell line is MDA-MB-231. "At least X-fold lower" in this context means that the maximum CDA expression level in the cancer/tumour is the value that is exactly X-fold lower than the expression level in the reference cancer cell line.

The method and conditions used to determine the CDA expression level in the cancer/tumour and in the reference cancer cell line may be any suitable method and conditions, provided that the same method and conditions are used to determine the level of CDA expression in the cancer/tumour as are used to determine the level of CDA expression in the reference cancer cell line. The reference cancer cell line is thus a control. The person of ordinary skill in the art is readily able to determine the expression level of a gene of interest, e.g. CDA, in cancerous and non-cancerous cells alike. Such methods are part of the common general knowledge in the field and any suitable method may be used in the context of the present invention.

For instance, the expression level may be measured at the protein level. Methods for measuring protein expression levels are well-known in the art. Those methods generally involve contacting a biological sample of interest with one or more detectable reagents that is or are suitable for measuring the protein's expression level, such as an antibody, and subsequently determining the protein expression level based on the level of detected reagent, preferably after normalization. Examples of methods which generally involve the use of an antibody include, without limitation, Western blot, immunoblot, enzyme-linked immunosorbant assay (ELISA), enzyme-linked immunospot (ELISPOT), radioimmunoassay (RIA), immunohistochemistry and immunoprecipitation. Other methods suitable for measuring a protein expression level, which do not necessarily involve the use of an antibody, may be used, including, without limitation, fluorescence activated cell sorting (FACS), microscopy such as atomic force microscopy, flow cytometry, microcytometry, protein binding assay, ligand binding assay, microarray, polyacrylamide gel electrophoresis such as SDS-PAGE, surface plasmon resonance (SPR), Forster resonance energy transfer (FRET), Bioluminescence resonance energy transfer (BRET), chemiluminescence, fluorescent polarization, phosphorescence, mass spectrometry such as liquid chromatography mass spectrometry (LC-MS) or liquid chromatography/mass spectrometry/mass spectrometry (LC-MS-MS), matrix-assisted laser desorption/ionization time-of-flight (MALDI-TOF), surface-enhanced laser desorption/ionization time-of-flight (SELDI-TOF), and magnetic resonance imaging (MRI).

Preferably, however, the gene expression level, e.g. the CDA expression level, may be measured at the RNA level. Methods for measuring RNA levels are well-known in the art and any suitable method may be used in the context of the present invention. For instance, microarray, RT-PCR, quantitative real time PCR, RNA sequencing, northern blots, primer extension, RNase protection and RNA expression profiling methods may be used. Preferably, the method used is RNA-seq or microarray. RNA-Seq is a well-known method, which uses next-generation sequencing (NGS) to determine the presence and quantity of RNA in a biological sample at a given moment Preferably, the method used to determine the CDA expression level in a cancer/tumour of interest as compared to the CDA expression level in a reference cancer cell line, wherein said reference cancer cell line is MDA-MB-231, is "Microarray Method A" referred to below.

Microarray Method A comprises the following steps:
1) Extracting RNA from cancer/tumour cells of interest, said extraction preferably being performed using a Norgen Total RNA Purification kit (Norgen Biotek Cat nr. 17200);
2) Preparing Poly(A)+RNA from the extracted RNA, preferably using a MEGApure kit according to the manufacturer's instructions (Ambion);
3) Preparing complementary DNA (cDNA) from the Poly (A)+RNA by treatment with reverse transcriptase, i.e. performing reverse transcription;
4) Fragmenting the cDNA using TdT (terminal deoxynucleotidyl transferase);
5) Biotinylating the cDNA fragments using the GeneChip WT Terminal labelling kit (Affymetrix);
6) Repeating steps 1 to 5 with a reference cell line, wherein said reference cell line is MDA-MB-231;
7) Hybridizing 5.5 µg of the biotinylated cDNA fragments obtained in step 5 to a first DNA microarray at 45° C. for 16 hours, and hybridizing 5.5 µg of the biotinylated cDNA fragments obtained in step 6, to a DNA microarray at 45° C. for 16 hours, preferably wherein said microarrays are Affymetrix GeneChip Human Gene 2.0 ST Arrays (Applied Biosystems);
8) Washing and staining the hybridized microarrays, preferably in the Affymetrix GeneChip Fluidics Station 450 (Applied Biosystems);
9) Scanning said stained microarrays with the Affymetrix GeneChip Scanner 3000 7G utilising the Affymetrix GeneChip Command Console® software to produce raw data signal values in the form of CEL files;
10) Normalizing the CEL files to produce gene-level expression values using the implementation of the Robust Multiarray Average (RMA) in the Affymetrix software package (version 1.36.1), preferably as described in R. A. Irizarry et al., Exploration, normalization, and summaries of high density oligonucleotide array probe level data. Biostatistics 4, 249-264 (2003);
11) Assessing array quality by computing relative log expression (RLE) and normalized unscaled standard error (NUSE) using the affyPLM package (version 1.34.0). The output from the affyPLM package is boxplots for both the RLE and NUSE distributions. Arrays for which the RLE boxplots are not centered around 0, and arrays for which the NUSE boxplots are not centered around 1, are flagged as poor quality and are excluded from subsequent analysis. If the array is excluded, then the previous steps of the method are repeated.
12) Performing Principal Component Analysis (PCA) using the Prcomp R function with expression values that have been normalized across all samples to a mean of zero and a standard deviation of one. PCA is used as a dimensionality reduction method in order to reduce the high dimensionality of the gene expression dataset while retaining most of the variation in the data. Thus, the performance of PCA achieves a lower dimensional representation of the data for downstream analysis and visualization.

13) Assessing differential expression of CDA in the cancer/tumour cells of interest and in the reference cell line MDA-MB-231 using the moderated (empirical Bayesian) t-test implemented in the limma package (version 3.14.4, http//bioinf.wehi.edu.au/imma);

wherein the microarray analysis steps 10 to 13 are performed using the R environment for statistical computing (version 2.15.1).

Preferably, the CDA expression level in a cancer/tumour of interest as compared to the CDA expression level in a reference cancer cell line, wherein said reference cancer cell line is MDA-MB-231, is determined by reference to a database selected from the EMBL-EBI expression atlas database (https://www.ebi.ac.uk/gxa/home), the GENEVESTIGATOR® database (https://genevestigator.com/gv/), the Cancer Cell Line Encyclopaedia (https://portals.broadinstitute.org/ccle) and the human protein atlas (https://www.proteinatlas.org/).

The expression level of a gene is typically presented in terms of the relative amount of RNA transcript for that gene as compared to the total amount of RNA transcripts in the cell/tissue concerned. The expression level is typically presented in units of transcripts per million (TPM), that is for every 1 million RNA molecules within the cell/tissue of interest, [x] many came from the gene of interest. Again, the level of RNA transcript in terms of TPM can be obtained by the skilled person by routine methods such as quantitative real time PCR or RNA sequencing methods, and such information is available from resources such as TCGA, the EMBL-EBI expression atlas, the GENEVESTIGATOR® database (https://genevestigator.com/gv/), the Cancer Cell Line Encyclopaedia (https://portals.broadinstitute.org/ccle) and the human protein atlas (https://www.proteinatlas.org/), amongst others. Such methods are preferred herein. Methodology for the determination of gene expression levels in TPM are described in the literature, for instance, in Wagner et al., (2012) Theory Biosci 131(4):281-285 or Mortazavi A et al., (2008) "Mapping and quantifying mammalian transcriptomes by RNA-Seq." Nature methods 5(7):621-8.

Preferably, cancerous cells/tumours which over-express CDA contain CDA RNA transcripts at a level greater than 140 TPM. Conversely, cancerous cells/tumours which do not over-express CDA preferably contain CDA RNA transcripts at a level ≤140 TPM (less than or equal to 140 TPM). Alternatively viewed, the preferred cancerous cells/tumours of the invention have a CDA expression level of ≤140 TPM. Thus, particularly preferred cancers/tumours to be treated in accordance with the present invention are those which express CDA to a level of ≤140 TPM, more preferably ≤100 TPM, more preferably ≤50 TPM.

Preferably, the expression level of CDA in a cancer/tumour of interest, in units of TPM, is obtained by reference to a database selected from the EMBL-EBI expression atlas database (https://www.ebi.ac.uk/gxa/home), the GENEVESTIGATOR® database (https://genevestigator.com/gv/), the Cancer Cell Line Encyclopaedia (https://portals.broadinstitute.org/ccle) and the human protein atlas (https://www.proteinatlas.org/).

Preferably, the level of CDA in units of TPM in a cancer/tumour of interest is determined by quantitative real time PCR, or RNA sequencing (RNA-seq) and quantification, using cells derived from said cancer/tumour. Preferably, the method used is RNA sequencing. Preferably, the method used is ""RNA-seq Method A" referred to below.

The expression level of a gene in units of TPM can be determined using any known method but is preferably determined using RNA-seq. RNA-seq methods are well-known in the art and are widely available commercially. Any suitable RNA-seq method can be used in order to determine the CDA expression level in units of TPM in a cancer of interest. The following method, termed RNA-seq Method A, is preferred, and comprises the following steps:

1. Extracting total RNA from the cancer/tumour cells of interest. This may be performed using standard RNA extraction kits, preferably QIAGEN AllPrep DNA/RNA Mini kit (Hilden, Germany) according to the manufacturer's instructions.

2. Optionally quantifying and assessing the extracted RNA for purity, preferably by an automated electrophoresis tool, preferably a 2100 Bioanalyzer (Agilent Technologies). The Agilent Bioanalyzer is a microfluidics platform used for sizing, quantification, and quality control for RNA (and DNA/proteins) and provides an "RNA Integrity Number" (RIN), which quantifies the fragmentation of the RNA sample. Preferably, samples are only used further in the process if they have an RIN of at least 7, preferably at least 8.

3. Preparing an RNA-sequencing library, preferably using the Illumina TruSeq™ RNA Sample Preparation Kit (Illumina, San Diego, Calif., USA) and the associated protocol. Preferably 500-1000 μg of total RNA is used per sample in this process. This kit and protocol is well-known in the field. This step comprises the following steps:

3a. Treating the extracted RNA to deplete bacterial and eukaryotic ribosomal RNA, preferably using the Ribo-Zero rRNA Removal Kit (Epicentre, Madison, Wis., USA), following the manufacturer's instructions 3b. Treating the remaining RNA with reverse transcriptase and random hexamers to create single-stranded cDNA fragments of 100-150 bases in length, or preferably 200-300 bases in length.

3c. Treating the single-stranded cDNA fragments with DNA Polymerase I and RNase H to produce double-stranded complemented DNA fragments (cDNA); and 3d. Ligating RNA-seq adaptors to the termini of the cDNA fragments to produce a library of adaptor-cDNA sequences capable of being analysed by RNA-seq. RNA-seq adapters are well known in the field and any suitable adapters may be used. Adapters contain functional elements which permit sequencing; for example, an amplification element and a primary sequencing site. Preferably, the adaptors are Illumina indexing adaptors. Adaptors may be ligated to one end of each cDNA fragment to produce single-end libraries (which will result in one "read" per fragment when sequenced), in which case the cDNA fragment length in step 3b is 100-150 bases. Preferably however, adaptors are ligated to both ends of each cDNA fragment to produce paired-end libraries (which will result in two "reads" per fragment when sequenced, so-called "mate reads" or "paired reads"), in which case the cDNA fragment length in step 3b is 200-300 bases.

4. Optionally amplifying the adaptor-cDNA sequences by PCR. This step may be performed if the amount of DNA is insufficient for sequence analysis step 5 to be performed. The amount of DNA required for sequence analysis is well-known to the skilled person (preferably 70-135 μl, more preferably 125 μl, of a 20 pM solution of DNA is loaded into the flow cell of the sequencer in step 5). Methods of assessing the amounts of DNA in a sample are routine, and any suitable method may be used. Preferably, the method used is fluorometry, preferably a Qubit® fluorometer is used.

5. Sequencing the adaptor-cDNA sequences, preferably using an Illumina Flowcell sequencer, preferably a Illumina Flowcell HiSeq 2500 sequencer or an Illumina Flowcell NovaSeq 6000 sequencer, preferably using a sequencing cycle of 100-150 base pairs if single-end libraries are produced in step 3, more preferably using a sequencing cycle of 200-300 base pairs with paired-end libraries being produced in step 3. Preferably 70-135 µl, more preferably 125 µl, of a 20 pM solution of DNA is loaded into the flow cell. The raw data set obtained will provide a unique sequence identifier for each fragment analysed, its sequence (a so-called "read"), and an indication of the confidence in the sequencer's determination of the sequence at each base position within the read (a so-called Phred quality score).

6. Preparing a quality-filtered data set of reads by removing from the data set of determined sequences:
   i) those bases within a read which have a Phred quality score of less than 10;
   ii) those bases within a read which are downstream of (i.e. subsequent in the direction of sequencing to) a base in the same read having a Phred quality score of less than 10;
   iii) those reads which contain any undetermined ("uncalled") bases ("N");
   iv) those reads which map to a contaminant reference genome, wherein said contaminant reference genome is the *E. coli* genome; and
   v) if the RNA-seq library used is a paired-end library, those reads whose "mate read" was discarded in one of steps 6(iii) to 6(iv).

7. Aligning the quality-filtered reads to the genome of the subject species, i.e. preferably the human genome. Preferably quality-filtered reads are aligned to the human reference genome from the Ensembl database version 98, preferably genome Human GRCh38 and Ensembl gene reference feature database (version Ensembl Genomes 45, GENCODE 32). Alignment tools suitable for this step are well-known, widely available and any suitable alignment tool can be used. Preferably, the alignment tool is TopHat2 (version 2.1.1) [Trapnell et al., (2010) *Nature Biotechnology* 28, 511-515].

8. Determining the number of read counts for the CDA gene, and optionally any other genes of interest. Bioinformatic tools for this step are well-known, widely available and any suitable tool can be used. Preferably, read counts per gene are determined using HTSeq package (htseq-count). This step thereby provides raw read count data.

9. Converting the raw read count data obtained in step 8 into units of transcripts per million (TPM). This is a standard mathematical operation, routinely used in the field. Providing count data in units of TPM allows for a meaningful assessment of gene expression levels because the determination of TPM values involves normalizing the raw data for i) Gene length; and ii) Sequencing depth.
   i) Regarding gene length normalization, in the raw data, a higher read count may be observed for longer genes purely because the genes are longer and so more fragments align with that gene. Normalizing for gene length comprises dividing the read counts for each gene by the gene length (in kilobases).
   ii) Sequencing depth is a between-sample effect that alters the comparison of read counts between the same gene in different samples. In order to normalize this, the read counts per kilobase obtained in step 9i) are divided by a "per million scaling factor", which is itself obtained by dividing the total number of reads in a sample by 1 million.

Gene expression data obtained using RNA-seq can be presented in units of RPKM (Reads Per Kilobase Million). This is calculated by
   i. Dividing the total number of reads in a sample by 1,000,000 to provide a "per million scaling factor";
   ii. Dividing the read counts per gene by the "per million" scaling factor, which normalizes for sequencing depth, thereby providing units of reads per million (RPM); and
   iii. Dividing the RPM values by the length of the gene, in kilobases, which normalizes for gene length, thereby providing units of RPKM.

Another unit of gene expression is Fragments Per Kilobase Million (FPKM), which is very similar to RPKM. RPKM is applicable when single-end RNA-seq is used, where every read corresponds to a single fragment that was sequenced. FPKM is applicable for paired-end RNA-seq, wherein two reads can correspond to a single fragment, or, if one read in the pair did not map, one read can correspond to a single fragment. The only difference between RPKM and FPKM is that FPKM takes into account that two reads can map to one fragment (and so it doesn't count this fragment twice).

TPM is very similar to RPKM and FPKM. The only difference is the order of operations (i) to (iii) above. Thus, TPM is determined as follows:
   i. Dividing the read counts per gene by the length of the gene, in kilobases, which normalizes for gene length, thereby providing units of reads per kilobase (RPK);
   ii. Dividing the total RPK value in a sample by 1,000,000 to provide a "per million scaling factor"; and
   iii. Dividing the RPK values obtained in step (i) by the "per million" scaling factor obtained in step (ii), which normalizes for sequencing depth, thereby providing units of TPM.

The only difference when calculating TPM as compared to RPKM or FPKM is that when calculating TPM normalization for gene length is performed first. However, the result is that when using units of TPM, the sum of all TPMs in each sample are the same—1 million. This allows more meaningful comparison of the proportion of reads that mapped to a gene in each sample.

The above described RNA-seq Method A, of determining the expression level of CDA in units of TPM can also be used to determine the expression level of CDA in a cancer/tumour of interest, in units of TPM, as compared to a control, i.e. control cells, as defined above or a reference cell line, wherein said reference cell line is MDA-MB-231. In these embodiments, the RNA-seq Method A may be performed using the cancer/tumour cells of interest and repeated with the control or reference cells, wherein the TPM values determined are then compared. Alternatively, the RNA-seq Method A may be performed using the cancer/tumour cells of interest and the CDA expression level determined in units of TPM is compared to a value for the CDA expression level in units of TPM previously obtained using the control or reference cell line using the same method.

Alternatively, the level of expression of a gene can be determined via microarray, which is a standard technique in the field. Any suitable microarray technique can be used in the context of the present invention. Microarrays permit the detection of expression of thousands of genes simultaneously.

The level of gene expression determined by microarray can be expressed on any scale, e.g. a linear scale. Data from microarrays may also be transformed, preferably by the logarithm base 2 transformation, which has the advantage of producing a continuous spectrum of values and treating up- and downregulated genes in a similar fashion. A gene up-regulated by a factor of 2 has a log 2 transformed value of 1.

Preferably, the cancer/tumour is one in which the logarithm base 2 transformed CDA expression level is less than 11.75. Such cancers/tumours are described as not over-expressing CDA. Preferably the cancer/tumour is one in which the logarithm base 2 transformed CDA expression level is less than 11.5, more preferably less than 11, more preferably less than 10.5, more preferably less than 10, more preferably less than 9.5.

Preferably, the cancer/tumour is one in which the linear CDA expression level is less than 6500. Such cancers/tumours are described as not over-expressing CDA. Preferably the cancer/tumour is one in which the linear CDA expression level is less than 6000, more preferably less than 5000, more preferably less than 4000, more preferably less than 3000, more preferably less than 2000, more preferably less than 1500.

Preferably, the linear or logarithm base2 transformed expression level of CDA in a cancer/tumour of interest is obtained by reference to a database selected from the EMBL-EBI expression atlas database (https://www.ebi.ac.uk/gxa/home), the GENEVESTIGATOR® database (https://genevestigator.com/gv/), the Cancer Cell Line Encyclopaedia (https://portals.broadinstitute.org/ccle) and the human protein atlas (https://www.proteinatlas.org/).

The skilled person is aware that there may be variation in expression levels of some genes between tumours of the same cancer type. For instance, some breast cancers may over-express CDA and others may not over-express CDA. Thus, preferably, the cancers/tumours described anywhere elsewhere herein as preferred are preferably cancers/tumours of those types in which CDA is expressed, preferably in which CDA is:
  i) over-expressed;
  ii) not over-expressed;
  iii) under-expressed;
  iv) not under-expressed;
  v) over-expressed or under-expressed; or
  vi) neither over-expressed nor under-expressed.
Preferably, the cancer/tumour is one in which CDA is not over-expressed. Preferably, the cancer/tumour is one in which CDA is over-expressed. CDA over-expression is as defined above.

Conversely, the cancers described anywhere else herein as not preferred are preferably only cancers/tumours of those types in which CDA is:
  i) over-expressed;
  ii) not over-expressed;
  iii) under-expressed;
  iv) not under-expressed;
  v) over-expressed or under-expressed; or
  vi) neither over-expressed nor under-expressed.
Preferably, the cancer/tumour is not one in which CDA is over-expressed. CDA over-expression is as defined above.

In a preferred embodiment, the cancer/tumour is resistant to gemcitabine and/or cytarabine treatment. Thus, the cancers/tumours described anywhere elsewhere herein as preferred are preferably cancers/tumours of those types which are resistant to gemcitabine and/or cytarabine treatment treatment. Preferably the gemcitabine and/or cytarabine resistant cancer/tumour is brain cancer, preferably glioma, more preferably glioblastoma multiforme.

The human protein 0-6-methylguanine-DNA methyltransferase (MGMT) removes alkylated DNA damage. The expression of MGMT makes cancer cells, such as glioblastoma cells, almost completely resistant to the cytotoxic effects of Temozolomide, which exerts its cancer chemotherapeutic activity by mutating tumor cells so severely that the tumor cells are killed. Temozolomide works by alkalyting DNA, thereby causing mutations.

As shown in the present Examples, the compounds of Formula (I) are not mutagenic in a HPRT assay. Accordingly, the compounds of Formula (I) are of use particular use in treating cancers in which MGMT is expressed, preferably over-expressed. Thus, the cancers/tumours described anywhere elsewhere herein as preferred are preferably cancers/tumours of those types in which MGMT is expressed, preferably over-expressed.

Temozolomide (4-methyl-5-oxo-2,3,4,6,8-pentazabicyclo[4.3.0]nona-2,7,9-triene-9-carboxamide) is the first-line treatment for glioblastoma multiforme, and is also used in the treatment of some other brain cancers. As shown in the present Examples however, temozolomide effectively kills less than half of glioblastoma cell lines evaluated, and temozolomide resistant cell lines are effectively killed by the compounds of the invention. Thus, in a preferred embodiment, the cancer/tumour is temozolomide resistant cancer/tumour.

Thus, the cancers/tumours described anywhere elsewhere herein as preferred are preferably cancers/tumours of those types which are resistant to Temozolomide treatment. Preferably, the temozolomide resistant cancer/tumour is brain cancer, preferably glioma, more preferably glioblastoma multiforme.

As shown in the present Examples, 5-fluorouracil resistant cell lines are effectively killed by the compounds of the invention. Thus, in a preferred embodiment, the cancer is fluoropyrimidine resistant cancer. Thus, the cancers/tumours described anywhere elsewhere herein as preferred are preferably cancers/tumours of those types which are resistant to fluoropyrimidine treatment. preferably the fluoropyrimidine resistant cancer/tumour is brain cancer, preferably glioma, more preferably glioblastoma multiforme. Preferably the fluoropyrimidine is 5-fluorouracil.

Preferably the cancer/tumour is resistant to both Temozolomide and fluoropyrimidine treatment.

The term "resistant" in the context of cancer/tumour therapy has a clear and well-understood meaning in the art. By "resistant" is meant that the cancer/tumour does not respond positively to treatment with the anticancer agent(s) concerned, i.e. that treatment with the anticancer agent(s) does not reduce, alleviate, ameliorate or eliminate the cancer, or one or more symptoms thereof, or reduce or eliminate cancer cells within the tumour, relative to the cancer, tumour or symptom prior to the treatment. A cancer/tumour may be resistant at the beginning of treatment, or it may become resistant during treatment.

As mentioned above, in the treatment or prevention of cancer the compound of Formula (I) may be used alone or optionally in combination with a further, i.e. one or more further, anticancer agent(s). In all aspects and embodiments of the present invention, the further anticancer agent may be any suitable anti-cancer agent known in the art. A wide range of different types of agents are known or proposed for use in the treatment of cancer and any of these may be used, regardless of chemical nature or mode of action.

Anticancer agents thus included chemical molecules whether naturally or synthetically derived or prepared (e.g organic small chemical molecules) and biological molecules such as proteins and peptides (e.g. immunotherapy agents as discussed below). Anticancer drugs thus include chemotherapeutic agents or drugs, which may be in a wide range of different chemical or functional classes, as well as antibodies or antibody derivatives and other biological molecules which act for example to stimulate, activate or enhance various physiological processes or cells in the body, for example immune and/or anti-inflammatory responses or cells etc.

Representative examples of anticancer agents in the "chemotherapy" class include but are not limited to fludarabine, gemcitabine, capecitabine, methotrexate, taxol, taxotere, mercaptopurine, thioguanine, hydroxyurea, cytarabine, cyclophosphamide, ifosfamide, nitrosoureas, platinum complexes such as cisplatin, carboplatin and oxaliplatin, mitomycin, dacarbazine, procarbazine, etoposide, teniposide, campathecins, bleomycin, doxorubicin, idarubicin, daunorubicin, dactinomycin, plicamycin, mitoxantrone, L-asparaginase, epimbicm, 5-fluorouracil, taxanes such as docetaxel and paclitaxel, leucovorin, levamisole, irinotecan, estramustine, etoposide, nitrogen mustards, BCNU, nitrosoureas such as carmustme and lomustine, vinca alkaloids such as vinblastine, vincristine and vinorelbine, imatimb mesylate, hexamethyhnelamine, or topoteca.

Anticancer agents may include kinase inhibitors, phosphatase inhibitors, ATPase inhibitors, tyrphostins, protease inhibitors, herbimycin A, genistein, erbstatin, and lavendustin A.

In one embodiment, the anticancer agent may be selected from, but is not limited to, one or a combination of the following class of agents: alkylating agents, plant alkaloids, DNA topoisomerase inhibitors, anti-folates, pyrimidine analogs, purine analogs, DNA antimetabolites, taxanes, podophyllotoxin, hormonal therapies, retinoids, photosensitizers or agents for use in photodynamic therapies, angiogenesis inhibitors, antimitotic agents, isoprenylation inhibitors, cell cycle inhibitors, actinomycins, bleomycins, anthracyclines, MDR inhibitors and Ca2+ ATPase inhibitors.

Further anticancer agents may be selected from, but are not limited to, cytokines, chemokines, growth factors, growth inhibitory factors, hormones, soluble receptors, decoy receptors, monoclonal or polyclonal antibodies, mono-specific, bi-specific or multi-specific antibodies, monobodies, polybodies.

Alternative anticancer agents may be selected from, but are not limited to, growth or hematopoietic factors such as erythropoietin and thrombopoietin, and growth factor mimetics thereof.

In one representative embodiment the drug is a small molecule, and more particularly a small molecule chemotherapeutic agent. A small molecule agent may be defined as having a molecular weight of less than 2000 Da, more particularly less than 1800, 1500, 1200, 1000, 900, 800 or 700 Da., typically less than 1000 Da. For example, a small molecule agent may have a size in the range of 100-1000 Da, e.g. 100-800 Da or 300-700 Da.

In an alternative embodiment, the further anticancer agent is an immunotherapy agent. Induction of an immune response to treat cancer is known as cancer "immunotherapy". Immunotherapy can involve, for example, cell-based therapies, antibody therapies or cytokine therapies. All three approaches exploit the fact that cancer cells often have different cell-surface markers, or cancer antigens, which are detectable by the immune system. These antigens are most commonly proteins but may also include other molecules such as carbohydrates. Another example of immunotherapy is by checkpoint inhibition, whereby checkpoint proteins are inhibited. This is discussed further below.

Immunotherapy is thus used to provoke the immune system into attacking cancer cells, and as discussed further below, various molecules may be the target of immunotherapy-based approaches. For example, targets for immunotherapeutic intervention in cancer include "CD" ("cluster of differentiation") proteins such as CD52, CD30, CD33, CD20, CD152 (also known as CTLA4) and CD279 (also known as programmed cell death 1 protein PD-1); growth factors such as vascular endothelial growth factor (VEGF); growth factor receptors such as epidermal growth factor receptor (EGFR) or human epidermal growth factor receptor 2 (HER2); Lymphocyte-activation gene 3 (LAG3); and B7 family proteins such as B7-H3 and B7-H4. These are merely representative examples however, and other molecules may be targets for immunotherapeutic intervention in cancer.

The immunotherapy agent can be a peptide, polypeptide or protein. The immunotherapy agent may be selected from an antibody, a cytokine and a checkpoint inhibitor. As noted above a therapeutic anticancer antibody may have a range of targets, including checkpoint proteins. Thus, an antibody may be a checkpoint inhibitor.

Thus, in a first example, the immunotherapeutic agent is an antibody. The antibody may be selected from monoclonal or polyclonal antibodies, mono-specific, bi-specific or multi-specific antibodies, monobodies and polybodies or indeed from any of the many antibody-like or antibody derivative molecules known in the art today. Accordingly the term "antibody" is used broadly herein and includes any such antibody and any antibody fragment, derivative or variant as in the known in the art. The antibody may be of any convenient or desired species, class or sub-type. Furthermore, the antibody may be natural, derivatised or synthetic.

The antibody may accordingly be:
  (a) any of the various classes or subclasses of immunoglobulin e.g. IgG, IgA, IgM, IgD or IgE derived from any animal e.g. any of the animals conventionally used e.g. sheep, rabbits, goats, or mice or egg yolk;
  (b) monoclonal or polyclonal antibodies;
  (c) intact antibodies or fragments of antibodies, monoclonal or polyclonal, the fragments being those which contain the binding region of the antibody e.g. fragments devoid of the Fc portion (e.g. Fab, Fab', F(ab')2, Fv), the so called "half molecule" fragments obtained by reductive cleavage of the disulphide bonds connecting the heavy chain components in the intact antibody. Fv may be defined as a fragment containing the variable region of the light chain and the variable region of the heavy chain expressed as two chains;
  (d) antibodies produced or modified by recombinant DNA or other synthetic techniques, including monoclonal antibodies, fragments of antibodies, humanised antibodies, chimeric antibodies, or synthetically made or altered antibody-like structures.

Also included are functional derivatives or "equivalents" of antibodies e.g. single chain antibodies. A single chain antibody may be defined as a genetically engineered molecule containing the variable region of the light chain, the variable region of the heavy chain, linked by a suitable polypeptide linker as a fused single chain molecule. Methods for producing antibodies and the fragments and derivatives of the antibodies are well known in the art.

In a preferred embodiment the antibody is a monoclonal antibody.

In many cases monoclonal antibodies are antibodies without modification, and most of the currently-used therapeutic antibodies fall into this category. However, in one embodiment of the present invention the antibody, for example a monoclonal antibody, is conjugated or fused to a further additional molecule, for example a toxic substance or a radioactive substance. Thus, conjugated or fused antibodies are joined to another molecule, which is either toxic to cells (e.g. a drug) or radioactive. The antibody binds to specific antigens on the surface of cancer cells and directs the toxin or radiation to the tumour.

Known and approved antibodies include: Alemtuzumab, Bevacizumab, Brentuximab vedotin, Cetuximab, Gemtuzumab ozogamicin, Ibritumomab tiuxetan, Ipilimumab, Ofatumumab, Panitumumab, Rituximab, Tositumomab and Trastuzumab.

In a second example, the immunotherapeutic agent is a cytokine. Cytokines include immunomodulating agents, such as interleukins (IL) and interferons (IFN) and also colony stimulating factors, tumour necrosis factors (TNF) and other regulatory molecules. Cytokines have been classed as lymphokines, interleukins, and chemokines, based on their function, cell of secretion, or target of action. Each cytokine has a matching cell-surface receptor, which initiates cascades of intracellular signalling which alter cell functions. In the context of cancer, cytokines are produced by many cell types present within a tumour. Cytokines are well known in the art and all such cytokines are encompassed for use according to the invention. As such, in one embodiment the immunotherapeutic agent is a cytokine. In a preferred embodiment the cytokine is an interleukin or an interferon.

Interleukins are a group of cytokines with a wide array of effects on the immune system. Examples of interleukins (ILs) are IL-1, IL-2, IL-3, IL-4, IL-5, IL-6, IL-7, IL-8, IL-9, IL-10, IL-11, IL-12, IL-13, IL-15 and IL-17.

Interferons are cytokines produced by the immune system usually involved in anti-viral response, but also have use in the treatment of cancer. There are three groups of interferons (IFNs): type I (IFNα and IFNβ), type 2 (IFNγ) and the relatively newly discovered type III (IFNA).

All known forms of the above-discussed cytokines can be used in the present invention, including also functionally equivalent variants, derivatives and fragments thereof. Thus the term "cytokine" as used herein includes amino acid sequence variants of known cytokine polypeptides, and fragments of a cytokine polypeptide, or derivative thereof, as long as such fragments, variants or derivatives are active, or "functional", i.e. retain at least one function or activity (e.g. biological activity) of the relevant cytokine. The cytokine may be a recombinant polypeptide, a synthetic polypeptide or may be isolated from a natural source. Suitable cytokines are commercially available and would be known to the skilled man, for example human cytokines are available from GenScript (Piscataway, N.J., USA).

In a third example, the immunotherapeutic agent is an agent that targets an immune checkpoint, i.e. is a checkpoint inhibitor. Checkpoint proteins keep the immune system in check by indicating to the immune system which cells are healthy and which cells should be destroyed. Checkpoint proteins act as a "brake" on the immune system by preventing T-cell activation. If a cell does not have sufficient checkpoint proteins on its surface it may be destroyed by the immune system. In the case of cancer cells, whilst there may be molecules signalling that the cell is cancerous, if there are enough checkpoint proteins on the cell surface, the cell may evade the immune response, and it has been speculated that checkpoint proteins contribute to a lack of success in some cancer immunotherapies.

Several checkpoint inhibitors are known and can be used in the present invention, for example those inhibitors described in Creelan (2014) Cancer Control 21:80-89.

Examples of checkpoint inhibitors include: Tremelimumab (CP-675,206); Ipilimumab (MDX-010); Nivolumab (BMS-936558); MK-3475 (formerly lambrolizumab); Urelumab (BMS-663513); anti-LAG-3 monoclonal antibody (BMS-986016); and Bavituximab (chimeric 3G4). All of these checkpoint inhibitors can be used in the present invention.

An alternative option for immunotherapy relates to immune cell therapies, and the present invention can also be used in combination with such therapies, for example adoptive cell transfer. A number of T-cell-based therapies for treating cancer have been developed, and these treatments, known as adoptive cell transfer (ACT) have become increasingly attractive during recent years. Three main ACT strategies have been exploited thus far. The first of these, and the most developed, involves the isolation of patient's own tumour-reactive T-cells from peripheral or tumour sites (known as Tumour Infiltrating Lymphocytes (TILs)). These cells are expanded ex vivo and re-injected into a patient.

Two alternative therapies are available, which involve modification of a patient's own T-cells with receptors capable of recognising a tumour. In one option, TcRs having activity towards a cancer antigen can be isolated and characterised, and a gene encoding the TcR can be inserted into T-cells and re-injected into a patient. This therapy has been shown to shrink solid tumours in some patients, but is associated with a significant drawback: the TcRs used must be matched to a patient's immune type. Accordingly, as an alternative to the use of TcRs, therapies involving the expression of Chimeric Antigen Receptors (CARs) in T-cells have also been suggested. CARs are fusion proteins comprising an antibody linked to the signalling domain of the TcR complex, and can be used to direct T cells against a tumour if a suitable antibody is selected. Unlike a TCR, a CAR does not need to MHC-matched to the recipient.

Alternatively, the cell may be a natural killer (NK) cell, which optionally may be modified to express a CAR.

As such, according to the present invention the immunotherapeutic agent may be a cell, particularly an immune cell such as a lymphocyte, particularly a T cell or NK cell as described above, e.g. the T cell may be a TIL or be modified to express a TcR or CAR. The NK may be modified to express a CAR.

An alternative option for the further anticancer agent is a microRNA (miRNA). MicroRNAs are small non-coding RNA molecule (containing about 22 nucleotides) found in plants, animals, and some viruses, which functions in RNA silencing and post-transcriptional regulation of gene expression. miRNAs function via base-pairing with complementary sequences within mRNA molecules. As a result, these mRNA molecules are silenced by cleavage of the mRNA strand into two pieces, destabilization of the mRNA through shortening of its poly(A) tail, or less efficient translation of the mRNA into proteins. miRNAs resemble the siRNAs mentioned above, except miRNAs derive from regions of RNA transcripts that fold back on themselves to form short hairpins, whereas siRNAs derive from longer regions of double-stranded RNA. Many miRNAs have been found to have links with various types of cancer and accordingly are sometimes referred to as "oncomirs".

MicroRNAs can be used in microRNA-based oncology therapeutics in the treatment of cancer. The rationale for developing miRNA therapeutics is based on the premise that aberrantly expressed miRNAs play key roles in the development of cancers, and that correcting these miRNA deficiencies by either antagonizing or restoring miRNA function may provide a therapeutic benefit, e.g. by miRNA replacement therapy Any suitable miRNA may be used as the further anticancer agent according to the present invention. The miRNA may be in free form, i.e. not bound to another molecule. Alternatively, the miRNA may be conjugated or bound to another molecule, e.g. an antibody as discussed herein.

Most preferably, the further anticancer agent is selected from the group consisting of temozolomide, 5-fluorouracil, gemcitabine, cytarabine and Gliadel®. Preferably, the further anticancer agent is temozolomide. Preferably, the further anticancer agent is 5-fluorouracil. Preferably the further anticancer agent is gemcitabine. Preferably the further anticancer agent is cytarabine. Preferably the further anticancer agent is Gliadel®.

The compound of Formula (I) and the further anticancer agent may be used according to the present invention in the form of a composition, i.e. a pharmaceutical composition. The present invention provides a pharmaceutical composition comprising a compound of Formula (I) and one or more pharmaceutically acceptable excipients, optionally further comprising a further anticancer agent.

The product (particularly a pharmaceutical product) comprising a compound of Formula (I) and a further (i.e. one or more further or second) anticancer agent(s) may be a combined preparation for separate, sequential or simultaneous use in the treatment or prevention of cancer. (i.e. of a tumour), or may be a product in which the compound of Formula (I) is co-formulated with a further anticancer agent.

Thus, the compound of Formula (I) and the further anticancer agent may be formulated together in a single composition or in separate compositions for separate administration. This will depend on the nature of the further anticancer agent and its selected or required mode of administration.

The compositions for use in the invention may be formulated in any convenient manner according to techniques and procedures known in the pharmaceutical art, e.g. using one or more pharmaceutically acceptable diluents, carriers or excipients. Such formulations may be for pharmaceutical or veterinary use. Suitable diluents, excipients and carriers for use in such formulations are known to the skilled person.

"Pharmaceutically acceptable" as referred to herein refers to ingredients that are compatible with other ingredients of the compositions as well as physiologically acceptable to the recipient. The nature of the composition and carriers or excipient materials, dosages etc. may be selected in routine manner according to choice and the desired route of administration, purpose of treatment etc.

Thus, "pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The pharmaceutical compositions contain vehicles which are pharmaceutically acceptable for formulation. These may be in particular isotonic, sterile, saline solutions (monosodium or disodium phosphate, sodium, potassium, calcium or magnesium chloride and the like or mixtures of such salts), or dry, freeze-dried compositions which upon addition, depending on the case, of sterilized water or physiological saline, permit the administration of solutions.

The compounds of the invention may be presented in the conventional pharmacological forms of administration, such as tablets, coated tablets, nasal sprays, solutions, emulsions, liposomes, powders, capsules or sustained release forms. Conventional pharmaceutical excipients as well as the usual methods of production may be employed for the preparation of these forms.

To prepare pharmaceutical compositions, an effective amount of a compound of Formula (I) or further anticancer drug according to the invention may be dissolved or dispersed in a pharmaceutically acceptable carrier or aqueous medium. The compositions may comprise any known carrier, diluent or excipient. For example, formulations which are suitable for parenteral administration conveniently comprise sterile aqueous solutions and/or suspensions of pharmaceutically active ingredients preferably made isotonic with the blood of the recipient, generally using sodium chloride, glycerin, glucose, mannitol, sorbitol and the like.

Excipients that may be included in any pharmaceutical composition include preservatives (such as p-hydroxybenzoates), chelating agents (such as EDTA), stabilizing agents, tonicity adjusting agents, antimicrobial agents, flocculating/suspending agents, wetting agents, solvents and solvent systems, antioxidants and buffering agents, amongst others. It is within the competencies of the person of ordinary skill in the art to select and optimise such excipients and their amounts when formulating a pharmaceutical composition for a particular desired purpose.

Compositions are preferably in the form of aqueous solutions. Such solutions are prepared according to known methods in the art and then filled into injection vials or ampoules.

The form of the pharmaceutical compositions, the route of administration, the dosage and the regimen naturally depend upon the nature of the cancer to be treated, the severity of the illness, the age, weight, and sex of the patient, etc., or alternatively of the desired duration of treatment.

Treatment involves administration of a compound of Formula (I), optionally with a further anticancer agent.

The compounds of Formula (I) for use in accordance with the present invention may be administered to a subject via any appropriate route. The same applies to compositions or formulations comprising the compounds of Formula (I).

The compounds of Formula (I), and therefore compositions and formulations comprising the same, may be presented, for example, in a form suitable for oral, nasal, parenteral, intravenal, topical, rectal or intrathecal administration. Preferably, the compounds are presented in a form suitable for systemic (e.g. intravenous) administration.

Any mode of administration common or standard in the art may be used, e.g. injection, infusion, topical administration, inhalation, transdermal administration, both to internal and external body surfaces etc. by any suitable method known in the medicinal arts. Thus modes of administration include oral, nasal, enteral, rectal, vaginal, transmucosal, topical, or parenteral administration or by inhalation. Administration may be direct to the tumour (intratumoral administration).

Oral or parenteral administration is preferred. Preferred parenteral means of administration are intravenous, intramuscular, intraperitoneal, intracranial and subcutaneous administration, and administration to the cerebrospinal fluid (intrathecal administration). More preferably, the administration is intraperitoneal or intravenous administration, most preferably intravenous administration.

Preferably, the administration is oral or intravenous.

Intravenous administration may be intravenous injection or intravenous infusion, most preferably intravenous infusion (e.g. by infusion pump).

The compound of Formula (I) and the further anticancer agent may be administered by the same or different routes.

As noted above, the compound of Formula (I) and further anticancer agent may be administered simultaneously, separately or sequentially. In a preferred embodiment the compound of Formula (I) and further anticancer agent are administered sequentially, e.g. at separate times, i.e. not together in the same composition. In an alternate embodiment the compound of Formula (I) and further anticancer agent are administered together at the same time, for example in the same composition or in separate compositions. The timing of the separate administrations may be determined according to the particular compound of Formula (1) or the particular further anticancer agent, formulations and/or modes of administration used. Thus the compound of Formula (I) may be administered before or after the further anticancer agent.

For example the further anticancer agent may be administered first and the compound of Formula (I) may be administered at a suitable time interval afterwards to align with the optimum time of further anticancer agent delivery to the target site, or vice versa. Such determinations are entirely within the routine skill of the clinician. Thus for example the compound of Formula (I) may be administered, preferably parenterally, more preferably intravenously at least or up to 20, 30, 40, 50, 60, 70, or 90 minutes or 2, 3, 4, 5 or 6 hours before or after the further anticancer agent.

Doses and dosages may be determined in a routine manner and may depend upon the nature of the molecule, purpose of treatment, age of patient, mode of administration etc. Any therapeutic agent of the invention as above described may be combined with pharmaceutically acceptable excipients to form therapeutic compositions. A dose refers to a specified amount of medication taken at one time, i.e. the terms "single dose" and dose are used interchangeably. A course of treatment may comprise multiple doses, i.e. multiple single doses, over a period of time.

In the methods and uses of the invention, preferably an effective amount of the compound of Formula (I), and the optional further anticancer agent if present, is administered. In other words, a dose preferably comprises an effective amount of the compound of Formula (I), and the optional further anticancer agent if present.

As shown in the Examples, the compounds of Formula (I) are tolerated at high doses compared to the dose required to kill a tumour. This property differs from many chemotherapeutic compounds; indeed, the most chemotherapeutic compounds have substantial side effects at the dose required to kill the cancer. The present Examples indicate that, advantageously, compounds of Formula (I) can be administered at doses that are far in excess of the dose necessary to kill the tumor.

As shown in the Examples, mice tolerated single doses of compounds of Formula (I) of 300 mg/kg and 2000 mg/kg, but did not tolerate a single dose of 8000 mg/kg. These data suggest that in mice the maximum tolerated dose of the compounds of Formula (I) is at least 2000 mg/kg but less than 8000 mg/kg. The conversion between a mouse dose and a human dose is a factor of 0.081 (Nair et al., (2016) *Basic Clin Pharm.* 7(2): 27-31. The data in the Examples therefore indicates that in humans, the maximum tolerated dose of the compounds of Formula (I) is at least 162 mg/kg but less than 648 mg/kg.

Thus, preferably, the compound of Formula (I) is administered at a dose of ≤405 mg/kg, preferably ≤324 mg/kg, more preferably ≤243 mg/kg, more preferably ≤162 mg/kg, more preferably ≤81 mg/kg, more preferably ≤40.5 mg/kg, more preferably ≤24.3 mg/kg. Preferably, the compound of Formula (I) is administered at a dose of at least 10 mg/kg, more preferably at least 20 mg/kg, more preferably at least 30 mg/kg, more preferably at least 40 mg/kg, more preferably at least 500 mg/kg, more preferably at least 100 mg/kg.

Preferably the compound of Formula (I) is administered at a dose between 10 mg/kg and 405 mg/kg, preferably between 20 mg/kg and 324 mg/kg, more preferably between 20 mg/kg and 243 mg/kg, more preferably between 30 mg/kg and 162 mg/kg, more preferably between 40 mg/kg and 81 mg/kg.

These doses are preferred doses to human subjects.

Dosages, and dosage regimens, may vary based on parameters such as the age, weight, condition and sex of the subject, the purpose of treatment, the disease being treated, the age and/or condition of the patient, the mode of administration etc.

Appropriate dosages and regimens can be readily established. Appropriate dosage units can readily be prepared. Dosing regimens may be determined in a routine manner Treatment may comprise a single administration of the compound of Formula (I), optionally with a further anticancer agent, or may comprise repeated administrations of the compound of Formula (I), optionally with a further anticancer agent. The dosing regimen of the compound of Formula (I) and the further anticancer agent, if present, need not be identical. Alternatively, treatment may comprise a single administration of the compound of Formula (I) and repeated administrations of the further anticancer agent, or vice versa.

Preferably, the compound of Formula (I) is administered, preferably at any one of the above described doses, every 1, 2, 3, 4, 5 or 6 days, more preferably every 2, 3, or 4 days, more preferably every 3 days for a total of 2 to 10, more preferably 3 to 8, more preferably 4 to 6, more preferably 5 administrations.

However, it will be within the competencies of the person of ordinary skill in the art to determine the appropriate dosing regimen, and the relevant doses therein, based upon the nature of the compound, the purpose of treatment, the disease being treated, the age and/or condition of the patient, the mode of administration etc.

The present invention also provides a product or kit comprising a compound of Formula (I) and a further anticancer agent. The kit or product can be used in any of the uses or methods described herein, i.e. for use in treating or preventing cancer. Particularly, the kit or product is for simultaneous, separate or sequential use. Preferably the compound of Formula (I), and optionally also the further anticancer agent, is formulated for parenteral administration, preferably i.v. administration.

Each component of the kits of the present invention (i.e. each anti-cancer agent) may be provided in a separate compartment or vessel. Where convenient and practical, mixtures of components could be provided. The components may be provided in dry, e.g. crystallised, freeze dried or lyophilised, form or in solution, typically such liquid compositions will be aqueous and buffered with a standard buffer such as Tris, HEPES, etc.

Preferably the kits are for use in treating cancer, e.g. are for use in the methods or uses of the present invention as described herein.

The compounds of the invention (i.e. the compounds of Formula (I), (IIa), (IIb), (IIIa), (IIIb), (IIIc), (IIId), (Iva), (IVb), (IVc), (IVd), (IVe) and(IVf)) are either commercially available, are known in the literature, or may be obtained by conventional synthetic procedures, in accordance with standard techniques, from available starting materials using appropriate reagents and reaction conditions. In this respect, the skilled person may refer to inter alia "*Comprehensive Organic Synthesis*" by B. M. Trost and I. Fleming, Pergamon Press, 1991 and "*Protective Groups in Organic Synthesis*", 3rd edition, T. W. Greene & P. G. M. Wutz, Wiley-Interscience (1999).

The compounds of the invention are available commercially, for example from Berry and Associates, Toronto Research Chemicals, Sigma Aldrich, Carbosynth, Trilink Biotech and other well-known commercial suppliers.

The invention will be further described with reference to the following non-limiting Examples in which:

Figure 1 shows that 5-formyl-2'-deoxycytidine and 5-hydroxymethylcytidine are well tolerated in mice and reduce human glioblastoma multiforme tumors in mouse xenograft models.

FIG. 1 A: Single dose maximum tolerated dose protocol. Mice were dosed with a single intraperitoneal injection at the indicated dose. If all the mice in the relevant group tolerated the indicated dose, the dose was escalated as indicated.

FIG. 1 B: Mice body weigh was measured at the indicated time point after mice were intraperitoneally injected with the indicated dose and indicated compound every three days for a total of five doses.

FIGS. 1C-H: U87-MG cells were implanted in the flank of 32 immunodeficient mice. After tumors reached 129-131 mm$^3$, mice were divided into four groups of 8 mice. The negative control group was treated with the vehicle, the positive control group was treated with 40 mg/kg temozolomide once a day for five days, the treatment groups were treated with 2000 mg/kg 5-formyl-2'-deoxycytidine or 2000 mg/kg 5-hydroxymethyl-2'-deoxycytidine once every three days for a total of five doses. Tumor volumes were measured every three days (FIG. 1C) and the mouse body weight was measured every three days (FIG. 1 D). At the completion of the study the percent tumor growth inhibition was computed (TGI(%)) (FIG. 1 E), tumors were resected, photographed (FIG. 1F), measured (FIG. 1G) and sectioned and stained with hematoxylin and eosin (FIG. 1H).

FIG. 2 shows that 5-formyl-2'-deoxycytidine and 5-hydroxymethyl-2'-deoxycytidine kill glioblastoma multiforme by a mechanism unrelated to current nucleotide analogues:

FIG. 2A: flow cytometry of 5-formyl-2'-deoxycytidine and 5'-hydroxymethyl-2'-deoxycytidine treated cells, stained with Annexin V and 7AAD.

FIG. 2B: Survival curves of HeLa cells treated with a titration of 5-formylcytosine, 5-formylcytidine, or 5-formyl-2'-deoxycytidine.

FIG. 2C: Survival curves of U87-MG cells treated with a titration 5-hydroxymethylcytosine, 5-hydroxymethylcytidine, or 5-hydroxymethyl-2'-deoxycytidine.

Figure 6:
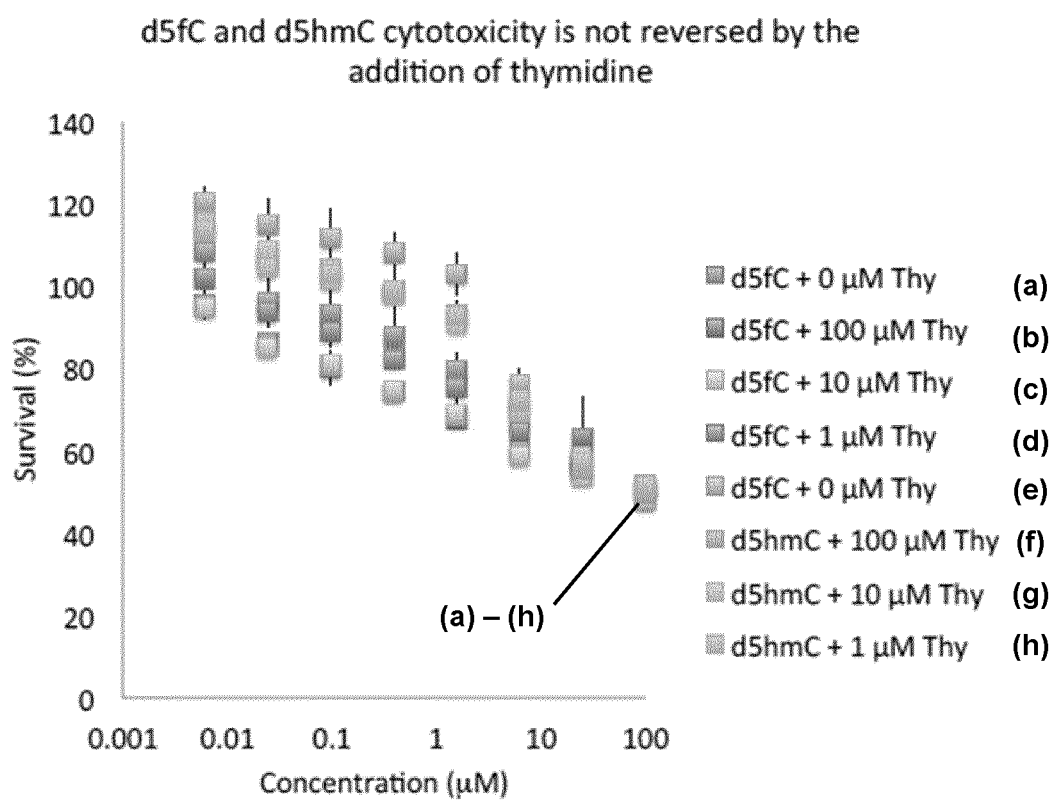

FIG. 6 shows that the cytotoxic effects(% survival) of 5-formyl-2'-deoxycytidine and 5-hydroxymethyl-2'-deoxycytidine are not rescued by the addition of thymidine in U87-MG cells, indicating that 5-formyl-2'-deoxycytidine and 5-hydroxymethyl-2'-deoxycytidine do not act by inhibiting thymidine synthase.

Figure 7:
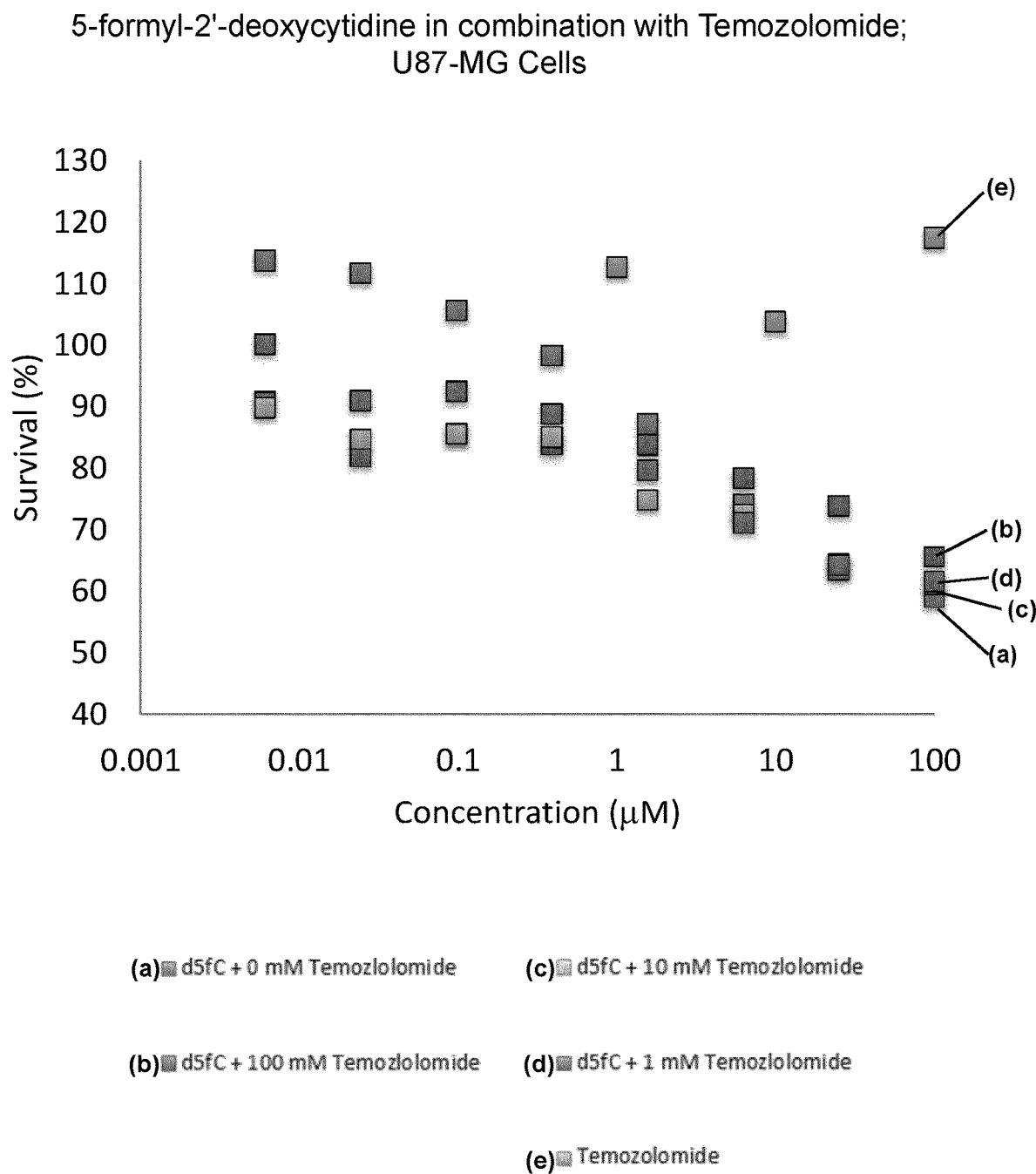

FIG. 7 shows the cytotoxic effects (% survival) of 5-formyl-2'-deoxycytidine in combination with Temozolomide in U87-MG cells.

Figure 8:
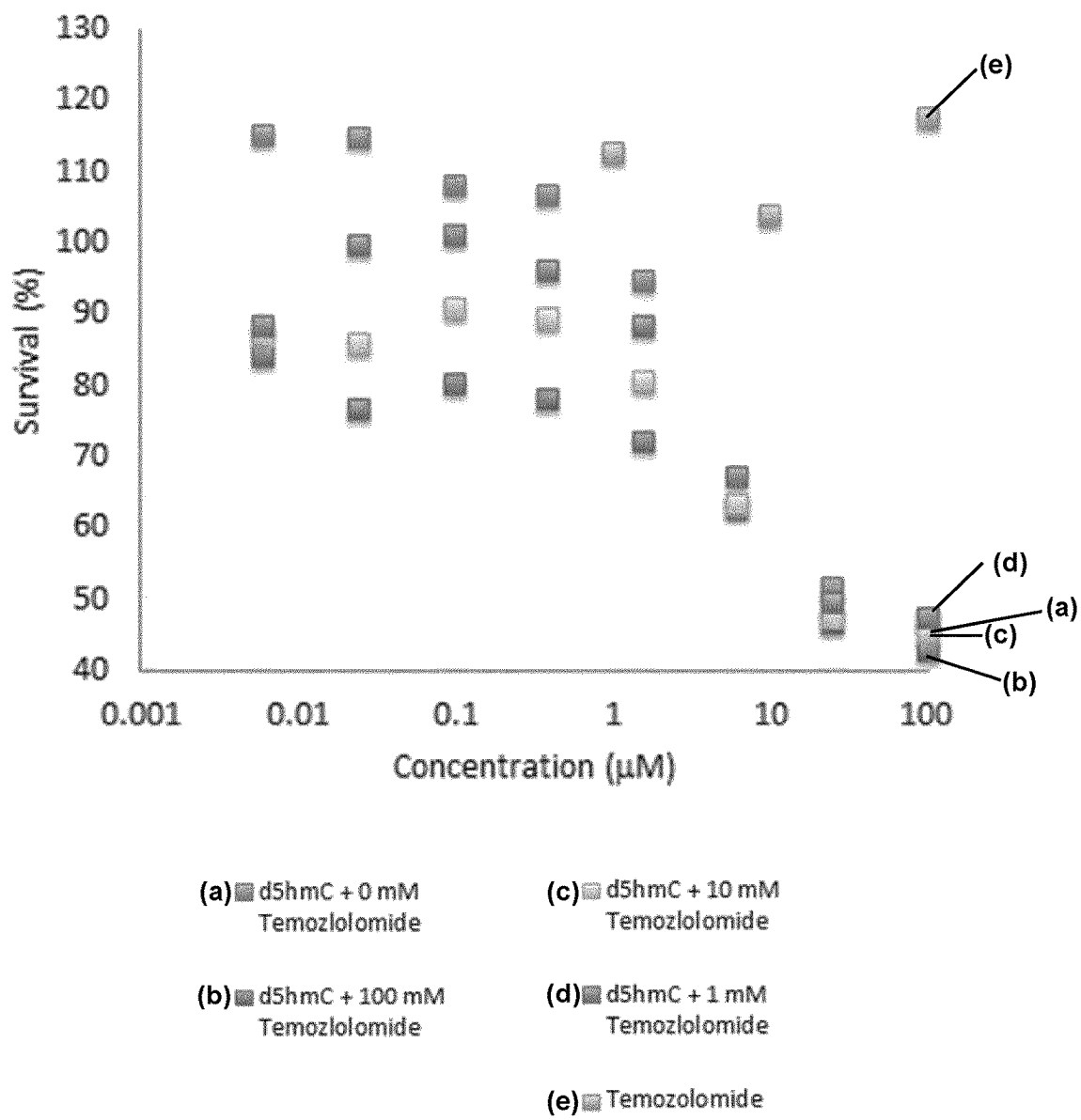

FIG. 8 shows the cytotoxic effects (% survival) of 5-hydroxymethyl-2'-deoxycytidine in combination with Temozolomide in U87-MG cells.

Figure 9:
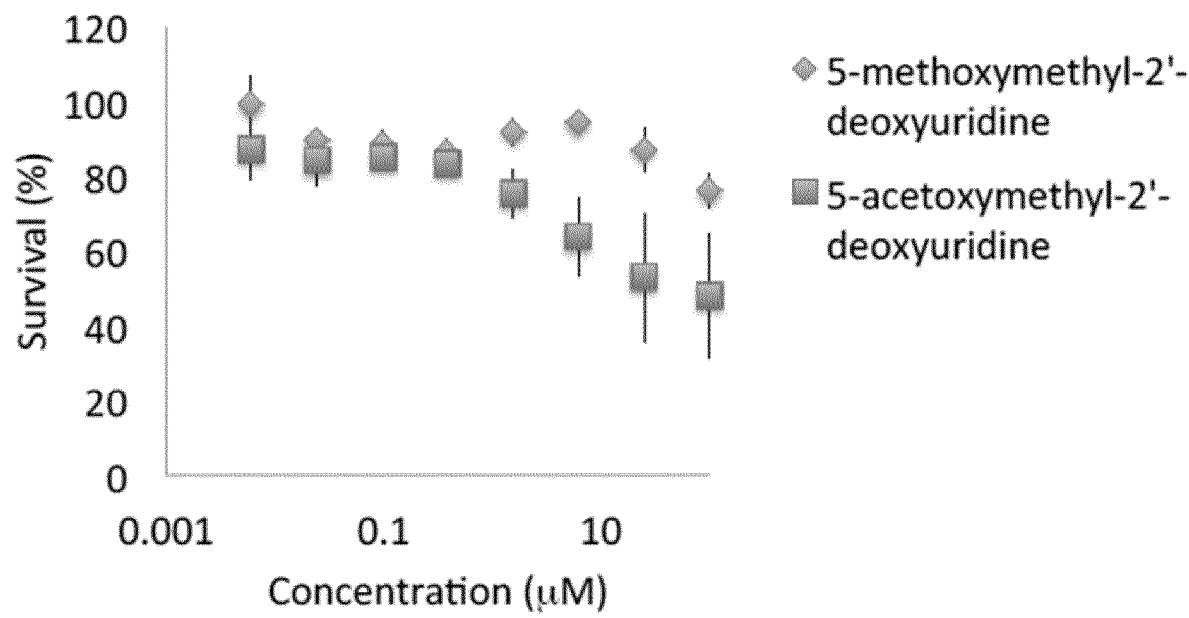
Figure 9:
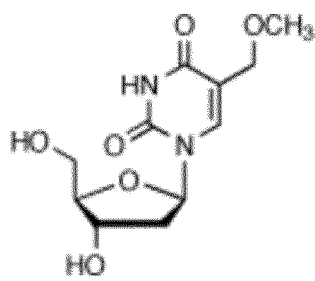
Figure 9:
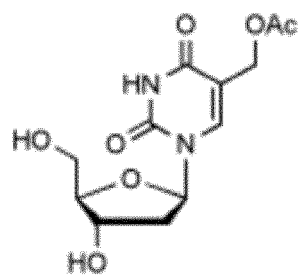

FIG. 9 shows the cytotoxic effects of 5-methoxymethyl-2'-deoxyuridine and 5-acetoxymethyl-2'-deoxyuridine on U87-MG cells. Treatment for 72 hrs. Survival was quantified using an MTT assay.

Figure 10:
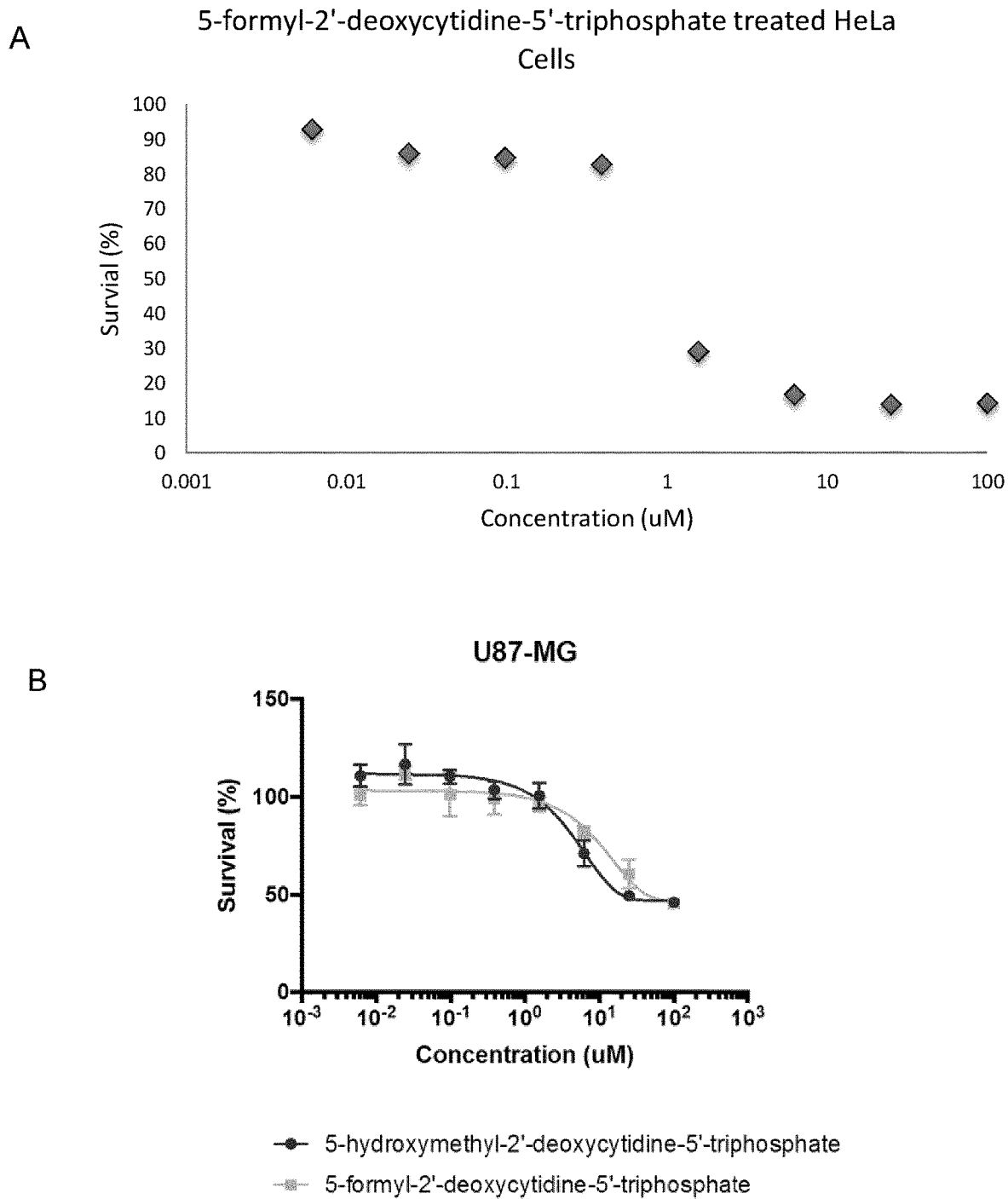

FIG. 10 shows % survival of various cells after treatment with d5fCTP or d5hmCTP FIG. 10A: % survival of HeLa after treatment with 5-formyl-2'-deoxycytidine-5'-triphosphate (d5fCTP) for 72 hrs. Survival was quantified using an MTT assay.

FIG. 10B: % survival of U87-MG cells (Glioma, Grade IV) after treatment with either 5-formyl-2'-deoxycytidine-5'-triphosphate or 5-hydroxymethyl-2'-deoxycytidine-5'-triphosphate for 72 hours. Survival was quantified using an MTT assay.

Figure 11:
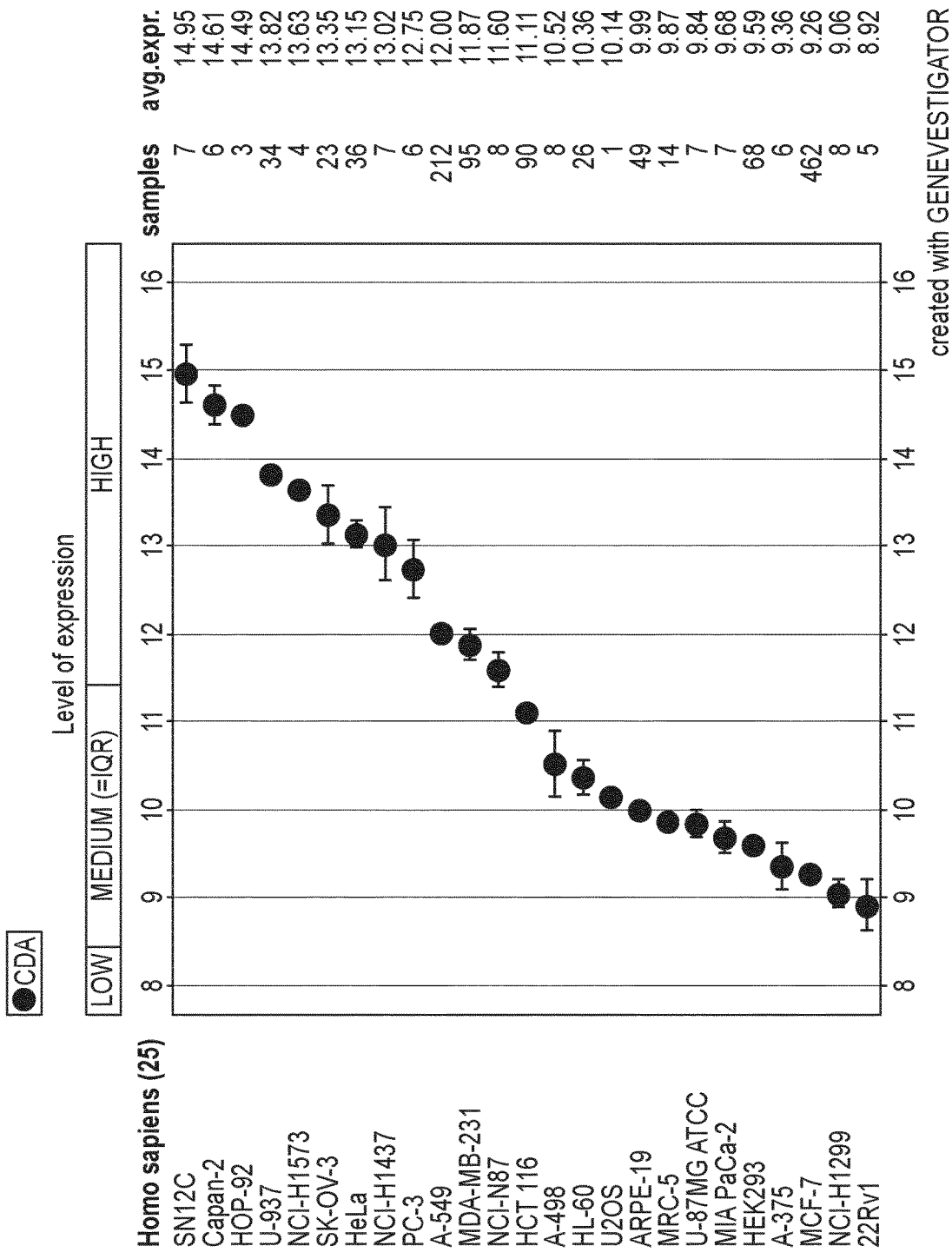

FIG. 11 shows the CDA expression levels in various cell lines. The values are normalized Log 2 CDA expression levels. The expression levels were determined using the Affymetrix Human Genome U133 Plus 2.0 Array platform and the Genevestigator database (https://genevestigator.com/gv/).

Figure 12:
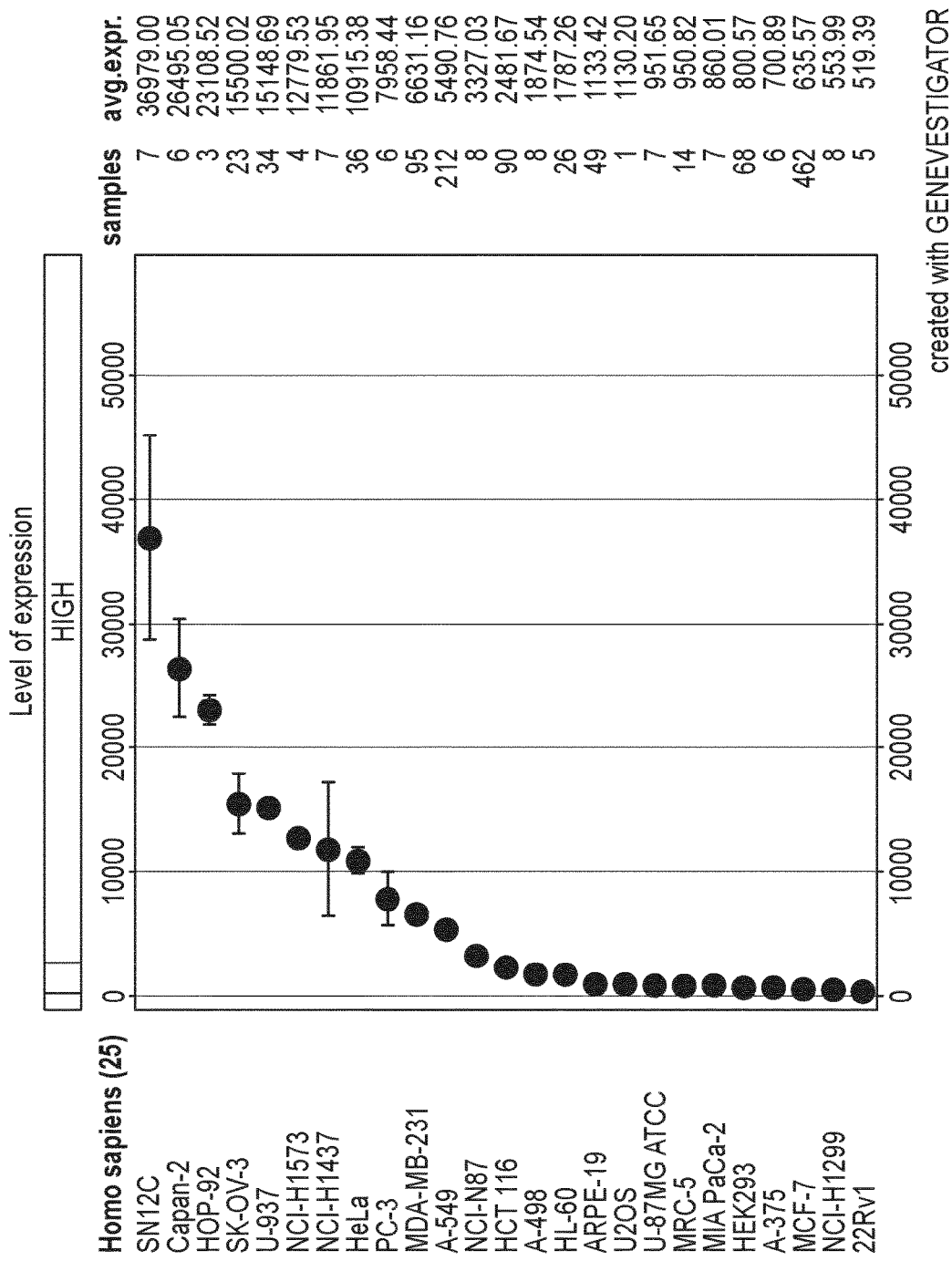

FIG. 12 shows the linear CDA expression levels in various cell lines. The expression levels were determined using the Affymetrix Human Genome U133 Plus 2.0 Array Platform and the Genevestigator database (https://genevestigator.com/gv/).

Figure 13A:
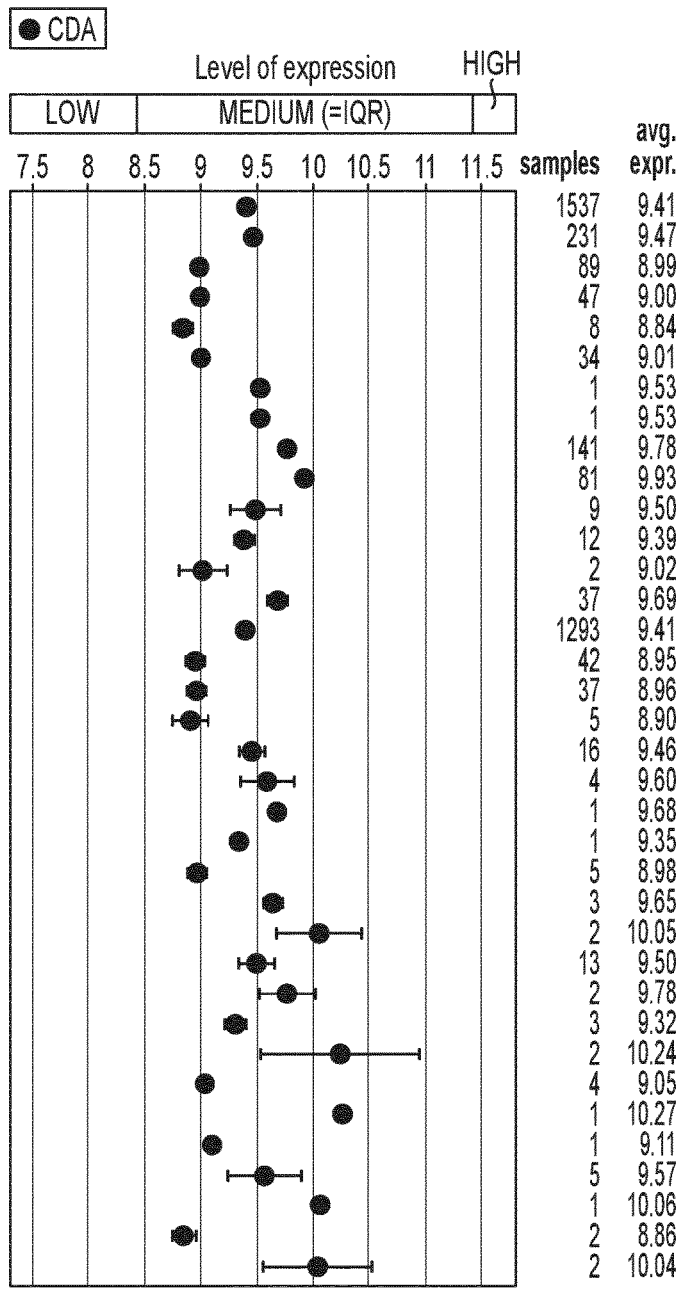
Figure 13B:
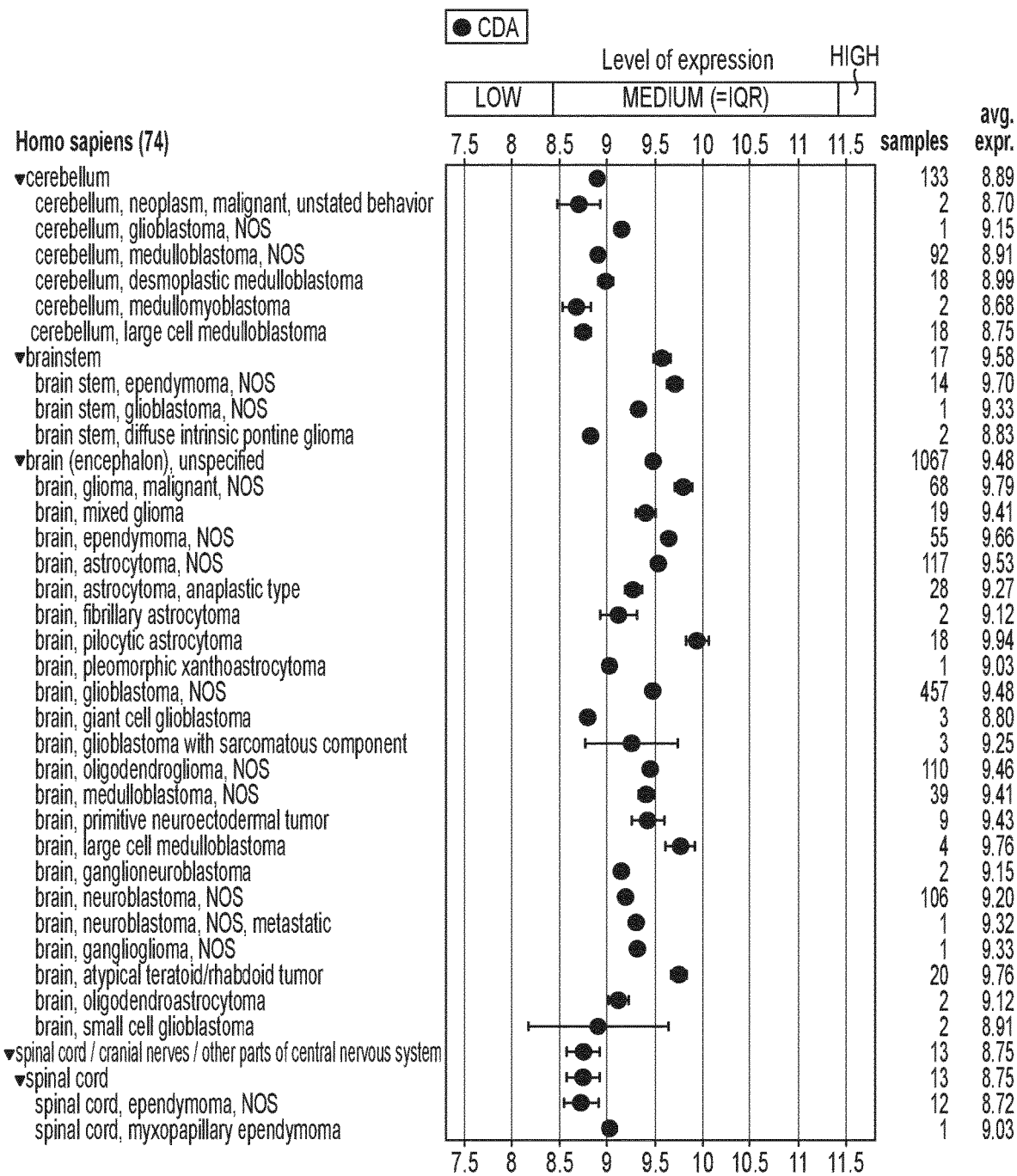

FIG. 13A and 13B show the CDA expression levels in various human brain tumours. The values are normalized Log 2 CDA expression levels. The expression levels were determined using the Affymetrix Human Genome U133 Plus 2.0 Array platform and the Genevestigator database (https://genevestigator.com/gv/).

Figure 14A:
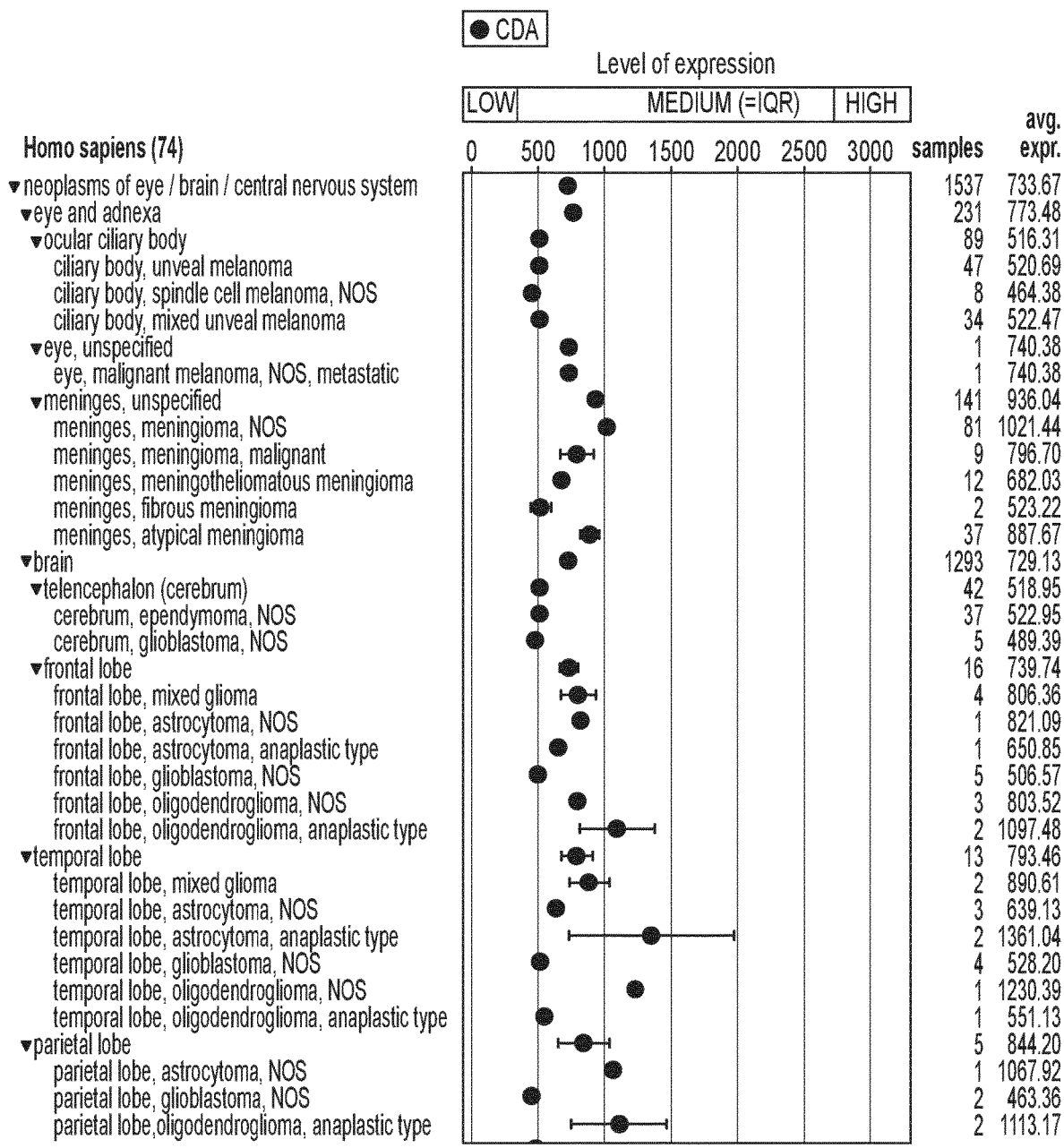
Figure 14B:
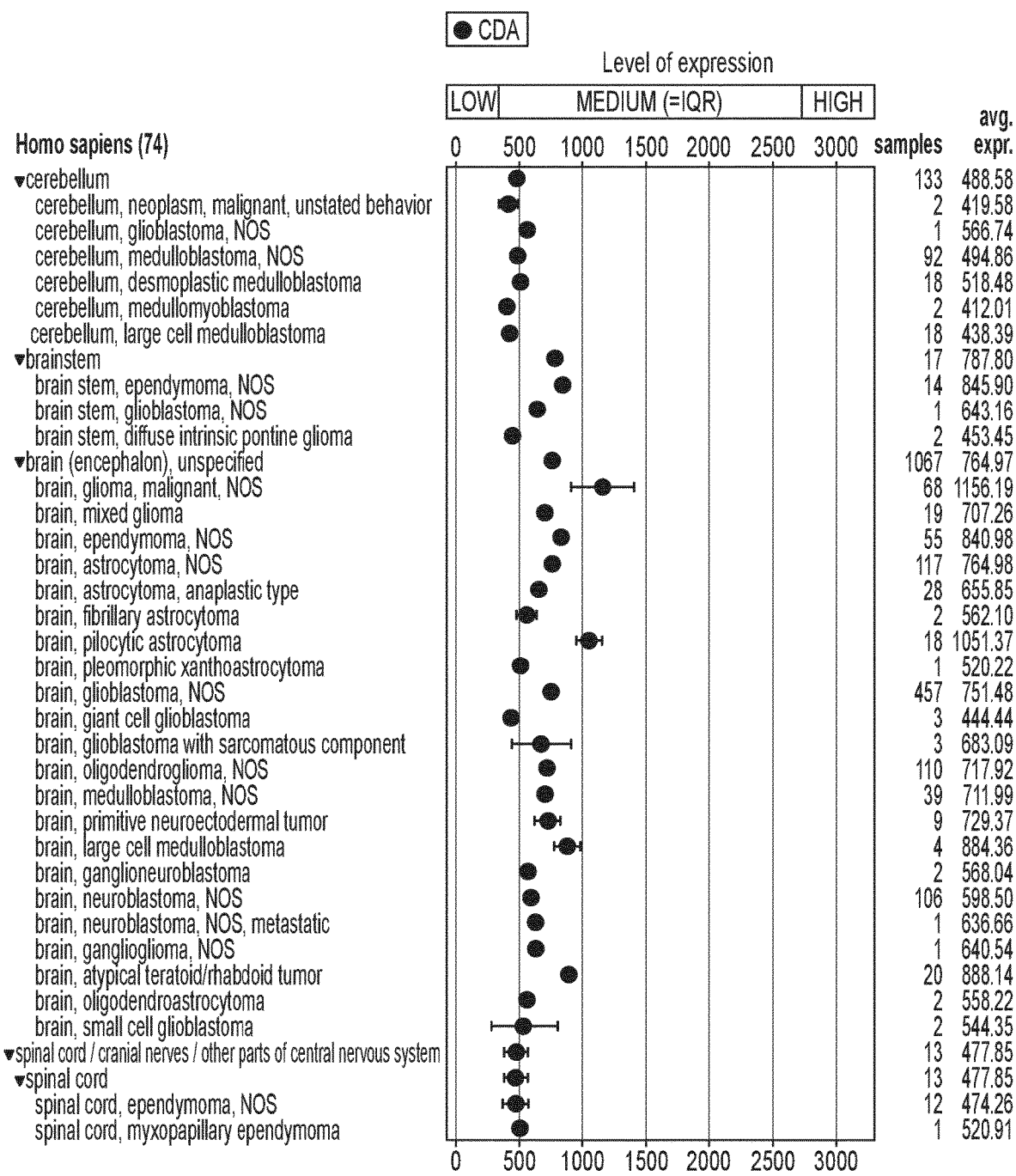

FIGS. 14A and 14B show the linear CDA expression levels in various human brain tumours. The expression levels were determined using the Affymetrix Human Genome U133 Plus 2.0 Array platform and the GENEVESTIGATOR® database (https://genevestigator.com/gv/).

Figure 15:
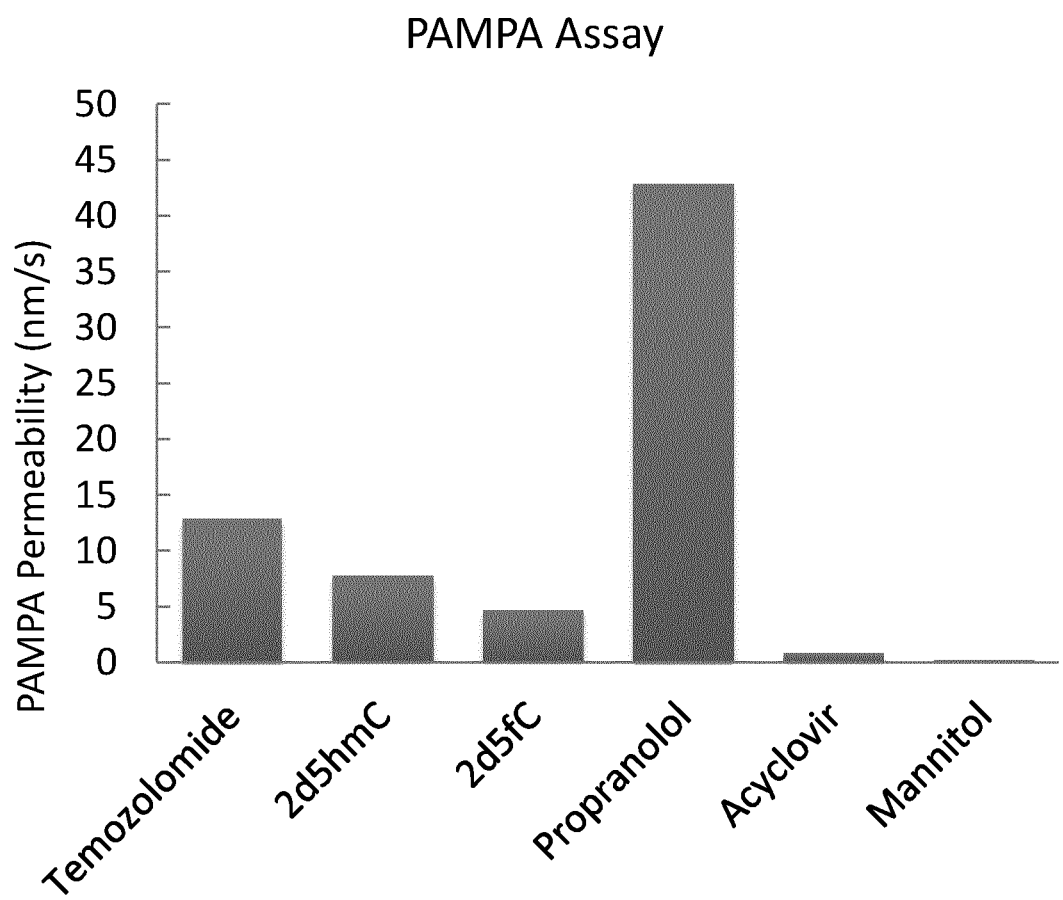

FIG. 15 shows the results of a PAMPA Assay demonstrating that 2d5hmC and 2d5fC can pass the blood-brain barrier.

EXAMPLES

Materials and Methods

Animals

All aspects of this work, including housing, experimentation, and disposal of animals were performed in general accordance with the Guide for the Care and Use of Laboratory Animals: Eighth Edition (National Academy Press, Washington, D.C., 2011) in an AAALAC-accredited laboratory animal facility. The animal care and use protocol was reviewed and approved by the IACUC at Pharmacology Discovery Services Taiwan, Ltd.

Cell Culture

Primary glioma neural stem (GNS) cells (G7, G14, G144, G166) were cultured on poly-D-lysine (Merck Millipore, Cat. Nr. A-003-E) and laminin (R&D Systems, Cat.Nr. 3446-005-01) coated plates in neural stem cell medium (50% DMEM-F12 (Thermofisher, Cat. Nr. 21041025), 50% neurobasal medium (Thermofisher, Cat. Nr. 10888-022), N2 (Life Technologies, Cat. Nr. A-003-E) and B27 supplements (Life Technologies, Cat.Nr. 12587010), 1 mM sodium pyruvate (Life Technologies, Cat.Nr. 11360-039), 2 mM glutamax (Life Technologies, Cat. Nr. 35050038), 1 mM HEPES (Fisher Scientific, Cat. Nr. BP299-1), 0.1 mM p-mercaptoethanol (Life Technologies, Cat. Nr. 31350010), 1× nonessential amino acids (Life Technologies, Cat. Nr. 11140-035), 0,006% bovine serum albumin (Sigma, Cat. Nr. A8577-10ML),4 µg/ml heparin (Sigma, Cat. Nr. H3149-25KU), 100 U/ml penicillin, 100 µg/ml streptomycin, 20 ng/ml hEGF (R&D Systems, Cat. Nr. 236-EG-200), 10 ng/ml bFGF (Peprotech, Cat. Nr. 100-18B).

HCoT16 were grown in McCoAs 5a Medium modified (Life technologies, Cat.Nr. 36600021) supplemented with 10% Fetal Bovine Serum and 100 U/mi penicillin 100 U/ml streptomycin.

Arpe 19 were grown in DMEM:F12 medium (Life Technologies, 21331-020) supplemented with 10% Fetal Bovine Serum and 100 U/m penicillin 100 U/m5 streptomycin.

HAP1 were grown in IMDM (Gibco, Cat. Nr. 12440-05) supplemented with supplemented with 10% Fetal Bovine Serum and 100 U/m penicillin 100 U/m5 streptomycin.

Cell lines not mentioned above were grown in DMEM (Sigma, Cat.Nr. 06429) supplemented with 10% Fetal Bovine Serum and 100 U/mA penicillin 100 U/m5 streptomycin. All cells were maintained in a 5% 002, humidified, water-jacketed incubator at 37° C. Cells were passed between 70 and 90% confluence.

Drugs

Compounds used in the present Examples were obtained as follows (CAT#0 catalogue number).

| Compound | CAS # | Source | CAT # |
| --- | --- | --- | --- |
| 5-hydroxymethyl-2'-deoxycytidine | 7226-77-9 | Berry and Associates | PY 7588 |
| 5-formyl-2'-deoxycytidine | 137017-45-9 | Berry and Associates | PY 7589 |
| 5-carboxyl-2'-deoxycytidine | 1009808-62-1 | Berry and Associates | PY 7593 |
| 5-formylcytidine | 148608-53-1 | Berry and Associates | PY 7599 |
| 5-formylcytosine | 4425-59-6 | Toronto Research Chemicals | F698975 |
| Temozolomide | 85622-93-1 | Sigma Aldrich | T2577 |
| 5-flurouracil | 51-21-8 | Sigma Aldrich | F6627 |
| 5-hydroxymethylcytidine | 19235-17-7 | Berry and Associates | PY 7596 |
| 5-hydroxymethylcytosine | 1123-95-1 | Toronto Research Chemicals | H945870 |
| 5-chloro-2'-deoxycytidine | 32387-56-7 | Carbosynth | NC08279 |
| 5-bromo-2'-deoxycytidine | 1022-79-3 | Carbosynth | NB06450 |
| 5-iodo-2'-deoxycytidine | 611-53-0 | Carbosynth | ND05777 |
| Thymidine | 50-89-5 | Sigma Aldrich | T1895 |
| 5-methoxymethyl-2'-deoxyuridine | 5116-22-3 | Toronto Research Chemicals | M263610 |
| 5-acetoxymethyl-2'-deoxyuridine | 148380-55-6 | Toronto Research Chemicals | A167180 |
| 5-formyl-2'-deoxycytidine-5'-triphosphate | | Trilink Biotech | N-2064 |
| 5-Hydroxymethyl-2'-deoxycytidine-5'-Triphosphate | | Trilink Biotech | N-2060 |

Survival Assay

In a 96-well plate, 4000 cells in 100 µl of corresponding medium were seeded. The following day, drugs, diluted in DMSO, were added in 8 concentrations in triplicate. Drugs were added as a 4-fold dilution series starting from 100 µM. Cells were incubated with the drugs for 72 hours. Cell proliferation was assessed by MTT assay according to the manufacturer's protocol (ATCC, Cat. Nr. 30-1010K). Cell survival was normalized to the survival of cells treated with DMSO only. Experiment was performed three times, data represent mean of nine wells±SEM.

MTD (Maximum Tolerated Dose)

5-hydroxymethyl-2'-deoxycytidine and 5-formyl-2'-deoxycytidine (Berry and Associates), were formulated in dimethyl sulfoxide (DMSO)/Solutol® R HS15/phosphate buffered saline (PBS) (5/5/90, v/v/v) at the concentration of 30 and 200 and 400 mg/mL for IP administration at the dosing volume of 5 mL/kg. A dosing volume at 10 or 20 mL/kg was applied.

Male ICR mice weighing 23±3 g were provided by BioLasco Taiwan (under Charles River Laboratories Licensee). Animals were acclimated for 3 days prior to use and were confirmed with good health. All animals were maintained in a hygienic environment with controlled temperature (20-24° C.), humidity (30%-70%) and 12 hours light/dark cycles. Free access to sterilized standard lab diet [MFG (Oriental Yeast Co., Ltd., Japan)] and autoclaved tap water were granted.

5-hydroxymethyl-2'-deoxycytidine and 5-formyl-2'-deoxycytidine were administered IP to groups of three male ICR mice weighing 23±3 g. Animals received an initial dose of 300 mg/kg. If the animals survived for 72 hours, the dose for the next cohort was increased. If one or more animals died, the dose for the next cohort was decreased. The testing stopped when all animals survived at the upper bound, or when three dose levels had been tested or when the upper or lower bound had been reached. At each dose level, animals were observed for the presence of acute toxic symptoms (mortality, convulsions, tremors, muscle relaxation, sedation, etc.) and autonomic effects (diarrhea, salivation, lacrimation, vasodilation, piloerection, etc.) during the first 30 minutes, again at 1, 24, 48 and 72 hours. Body weights were recorded pre-dose and at 72 hours. The animals were observed and mortality noted daily after compound administration. Gross necropsy was performed on all animals without tissue collection, and the next dose level was determined based on the study design table.

Multiple MTD 5-hydroxymethyl-2'-deoxycytidine and 5-formyl-2'-deoxycytidine (Berry and Associates) were formulated in dimethyl sulfoxide (DMSO)/Solutol® R HS15/phosphate buffered saline (PBS) (5/5/90, v/v/v) at the concentration of 15, 50, and 100 mg/mL for IP administration at the dosing volume of 20 mL/kg. The test compounds were dosed every three days for a total of 5 doses (q3d×5).

Male ICR mice weighing 23±3 g were provided by BioLasco Taiwan (under Charles River Laboratories Licensee). Animals were acclimated for 3 days prior to use and were confirmed with good health. All animals were maintained in a hygienic environment with controlled temperature (20-24° C.), humidity (30%-70%) and 12 hours light/dark cycles. Free access to sterilized standard lab diet [MFG (Oriental Yeast Co., Ltd., Japan)] and autoclaved tap water were granted.

Animals were observed for the presence of acute toxic symptoms (mortality, convulsions, tremors, muscle relaxation, sedation, etc.) and autonomic effects (diarrhea, salivation, lacrimation, vasodilation, piloerection, etc.) during the first 30 minutes after each treatment (Days 1, 4, 7, 10 and 13), and again at 1, 24, 48 and 72 hours after the final dose (Day 13). The mortality was noted at the same scheme. In addition, body weights were recorded before each treatment and at 24, 48 and 72 hours after the final administration. Gross necropsy was performed on all animals without tissue collection.

Xenograft 5-hydroxymethyl-2'-deoxycytidine and 5-formyl-2'-deoxycytidine (Berry and Associates) dosing solutions were prepared fresh prior to each dose administration by first adding appropriate volume of DMSO to pre-weighed compound, then adding appropriate volumes of Solutol® and PBS (5% DMSO/5% Solutol®/90% PBS). Standard agent, Temozolomide, was provided by Oslo University Hospital in powder form and was formulated fresh prior to each dose by first adding appropriate volume of DMSO to pre-weighed compound, then adding appropriate volumes of Solutol® and PBS (5% DMSO/5% Solutol®/90% PBS). 5-hydroxymethyl-2'-deoxycytidine and 5-formyl-2'-deoxycytidine were administered at a dose volume of 20 mL/kg. Standard agent, Temozolomide, was administered at a dose volume of 10 mL/kg.

The human brain malignant glioma cell line, U87-MG (ATCC HTB-14, epithelial glioblastoma), was obtained from American Type Culture Collection (ATCC). The cells were cultured in Minimum essential medium containing 5% fetal bovine serum (FBS) at 37° C., with 5% CO2 in an incubator.

Female (nu/nu) nude mice aged 6-7 weeks obtained from BioLasco Taiwan (under Charles River Laboratories Licensee) were used. The animals were housed in individually ventilated cages (IVC, 36 Mini Isolator system). The allocation for 5 animals was 27×20×14 in cm. All animals were maintained in a hygienic environment under controlled temperature (20-24° C.) and humidity (30%-70%) with 12-hour light/dark cycle. Free access to standard lab diet [MFG (Oriental Yeast Co., Ltd., Japan)] and autoclaved tap water were granted.

Viable U87-MG (ATCC HTB-14) cells were subcutaneously (SC) implanted (5×10<sup>6</sup> cells/mouse in PBS at 0.2 mL/mouse) into the right flank of female nu/nu mice.

When group mean tumor volumes reached approximately 129 mm$^3$ to 131 mm$^3$, tumor implanted mice were divided into four treatment groups, each group containing eight animals, and dose administrations were initiated (denoted as Day 1).

5-hydroxymethyl-2'-deoxycytidine, 5-formyl-2'-deoxycytidine at 2000 mg/kg and corresponding vehicle (5% DMSO/5% Solutol®/90% PBS) were administered intraperitoneally (IP) once every three days for a total of five administrations. Temozolomide at 40 mg/kg was administered orally (PO) once daily for five total administrations.

The tumor volume, body weight, mortality, and signs of overt toxicity were monitored and recorded twice weekly for 29 days. Tumor volume (mm$^3$) was estimated according to the ellipsoid formula as: length×(width)$^2$×0.5. Tumor growth inhibition (T/C) was calculated by the following formula:

$$\% \, T/C = (Tn/Cn) \times 100\%$$

Cn: Tumor weight measured on Day n in the control group
Tn: Tumor weight measured on Day n in the treated group
% T/C value≤42% was considered significant antitumor activity (#).

Percent tumor growth inhibition (TGI) was also calculated by the following formula:

$$\% \, THI = (1 - (Tn/Cn)) \times 100\%$$

% TGI value≥58% was considered significant antitumor activity (#).

Two-way ANOVA® followed by Bonferroni test was also used to ascertain the statistically significant difference compared to the negative control group during study; Day 1 through to Day 29. Differences are considered significant at p<0.05 (*).

Upon study completion, tumors were excised from all animals on study and photographs were taken.

HPRT Assay

HPRT mutagenicity assay was performed in V79 cells. 50,000 V79 cells were treated with three different concentrations of either d5hmC or d5fC (1, 10, 100 μM) for 24 hours in a 6 well plate. DMSO was used as a negative control. After the treatment, the cells were subcultured as needed in T75 flasks for 9 days to allow expression of HPRT-mutants. 10,000 cells were replated into 10 replica Petri dishes (100×15 mm) with selective media (2.5 μg/ml of 6TG).

Survival (relative plating efficiency) was determined by plating 200 cells into four replica Petri dishes (60×15 mm) without selective media. Colonies were fixed, Giemsa-stained and counted 7 days later. The mutant frequency is expressed as a total number of mutants counted on all plates divided by the number of cells seeded corrected by reseeding plating efficiency. Experiment was performed three times, data represent mean of triplicate±SEM.

Apoptosis Flow Cytometry 100,000 cells were seeded in a 6-well plate and incubated with 100 μM of Temozolomide, 2'-Deoxy-5-hydroxymethylcytidine, 5-Formyl-2'-deoxycytidine or DMSO for 72 hours. Detection of apoptotic cells was assessed using Annexin V-7-amino-actinomycin D (7-AAD) Apoptotic Detection Kit (Nordic Biosite AS, Cat. Nr. 640922) according to manufacturer's protocol.

Fluorescence-activated cell sorting analysis was performed on LSR Fortessa (BD Biosciences) and data were analyzed on FlowJo software. All experiments were performed in triplicates.

Western Blots

Western blots were performed as previously described (Towbin et al., 1979. *Biotechnology*, 24, 145-149). Anti-CDA antiserum (Abcam, cat nr. Ab82346) was used according to the manufacturer's recommended concentration. Proteins were quantified by the signal generated by the oxidation of luminol by horse radish peroxidase conjugated to the secondary antibody.

Example 1: Cytotoxicity to Tumour Cells

HeLa cells, grown as described above (Materials and Methods), were treated with 5-hydroxymethyl-2'-deoxycytidine and 5-formyl-2'-deoxycytidine. After three days of treatment with these compounds, cell survival was assessed as described above (Materials and Methods). While survival after treatment with 5-hydroxymethyl-2'-deoxycytidine did not differ from DMSO treated cells, it was found, surprisingly, that 5-formyl-2'-deoxycytidine was cytotoxic to HeLa cells.

The cytotoxic effect of that 5-formyl-2'-deoxycytidine was compared to two well-described cytotoxic compounds, 5-flurouracil and temozolamide. 5-formyl-2'-deoxycytidine was determined to be more cytotoxic to HeLa (IC50=0.76 μM) cells than both 5-flurouracil (IC50>25 μM) and temozolomide (IC50>25 μM).

With the knowledge that 5-formyl-2'-deoxycytidine is cytotoxic to cervical carcinoma (HeLa) cells, the study was expanded in two directions: (i) a further compound was assessed: 5-carboxyl-2'-deoxycytidine; and (ii) their cytotoxic effects against a wide range of human cancer cell lines was assessed (Table 1).

TABLE 1

Evaluation of 5-formyl-2'-deoxycytidine (2d5fC), 5-hydroxymethyl-2'-deoxycytidine (2d5hmc) and 5-carboxy-2'-deoxycytidine (2d5caC) in a range of human cancer cell lines, and as compared to Temozolomide and 5-flurouracil (5fU). $IC_{50}$ is the concentration at which half of the cells are killed by the relevant compound.

| Cell Line | Disease | Germ Layer | $IC_{50}$ (μM) | | | | |
| --- | --- | --- | --- | --- | --- | --- | --- |
| | | | 2d5fC | 2d5hmC | 2d5caC | Temozolomide | 5fU |
| U87-MG | Glioma, Grade IV | Ectoderm | 0.3340 | 3.027 | >25.00 | >25.00 | >25.00 |
| HCT-116 | Colon Carcinoma | Endoderm | >25.00 | >25.00 | >25.00 | >25.00 | 3.545 |
| A549 | Lung Carcinoma | Endoderm | >25.00 | >25.00 | >25.00 | 1.018 | 1.853 |
| 22Rv1 | Prostate Carcinoma | Endoderm | >25.00 | >25.00 | >25.00 | >25.00 | >25.00 |
| NCI-N87 | Gastric Carcinoma | Endoderm | 0.8057 | >25.00 | >25.00 | >25.00 | 1.524 |
| MIA PaCa-2 | Pancreatic | Endoderm | 1.143 | >25.00 | >25.00 | >25.00 | 8.096 |
| A-498 | Kidney Carcinoma | Mesoderm | >25.00 | >25.00 | >25.00 | >25.00 | 2.367 |
| U937 | Lymophoma | Mesoderm | 0.9536 | >25.00 | >25.00 | 13.08 | 7.449 |
| A375 | Malignant Melanoma | Mesoderm | 3.188 | >25.00 | >25.00 | >25.00 | 7.867 |
| HL-60 | Acute Promyelocytic Leukemia | Mesoderm | 6.262 | >25.00 | >25.00 | >25.00 | >25.00 |
| SK-OV-3 | Ovarian Adenocarcinoma | Mesoderm | 9.690 | >25.00 | >25.00 | >25.00 | 3.756 |
| MCF-7 | Epithelial Adenocarcinoma (Breast) | Mesoderm | 0.8657 | >25.00 | >25.00 | >25.00 | >25.00 |
| U2OS | Bone | Mesoderm | 8.69 | >25.00 | >25.00 | >25.00 | 2.889 |
| HeLa | Cervical Adenocarcinoma | Mesoderm | 0.76 | >25.00 | >25.00 | >25.00 | >25.00 |
| HAP1 | Chronic Myelogenous Leukemia (CML) | Mesoderm | >25.00 | 6.53 | n.d. | n.d. | n.d. |
| V79 | Chinese Hamster Ovary | Mesoderm | >25.00 | >25.00 | n.d. | n.d. | n.d. |
| H1437 | Lung (metastatic non-small cell adenocarcinoma) | Endoderm | 5.65 | n.d. | n.d. | n.d. | n.d. |
| H1573 | Lung (metastatic adenocarcinoma) | Endoderm | 7.72 | n.d. | n.d. | n.d. | n.d. |

As shown in Table 1, 5-carboxyl-2'-deoxycytidine had no cytotoxic properties in any of the cancer cell lines evaluated. Interestingly, 5-formyl-2'-deoxycytidine is cytotoxic to a wide range of human cancer cells, indicating its potential use in the treatment of a wide range of cancers. 5-hydroxymethyl-2'-deoxycytidine has a narrower cytotoxicity profile; indeed this cytidine derivative was only cytotoxic to two cell lines evaluated: U87-MG, grade IV glioma cells (IC50>0.3340 µM) and HAP1 Chronic Myelogenous Lukemia cells (IC50>3.027 µM). This suggests that this compound may be well tolerated by patients. 5-formyl-2'-deoxycytidine and 5-hydroxymethyl-2'-deoxycytidine were observed as the most cytotoxic to glioblastoma multiforme cell (U87-MG) lines.

Since the greatest cytotoxic effect of 5-formyl-2'-deoxycytidine and 5-hydroxymethyl-2'-deoxycytidine was observed in glioma grade IV (U87-MG) cells, the cytotoxic activity of these compounds was evaluated in a wider range of patient derived grade IV, glioma cells (Table 2). Due to lack of activity in previous assays, 5-carboxyl-2'-deoxycytidine was not included in this more rigorous analysis.

TABLE 2

Evaluation of cytotoxicity of 5-formyl-2'-deoxycytidine (2d5fC) and 5-hydroxymethyl-2'-deoxycytidine (2d5hmc) against patient derived glioblastoma multiforme cell lines (Glioma, Grade IV), and as compared to Temozolomide and 5-flurouracil (5fU). $IC_{50}$ is the concentration at which half of the cells are killed by the relevant compound.

| Cell Line | Disease | Germ Layer | $IC_{50}$ (µM) | | | |
|---|---|---|---|---|---|---|
| | | | 2d5fC | 2d5hmC | Temozolomide | 5fU |
| U87-MG | Glioma, Grade IV | Ectoderm | 0.3340 | 3.027 | >25.00 | >25.00 |
| G7 | Glioma, Grade IV | Ectoderm | 19.25 | 11.93 | 6.176 | 6.456 |
| G14 | Glioma, Grade IV | Ectoderm | >100 | 25.4 | 6.018 | 11.61 |
| G26 | Glioma, Grade IV | Ectoderm | 28.12 | >100 | 7.338 | 7.125 |
| G30 | Glioma, Grade IV | Ectoderm | 18 | 28.13 | 21.6 | 23.33 |
| G144 | Glioma, Grade IV | Ectoderm | >100 | >100 | 14.66 | 6.805 |
| G166 | Glioma, Grade IV | Ectoderm | >100 | >100 | >100 | 4.813 |
| SF188 | Glioma, Grade IV | Ectoderm | 28.24 | 8.975 | >100 | 3.884 |
| U3017 | Glioma, Grade IV | Ectoderm | >100 | 14.12 | >100 | 3.921 |
| DIPG007 | Glioma, Grade IV | Ectoderm | >100 | >100 | >100 | 4.302 |
| U3013 | Glioma, Grade IV | Ectoderm | >100 | >100 | >100 | 4.138 |
| CB152 | Glioma, Grade IV | Ectoderm | >100 | >100 | >100 | 6.496 |

As shown in Table 2, after treatment with the relevant compound, 5 of 12 Grade IV, Glioma cell lines were killed by 5-formyl-2'-deoxycytidine and 6 of 12 Grade IV, Glioma cell lines were killed by 5-hydroxymethyl-2'-deoxycytidine. This indicates the ability of these compounds against a broad range of Gliomas. These results were benchmarked to both temozolomide, the current frontline treatment for Grade IV, Gliomas, and 5-flurouracil, a broad use anti-cancer drug. Temozolomide effectively killed 5 of 12 Glioma, Grade IV cell lines and 5-flurouracil killed 11 of 12 Glioma, Grade IV cell lines. Thus, the data demonstrates that 5-formyl-2'-deoxycytidine is as effective as the current frontline treatment for Grade IV, Gliomas and that 5-hydroxymethyl-2'-deoxycytidine is more effective than the current frontline treatment for Grade IV, Gliomas.

Furthermore, Table 2 demonstrates that both 5-formyl-2'-deoxycytidine and 5-hydroxymethyl-2'-deoxycytidine are cytotoxic to cell lines that are resistant to the current frontline treatment (Temozolomide). This provides evidence that these compounds may perform better than current treatments for such Temozolomide resistant tumours. Alternatively, Table 2 indicates that temozolomide in combination with 5-formyl-2'-deoxycytidine and/or 5-hydroxymethyl-2'-deoxycytidine would be an optimal treatment.

Example 2: Cytotoxicity to Normal Cells

As demonstrated in Example 1, 5-formyl-2'-deoxycytidine and 5-hydroxymethyl-2'-deoxycytidine are useful therapeutics for the treatment of cancers, particularly Grade IV gliomas, and particularly those that are resistant to temozolomide treatment.

The present inventors further investigated the extent to which these compounds kill normal human cells; low cytotoxicity against normal human cells is advantageous property for anti-cancer agents. The cytotoxicity of these compounds in various normal human cell lines was therefore investigated (Table 3). Cells were grown and the survival assay was performed as described above (Materials and Methods).

TABLE 3

Evaluation of cytotoxicity of 5-formyl-2'-deoxycytidine (2d5fC) and 5-hydroxymethyl-2'-deoxycytidine (2d5hmC) to normal (non-cancerous) human cell lines,), and as compared to Temozolomide and 5-flurouracil (5fU). IC$_{50}$ is the concentration at which half of the cells are killed by the relevant compound.

| Cell Line | Disease | Germ Layer | IC$_{50}$ (µM) 2d5fC | 2d5hmC | Temozolomide | 5fU |
|---|---|---|---|---|---|---|
| HEK293FT | Normal | Mesoderm, Kidney | >25.00 | >25.00 | >25.00 | |
| Arpe19 | Normal | Ectoderm, ReMna | >25.00 | >25.00 | >25.00 | >25.00 |
| HaCat | Normal | Mesoderm, KeraMnocyte | 0.1024 | >25.00 | >25.00 | 0.5228 |
| MRC5 | Normal | Endoderm, Lung | >25.00 | >25.00 | >25.00 | >25.00 |
| Buffy A | Normal | Mesoderm, Bone Marrow | >25.00 | >25.00 | n.d. | >25.00 |
| Buffy C | Normal | Mesoderm, Bone Marrow | >25.00 | >25.00 | n.d. | >25.00 |
| Buffy M | Normal | Mesoderm, Bone Marrow | >25.00 | >25.00 | n.d. | >25.00 |

As shown in Table 3, 5-hydroxymethyl-2'-dexycytidine was not cytotoxic to any of the normal cell lines evaluated. 5-formyl-2'-deoxycytidine was cytotoxic only to one normal human cell line (HaCat, Keratinocytes). These results indicate that these compounds are not only effective cancer chemotherapeutics but also can be well tolerated by humans.

Example 3: Maximum Tolerated Dose

Figure 1:
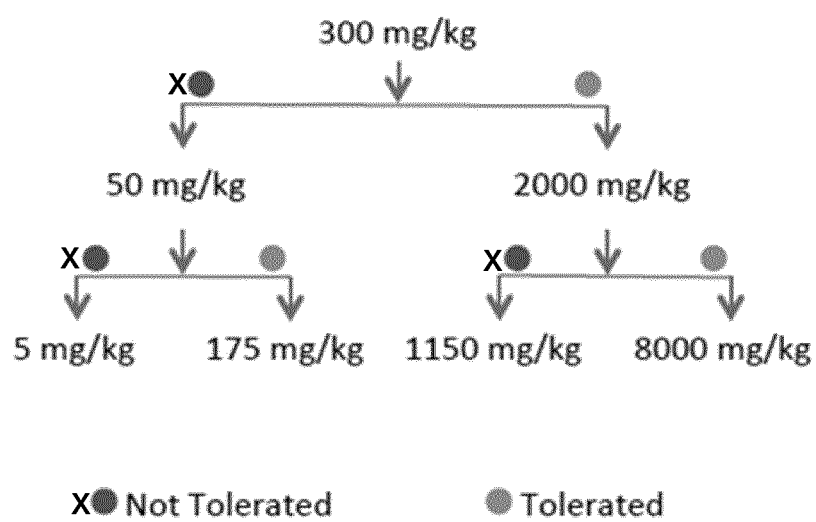
Figure 1:
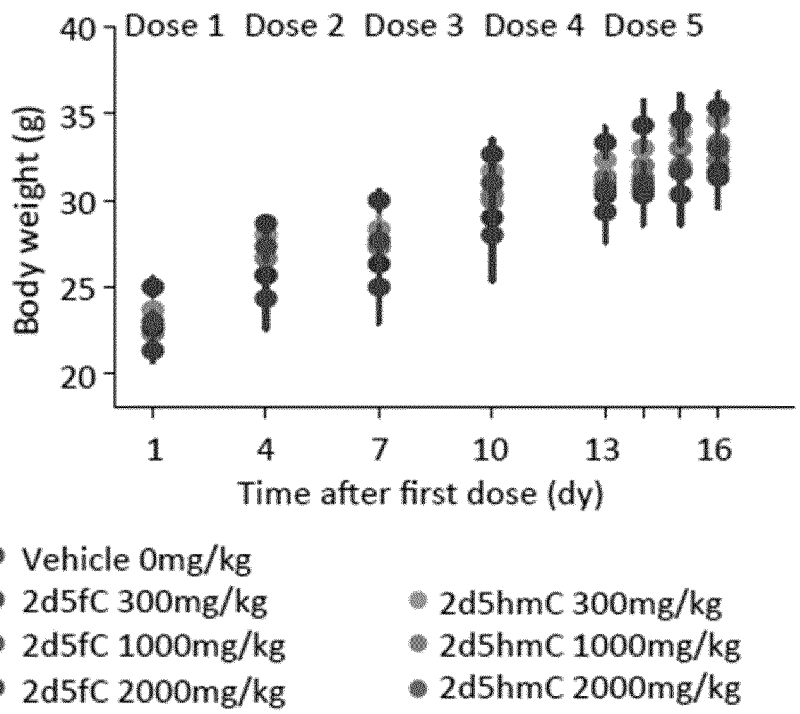
Figure 1:
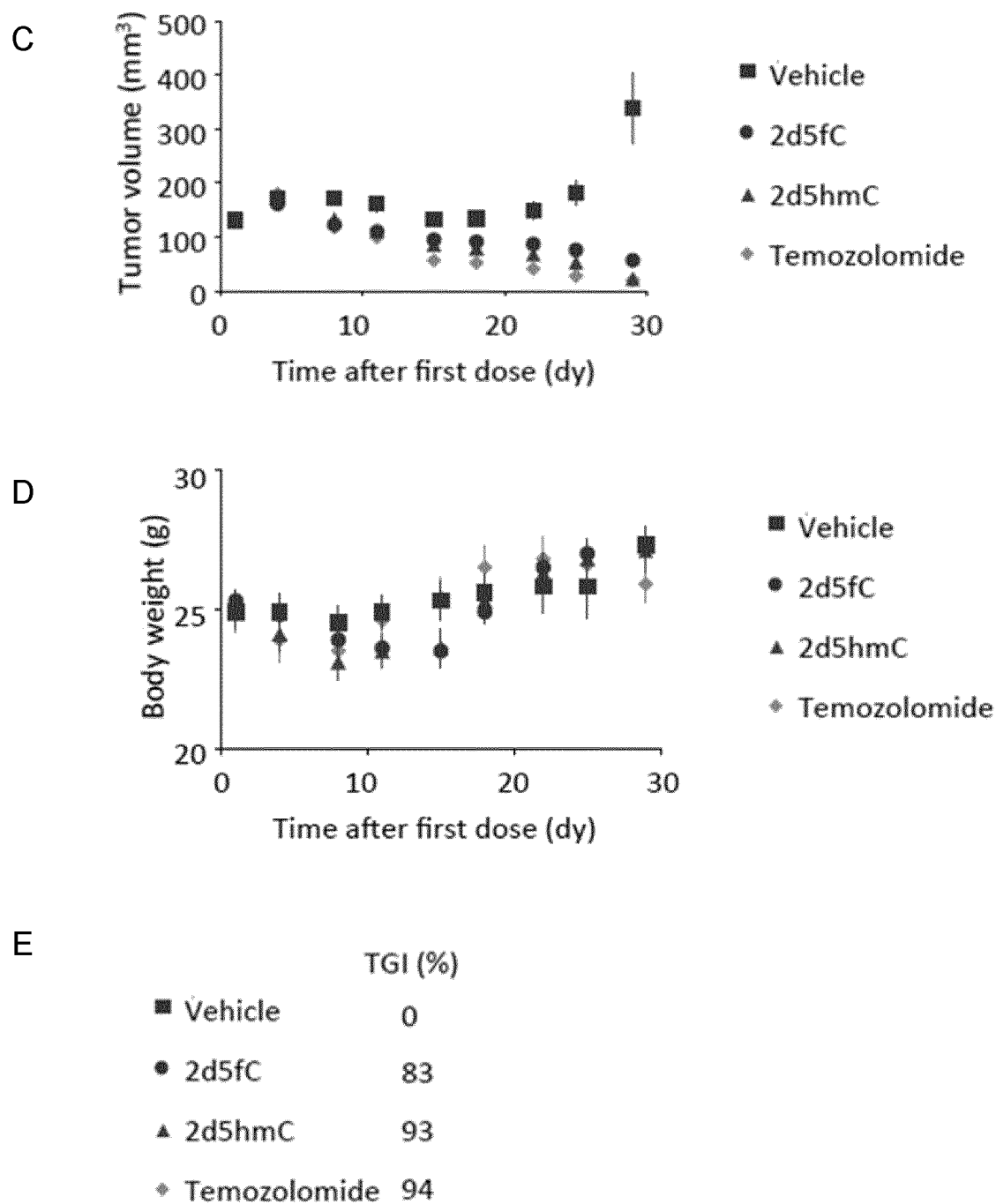
Figure 1:
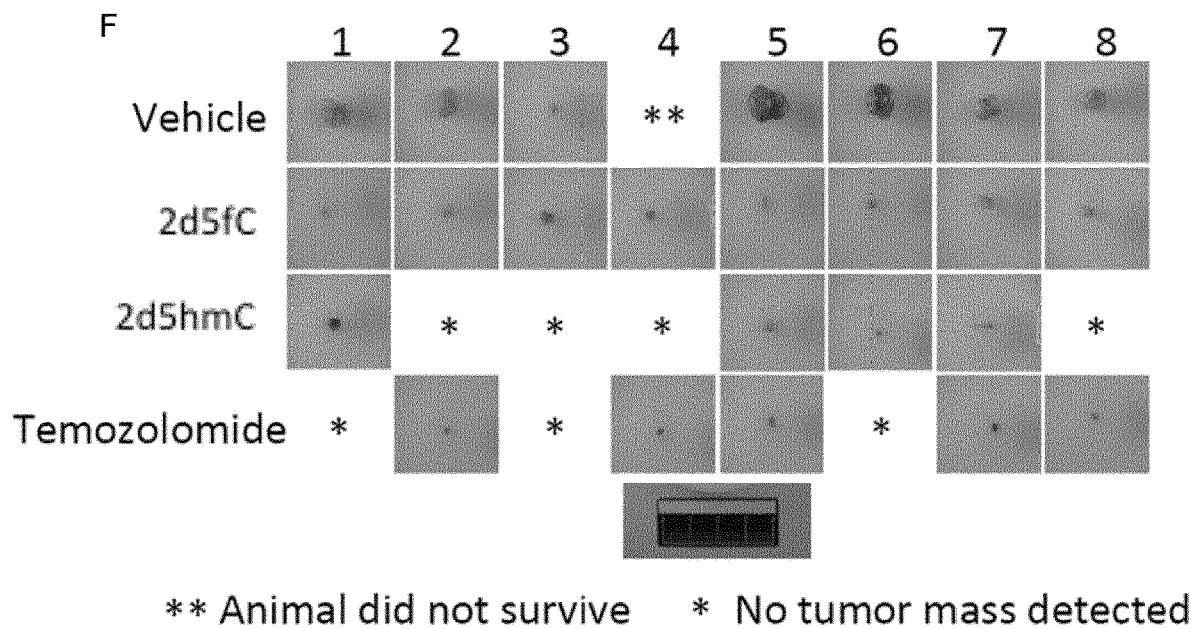
Figure 1:
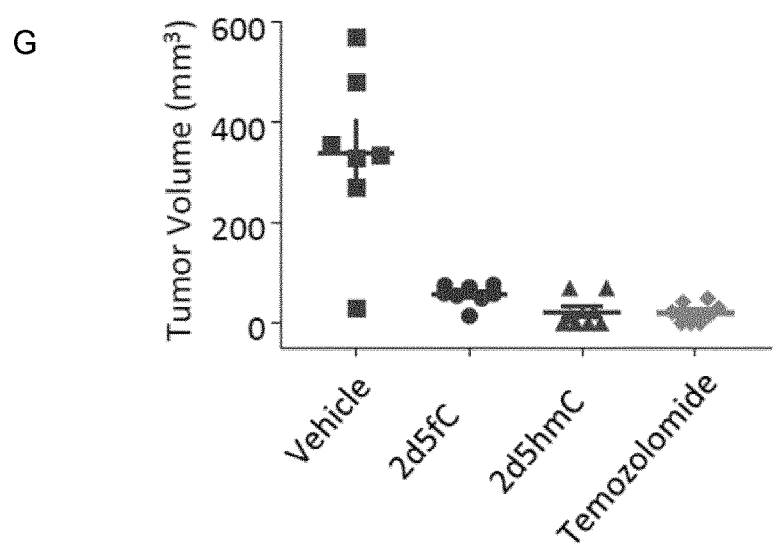
Figure 1:
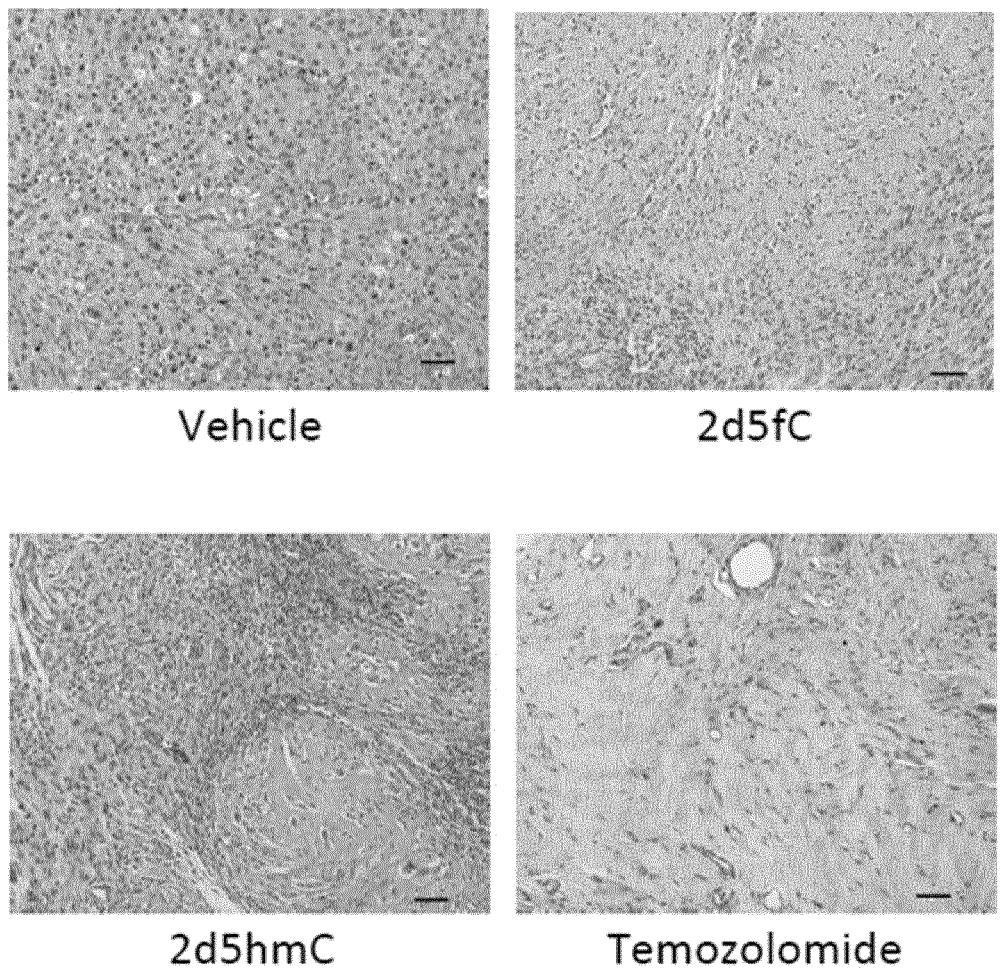

Since 5-hydroxymethyl-2'-dexycytidine and 5-formyl-2'-deoxycytidine have limited effects on normal cells, the present inventors considered that the compounds could be given at relatively high doses without causing side effects normally associated with cancer chemotherapy. The maximum tolerated dose (MTD) of these compounds in mice was determined as described above (Materials and Methods). An MTD scheme was developed (FIG. 1A). While the end-point of the study was survival after 72 hours, the presence of acute toxic symptoms (mortality, convulsions, tremors, muscle relaxation, sedation, etc.) and autonomic effects (diarrhea, salivation, lacrimation, vasodilation, piloerection, etc.) in the animals was monitored during the first 30 minutes, and again at 1, 24, 48 and 72 hours. Body weights were recorded pre-dose and at 72 hours.

The results indicated that mice can tolerate a single dose of 300 mg/kg and 2000 mg/kg of 5-formyl-2'-dexycytidine and 5-hydroxymethyl-2'-deoxycytidine. Mice were unable to tolerate a single dose of 8000 mg/kg 5-formyl-2'-deoxycytidine or 5-hydroxymethyl-2'-deoxycytidine (not shown). These results suggest that in mice the maximum tolerated single dose of both 5-formyl-2'-deoxycytidine and 5-hydroxymethyl-2'-deoxycytidine is at least 2000 mg/kg but less than 8000 mg/kg.

The conversion between a mouse dose and a human dose is a factor of 0.081 (Nair et al., (2016) *Basic Clin Pharm.* 7(2): 27-31. The data therefore indicates that in humans, the maximum tolerated single dose of the compounds of Formula (I) is at least 162 mg/kg but less than 648 mg/kg.

Cancer chemotherapeutic drugs that can be tolerated after multiple repetitive doses over many days are advantageous. Therefore, the present inventors conducted a repeated maximum tolerated dose evaluation for both 5-formyl-2'-deoxycytidine and 5-hydroxymethyl-2'-deoxycytidine as described above (Materials and Methods). As they were well tolerated as a single dose in both treatment groups, 300 mg/kg, 1000 mg/kg, and 2000 mg/kg doses were selected for repeated multiple tolerated dose evaluation.

Mice were injected with the indicated compound at the indicated dose intraperitoneally once every three days for a total of 5 doses. While survival was an end-point of this study, the primary end-point of the study was body weight; the presence of acute toxic symptoms (mortality, convulsions, tremors, muscle relaxation, sedation, etc.) and autonomic effects (diarrhea, salivation, lacrimation, vasodilation, piloerection, etc.) in the animals was also monitored during the first 30 minutes, again at 1, 24, 48 and 72 hours. Body weights were recorded pre-dose and at 72 hours.

Body weight in untreated animals was not statistically different from animals treated with either 5-formyl-2'-deoxycytidine or 5-hydroxymethyl-2'-deoxycytidine at any dose evaluated (FIG. 1B). These results indicate that these compounds are well tolerated at the indicated doses over extended periods of time.

Example 4: In Vivo Cytotoxicity 5-formyl-2'deoxycytidine and 5-hydroxymethyl-2'-deoxycytidine were evaluated in a Glioblastoma Multiforme mouse xenograft model as described above (Materials and Methods). U87-MG cells were injected subcutaneously into the flank of nude mice. Tumours were allowed to form as described above (Materials and Methods). After the tumours reached between 129 mm$^3$ and 131 mm$^3$ animals were divided into 4 groups—two treatment groups, a negative control group and a positive control group. The two treatment groups were 5-formyl-2'-deoxycytidine and 5-hydroxymethyl-2'-deoxycytidine. Mice in the treatment groups received one 2000 mg/kg dose of either 5-formyl-2'-deoxycytidine or 5-hydroxymethyl-2'-deoxycytidine every three days for a total of 5 doses. The negative control group was treated identically to the treatment group except the IP injection contained vehicle and no compound. The positive control group was treated with 5 daily doses of 40 mg/kg temozolomide.

The tumour volume (FIG. 1C), body weight (FIG. 1D), mortality, and signs of overt toxicity were monitored and recorded twice weekly for 29 days. Tumour volume (mm$^3$) was estimated according to the ellipsoid formula as: length× (width)$^2$×0.5. Percent tumour growth inhibition (% TGI) was determined using the following formula: % TGI=(1−[(Tn)/(Cn)])×100, where Tn=mean tumour volume of treated group on day "n", and Cn=mean tumour volume of control group on day "n". A % T/C value≤42% or a percent TGI value≥58% compared to that of the negative control group was considered significant anti-tumour activity. Two-way ANOVA® followed by Bonferroni test was also used to ascertain the statistically significant difference compared to the negative control group during the study; Day 1 through to Day 29 (*p<0.05).

FIG. 1C indicates that treatment with 5-formyl-2'-deoxycytidine or 5-hydroxymethyl-2'-deoxycytidine resulted in marked decrease in tumour volume, comparable to that achieved with Temozolomide, over all time points.

At the end of the study, both 5-formyl-2'-deoxycytidine and 5-hydroxymethyl-2'-deoxycytidine showed significant anti-tumour activity, 83% and 93% TGI respectively (FIG. 1E). The positive control group treated with temozolomide showed 94% TGI. All the compounds were well tolerated by the mice and no significant changes in body weight were observed as a result of the treatment (FIG. 1D). At the completion of this study tumours were dissected from the mouse and photographed (FIG. 1F) and measured (FIG. 1G); marked cytotoxic effects were observed with both of the treated groups.

One mouse in the control group died during this experiment the tumour volume of this mouse was not reported on day 29; however, tumour volumes of this mouse are included for the prior days.

Together, these surprising results demonstrate that 5-formyl-2'-deoxycytidine and 5-hydroxymethyl-2'-deoxycytidine efficiently kill Glioblastoma Multiforme cells (Glioma, Grade IV) and are not strongly cytotoxic to normal cells. Furthermore, these compounds are well tolerated in mice, and achieve marked reduction in tumour volume with minimal side effects in mice. The results demonstrate that the compounds of the invention can be used to treat human cancers, and they can be used at high doses to kill tumour cells without killing non-cancerous cells. Thus, there is a wide therapeutic window for the use of these compounds as anti-cancer drugs.

Example 5: Cytotoxic Vs. Cytostatic Effect

Figure 2:
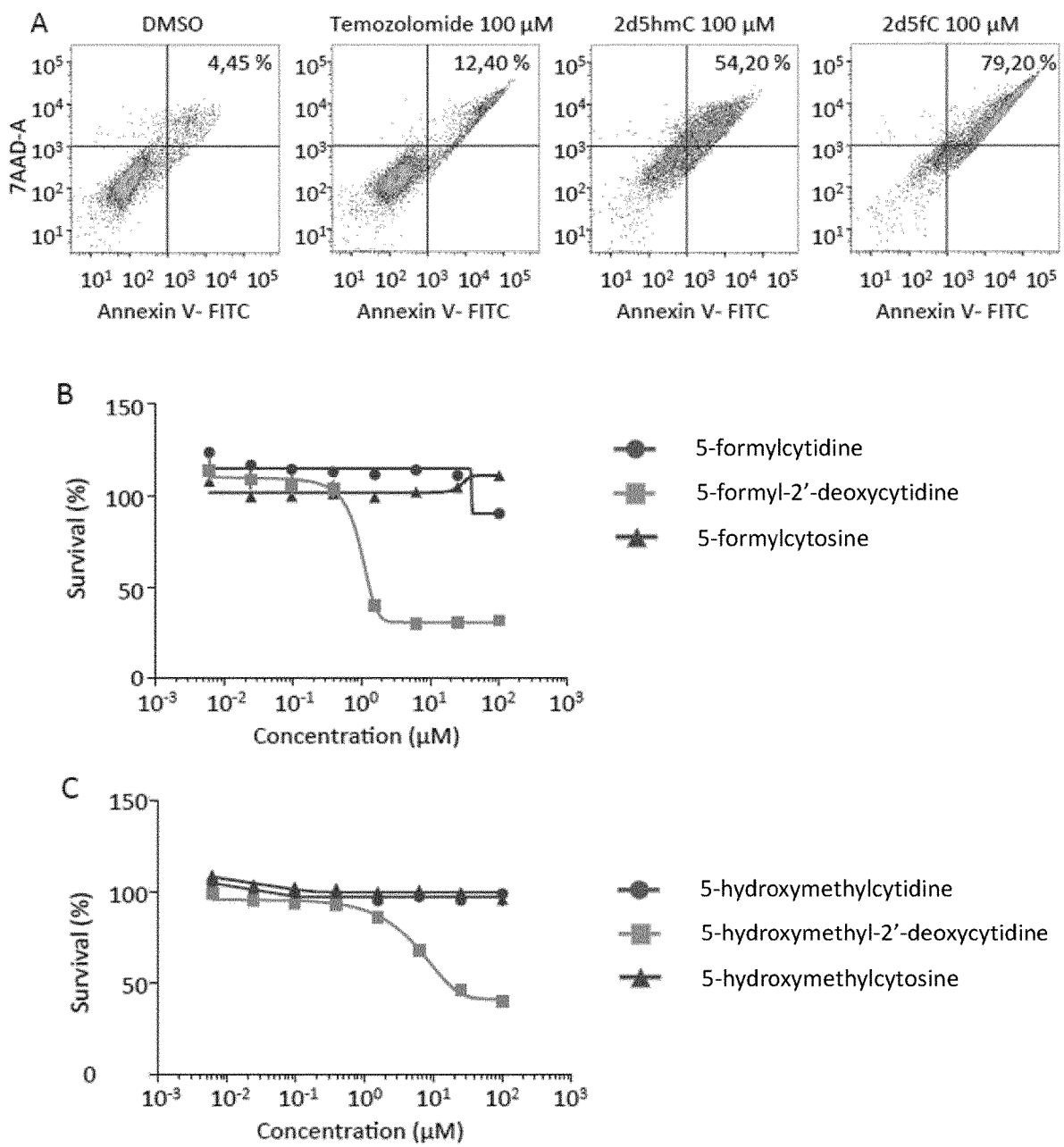

The above cell line assays measure metabolic activity, and as such do not distinguish between inhibition of cell division and cell death. It was therefore evaluated whether 5-formyl-2'deoxycytidine and 5-hydroxymethyl-2'-deoxycytidine were killing sensitive cells or causing them to be delayed in the cell cycle. SF-188 grade IV glioma cells were treated either with DMSO, temozolomide, 5-formyl-2'-deoxycytidine, or 5-hydroxymethyl-2'-deoxycytidine at the indicated concentration. Cells were harvested and stained with Annexin V (detects apoptotic cells by its ability to bind to phosphatidylserine) and 7AAD (a DNA stain which does not readily pass through intact cell membranes; cells with compromised membranes will therefore be selectively stained) and analyzed by flow cytometery as described above (Materials and Methods). SF-188 cells treated with DMSO or temozolomide yielded similar cytometric profiles with a slight increase in the amount of dead cells in the temozolomide treated control. A majority of SF-188 cells treated with 5-formyl-2'-deoxycytidine or 5-hydroxymethyl-2'-deoxycytidine were dead according to the flow cytometry profile (FIG. 2A). It is clear that SF188 cells exposed to 5-formyl-2'-deoxycytidine or 5-hydroxymethyl-2'-deoxycytidine are dead and not arrested at a cell cycle checkpoint.

Example 6: Requirement for 2'-Deoxy Sugar Derivatives 5-flurouracil, a widely used cancer chemotherapeutic drug, has multiple variants that are cytotoxic; these variants include the nucleoside (5-flurouridine and 5-fluro-2'-deoxyuridine) and nucleobase 5-flurouracil. The present inventors evaluated whether the ribonucleoside and nucleobase variants of 5-formyl-2'-deoxycytidine and 5-hydroxymethyl-2'-deoxycytidine would also be cytotoxic.

As shown in Table 1, 5-formyl-2'-deoxycytidine is cytotoxic to HeLa cells. The cytotoxicity of 5-formylcytidine and 5-formylcytosine in HeLa cells was evaluated in a survival assay as described above. Surprisingly, and in contrast to 5-fluorouridine and 5-fluorouracil, neither 5-formylcytidine nor 5-formylcytosine was cytotoxic to HeLa cells (FIG. 2B).

Table I shows that 5-hydroxymethyl-2'-deoxycytidine is cytotoxic to U87-MG cells. Cytotoxicity of the 5-hydroxymethylcytidine and 5-hydroxymethylcytosine in U87-MG cells was evaluated in a survival assay as described above. Surprisingly, and in contrast to 5-fluorouridine and 5-fluorouracil, 5-hydroxymethylcytidine and 5-hydroxymethylcytosine were shown not to be cytotoxic to U87-MG cells (FIG. 2C).

These results indicate that the 2'-deoxyribose sugar is necessary for cytotoxicity of the compounds of the present invention. In turn, this result indicates, surprisingly, that 5-formyl-2'-deoxycytidine and 5-hydroxymethyl-2'-deoxycytidine exploit a fundamentally different cellular pathway than fluropyrimidines.

Example 7: Non-Effect of Cytidine Deaminase

Mutated nucleoside and nucleotide analogues are often removed from the nucleotide pool by cytidine deaminase (CDA). CDA inactivates gemcitabine and cytosine arabinoside—two common nucleotide analogue anti-cancer agents. Anti-cancer agents that are not inactivated by CDA would be desirable. Since 5-formyl-2'-deoxycytidine and 5-hydroxymethyl-2'-deoxycytidine are cytidine derivatives, the present inventors hypothesized that cells expressing CDA would be resistant to treatment with 5-formyl-2'-deoxycytidine and 5-hydroxymethyl-2'-deoxycytidine.

Surprisingly, however, there was in fact no correlation observed between CDA expression and resistance or sensitivity to either 5-formyl-2'-deoxycytidine or 5-hydroxymethyl-2'-deoxycytidine, as shown in Table 4A. The $IC_{50}$ data in Table 4 is identical to that in Table 1. CDA expression levels in the cell lines specified were identified using the EMBL expression atlas (https://www.ebi.ac.uk/gxa/home, using the search term CDA). CDA expression is reported as RNA transcripts per million (TPM), as described in Wagner et al., (2012) Theory Biosci 131(4):281-285 and Mortazavi A et al., (2008) "Mapping and quantifying mammalian transcriptomes by RNA-Seq." Nature methods 5(7):621-8. If more than one value was reported the lowest value was used.

TABLE 4A

No correlation between level of CDA expression and sensitivity to treatment with 5-formyl-2'-deoxycytidine or 5-hydroxymethyl-2'-deoxycytidine.

| Cell Line | Disease | Germ Layer | CDA expression (TPM) | IC$_{50}$ (μM) 2d5fC | IC$_{50}$ (μM) 2d5hmC |
|---|---|---|---|---|---|
| U87-MG | Glioma, Grade IV | Ectoderm | 6 | 0.3340 | 3.027 |
| HCT-116 | Colon Carcinoma | Endoderm | 24 | > | >25.00 |
| A549 | Lung Carcinoma | Endoderm | 50 | > | >25.00 |
| 22Rv1 | Prostate Carcinoma | Endoderm | 1 | >25.00 | >25.00 |
| NCI-N87 | Gastric Carcinoma | Endoderm | 46 | 0.8057 | >25.00 |
| MIA | Pancreatic Carcinoma | Endoderm | 3 | 1.143 | >25.00 |
| A-498 | Kidney Carcinoma | Mesoderm | 29 | > | >25.00 |
| U937 | Lymophoma | Mesoderm | 146 | 0.9536 | >25.00 |
| A375 | Malignant Melanoma | Mesoderm | 0 | 3.188 | >25.00 |
| HL-60 | Acute Promyelocytic Leukemia | Mesoderm | 10 | 6.262 | >25.00 |
| SK-OV-3 | Ovarian Adenocarcinoma | Mesoderm | 295 | 9.690 | >25.00 |
| MCF-7 | Epithelial Adenocarcinoma | Mesoderm | 0 | 0.8657 | >25.00 |
| U2OS | Bone Osteoscarcoma | Mesoderm | 13.0 | 8.69 | >25.00 |
| HeLa | Cervical Adenocarcinoma | Mesoderm | 42 | 0.76 | >25.00 |
| HAP1 | Chronic Myelogenous Leukemia (CML) | Mesoderm | N.A. | >25.00 | 6.53 |
| V79 | Chinese Hamster Ovary | Mesoderm | N.A. | >25.00 | >25.00 |
| H1437 | Lung (metastatic non-small cell adenocarcinoma) | Endoderm | 49 | 5.65 | n.d. |
| H1573 | Lung (metastatic adenocarcinoma) | Endoderm | 67 | 7.72 | n.d. |
| MDA-MB-231 | breast adenocarcinoma, | Endoderm | 153.0 | — | — |
| HOP-92 | non-small cell lung carcinoma | Endoderm | 321.0 | — | — |
| Capan-2 | pancreatic ductal adenocarcinoma | Endoderm | 248.0 | — | — |

A linear correlation between cytotoxicity and drug exposure showed a poor fit (Linear Model for 2d5fc, $R_z$=0.00173; Linear Model for 2d5hmC, $R_z$=0.02262). The data, taken together with the data from EMBL, suggested that CDA expression is not relevant to 5-formyl-2'-deoxycytidine or 5-hydroxymethyl-2'-deoxycytidine sensitivity or resistance.

Additionally, the CDA expression level (TPM) of various glioma cell lines was determined, and is shown in Table 4B. CDA expression levels in the cell lines specified were identified using the Cancer Cell Line Encyclopedia (https://portals.broadinstitute.org/ccle), which is described in Barretina J et al. (2012) The Cancer Cell Line Encyclopedia enables predictive modelling of anticancer drug s8 CDA expression is reported as RNA transcripts per million (TPM), as described in Wagner et al., (2012) Theory Biosci 131(4):281-285. If more than one value was reported the highest value was used.

TABLE 4B

Level of CDA expression in various glioma cell lines.

| Glioma Cell Line | CDA expression (TPM) |
|---|---|
| 42-MG-BA | 1.0 |
| 8-MG-BA | 3.0 |
| A172 | 2.0 |
| AM-38 | 7.0 |
| CAS-1 | 0.2 |
| DBTRG-05MG | 0.7 |
| DK-MG | 0.1 |
| GAMG | 41.0 |
| GB-1 | 0.5 |
| GMS-10 | 24.0 |
| GOS-3 | 0.5 |
| KALS-1 | 24.0 |
| KNS-42 | 0.4 |
| KNS-60 | 30.0 |
| KNS-81 | 0.6 |
| KS-1 | 7.0 |
| LN-18 | 11.0 |
| LN-229 | 0.3 |
| M059K | 8.0 |
| SF-295 | 3.0 |
| SF126 | 16.0 |
| SNB75 | 0.6 |
| SNU-1105 | 7.0 |
| SNU-201 | 0.3 |
| SNU-466 | 0.1 |
| SNU-489 | 3.0 |
| SNU-626 | 0.2 |
| T98G | 3.0 |
| U-87 MG | 6.0 |
| YH-13 | 4.0 |
| YKG1 | 0.2 |

Example 8: Non-Mutagenic Effect

A current frontline treatment for Glibolastoma Multiforme—Temozolomide—is potent mutagen. In fact, temozolomide exerts its cancer chemotherapeutic activity is by mutating tumour cell so severely that the tumour cells are killed. Temozolomide works by alkalyting DNA causing mutations. The expression of MGMT—a protein responsible for removing alkalyated DNA damage—makes glioblastoma cells almost completely resistant to the cytotoxic effects of Temozolomide.

Figure 3:
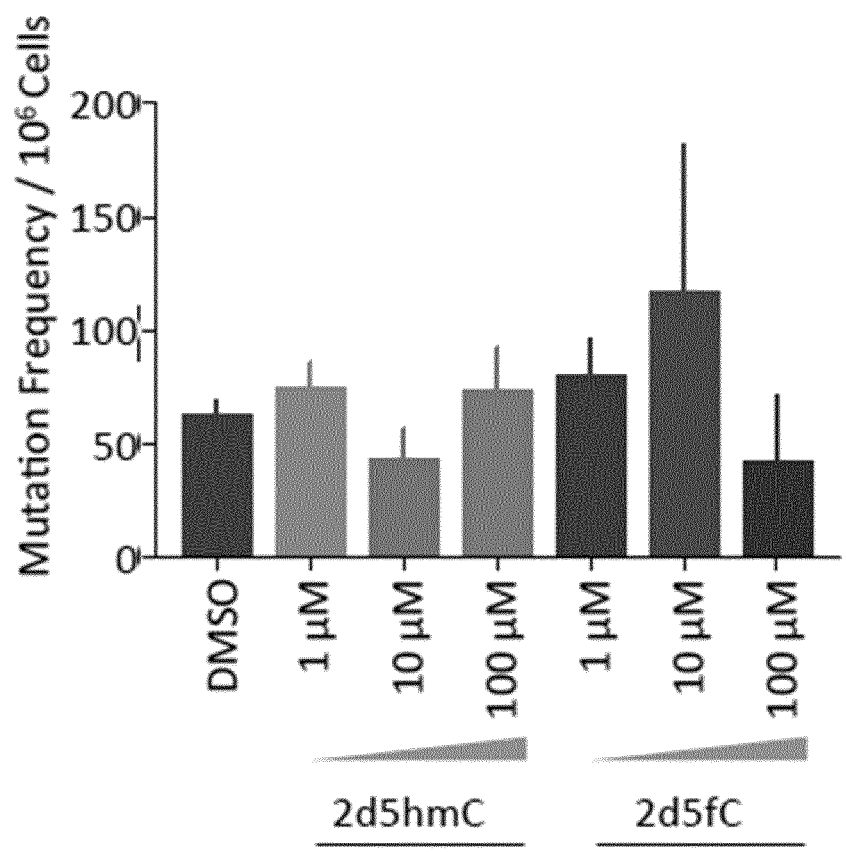
FIG. 3 shows quantification of mutations in the Hypoxanthine-guanine phosphoribosyltransferase (HPRT) gene induced by 5-formyl-2'-deoxycytidine and 5-hydroxymethyl-2'-deoxycytidine in mammalian cells. 5-formyl-2'-deoxycytidine and 5-hydroxymethyl-2'-deoxycytidine are shown not to be mutagenic.

Therefore, the present inventors investigated whether 5-formyl-2'-deoxycytidine and 5-hydroxymethyl-2'-deoxycytidine had a similar mechanism of action. The mutagenicity of these compounds was evaluated in an Hypoxanthine-guanine phosphoribosyltransferase (HPRT) assay as described above (Materials and Methods). As shown in the HPRT assay neither 5-hydroxymethyl-2'-deoxycytidine nor 5-formyl-2'-deoxycytidine were genotoxic to mammalian cells at any concentration evaluated (FIG. 3). These results indicate that the 5-hydroxymethyl-2'-deoxycytidine and 5-formyl-2'-deoxycytidine are not mutagens, i.e. that their cytotoxic effects are not due to mutagenic activity.

Example 9: Cytotoxicity of Other Compounds Vs. HeLa Cells

HeLa cells were treated with either 5-formyl-2'-deoxycytidine, 5-formylcytidine or 5-chloro-2'-deoxycytidine. After three days of treatment with these compounds at a concentration of 100, 25, 6.25, 1.56, 0.39, 0.1, 0.02, or 0.006 µM, cell survival was assessed by MTT assay as described above (Materials and Methods).

Figure 4:
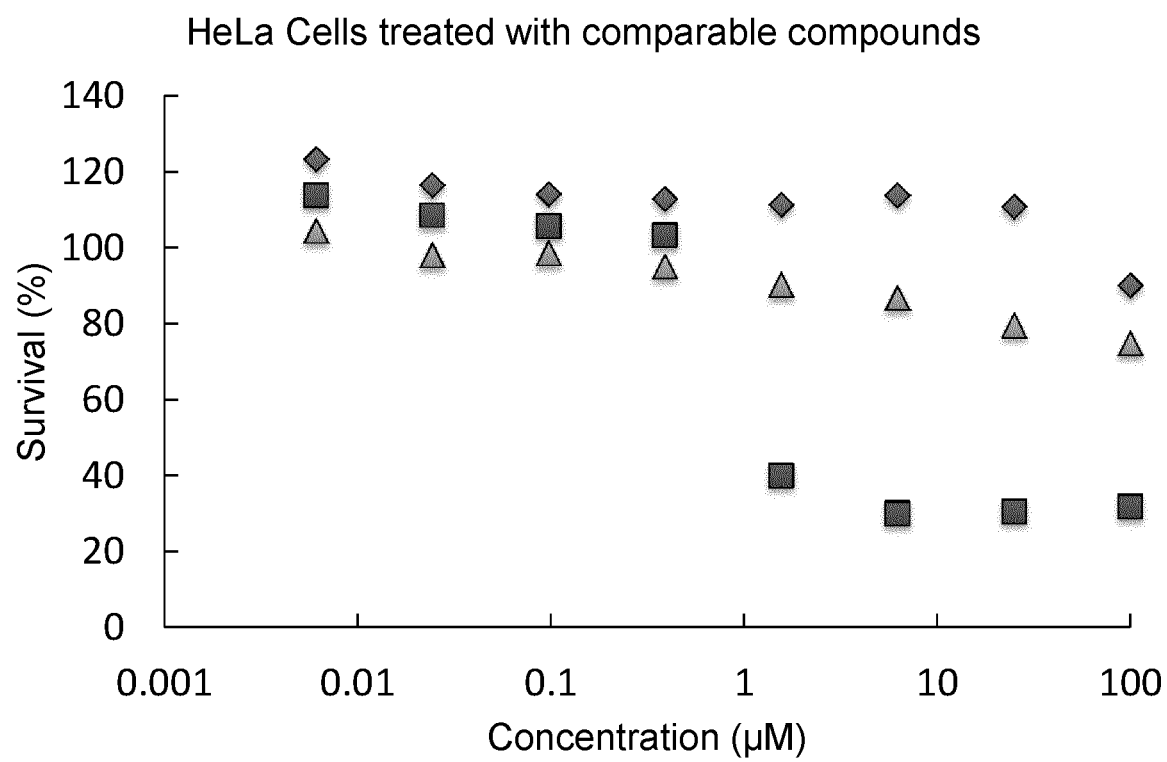
Figure 4 shows the level of cytotoxicity (% survival) of 5-formyl-2'-deoxycytidine, 5-formylcytidine and 5-chloro-2'-deoxycytidine against HeLa cells after three days of treatment.
Figure 4:
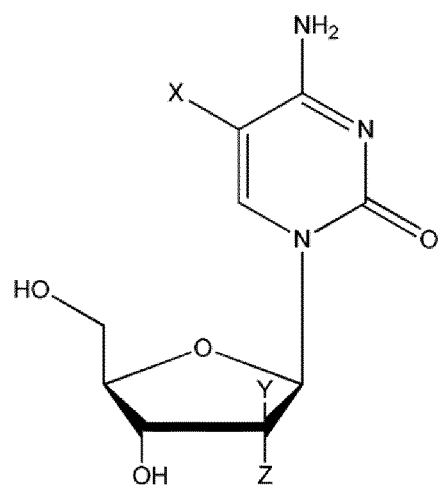

As shown in FIG. 4. A markedly greater cytotoxic effect is observed following treatment with 5-formyl-2'-deoxycytidine than following treatment with either 5-formylcytidine or 5-chloro-2'-deoxycytidine.

Example 10: Cytotoxicity of Other Compounds Vs. Glioma Cells

U87-MG cells (Glioma, Grade IV) were treated with either 5-formyl-2'-deoxycytidine, 5-hydroxymethyl-2'-deoxycytidine, 5-carboxy-2'-deoxycytidine, Temozolomide, 5-flurouracil, 5-bromo-2'-deoxycytidine, 5-iodo-2'-deoxycytidineor 5-chloro-2'-deoxycytidine at a concentration of 100, 25, 6.25, 1.56, 0.39, 0.1, 0.02, or 0.006 µM. After three days of treatment with these compounds, cell survival was assessed by MTT assay as described above (Materials and Methods).

Cell Culture

U87-MG cell lines were grown in DMEM (Sigma, Cat.Nr. D6429) supplemented with 10% Fetal Bovine Serum. All cells were maintained in a 5% CO2, humidified, water-jacketed incubator at 37° C. Cells were passed between 70 and 90% confluence.

Survival Assay

In a 96-well plate, 4000 cells in 100 µl of corresponding medium were seeded. The following day, drugs, diluted in DMSO, were added in triplicate at a concentration of 100, 25, 6.25, 1.56, 0.39, 0.1, 0.02, or 0.006 µM. Cells were incubated with the drugs for 72 hours. Cell proliferation was assessed by MTT assay according to the manufacturer's protocol (ATCC, Cat. Nr. 30-1010K). Cell survival was normalized to the survival of cells treated with DMSO only. Experiment was performed three times, data represent mean of nine wells±SEM.

As shown in Table 5, both 5-formyl-2'-deoxycytidine and 5-hydroxymethyl-2'-deoxycytidine performed surprisingly better in terms of cytotoxicity vs. U87-MG cells than the other compounds tested, including 5-bromo-2'-deoxycytidine, 5-iodo-2'-deoxycytidine and 5-chloro-2'-deoxycytidine.

TABLE 5

Evaluation of cytotoxicity of various compounds to U87-MG cells. $IC_{50}$ is the concentration at which half of the cells are killed by the relevant compound.
Cell Line: U87-MG

| Compound Tested | $IC_{50}$ (µM) |
| --- | --- |
| 5-formyl-2'-deoxycytidine | 0.3340 |
| 5-hydroxymethyl-2'-deoxycytidine | 3.027 |
| 5-carboxy-2'-deoxycytidine | >25.00 |
| Temozolomide | >25.00 |
| 5-flurouracil | >25.00 |
| 5-bromo-2'-deoxycytidine | >25.00 |
| 5-chloro-2'-deoxycytidine | >25.00 |
| 5-iodo-2'-deoxycytidine | >25.00 |

Figure 5:
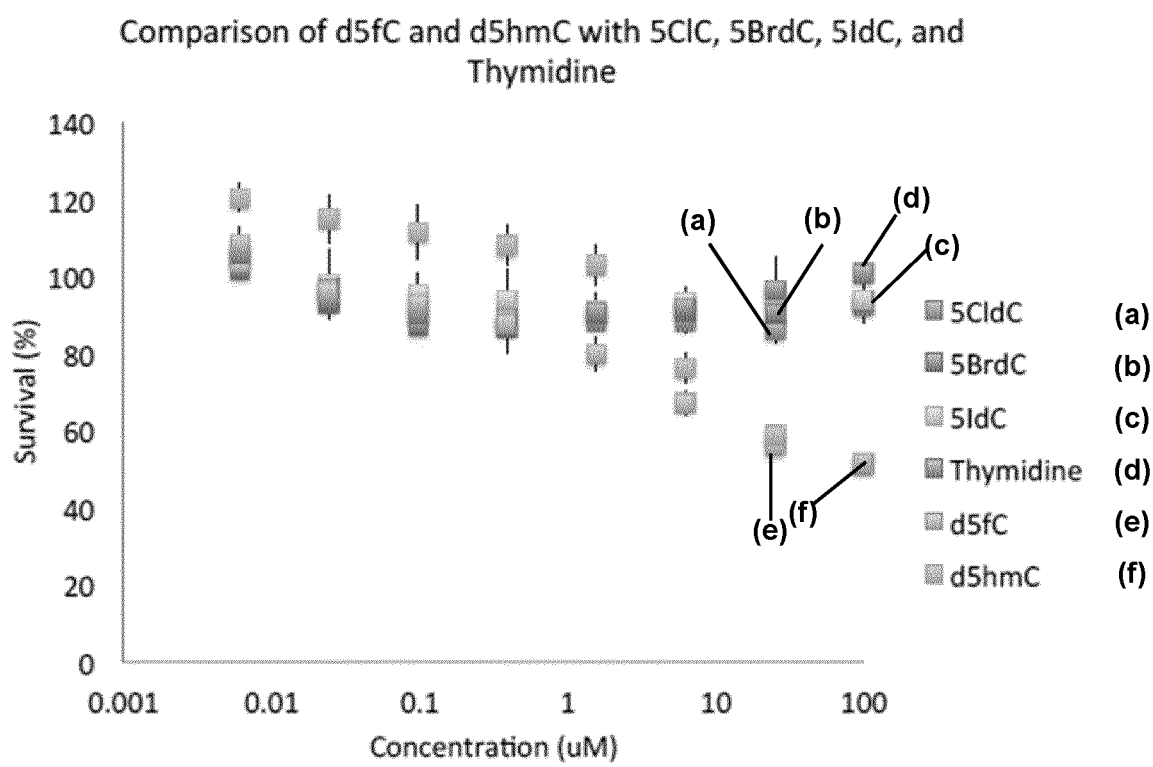
FIG. 5 shows the level of cytotoxicity (% survival) of 5-formyl-2'-deoxycytidine (d5fC), 5-hydroxymethyl-2'-deoxycytidine (d5hmC), 5-chloro-2'-deoxycytidine (5CldC), 5-bromo-2'-deoxycytidine (5BrdC), 5-Iodo-2'deoxycytidine (5IdC), and Thymidine vs. U87-MG cells.

Additionally, U87-MG cells were treated with 5-formyl-2'-deoxycytidine (d5fC), 5-hydroxymethyl-2'-deoxycytidine (d5hmC), 5-chloro-2'-deoxycytidine (5CldC), 5-bromo-2'-deoxycytidine (5BrdC), 5-Iodo-2'deoxycytidine (5IdC), and Thymidine. The results are shown in FIG. 5. d5hmC and d5fC are markedly more cytotoxic than 5CldC, 5BrdC, dIdC, and thymidine to glioma cells.

In a 96-well plate, 4000 cells in 100 µl of corresponding medium were seeded. The following day, drugs, diluted in DMSO, were added in triplicate at a concentration of 100, 25, 6.25, 1.56, 0.39, 0.1, 0.02, or 0.006 µM. Cells were incubated with the drugs for 72 hours. Cell proliferation was assessed by MTT assay according to the manufacturer's protocol (ATCC, Cat. Nr. 30-1010K). Cell survival was normalized to the survival of cells treated with DMSO only. Experiment was performed three times, data represent mean±SD.

Example 11: Effect not Mediated Via Thymidine Synthase

Cell Culture

U87-MG cell lines were grown in DMEM (Sigma, Cat.Nr. D6429) supplemented with 10% Fetal Bovine Serum. All cells were maintained in a 5% CO2, humidified, water-jacketed incubator at 37° C. Cells were passed between 70 and 90% confluence.

Survival Assay

In a 96-well plate, 4000 cells in 100 µl of corresponding medium were seeded. The following day, drugs, diluted in DMSO, were added in 8 concentrations in triplicate. Drugs were added as a 4-fold dilution series starting from 100 µM. Cells were incubated with the drugs for 72 hours. Cell proliferation was assessed by MTT assay according to the manufacturer's protocol (ATCC, Cat. Nr. 30-1010K). Cell survival was normalized to the survival of cells treated with DMSO only. Experiment was performed three times, data represent mean of three wells±SD.

The results are shown in FIG. 6. Cytotoxicity by 5-formyl-2'-deoxycytidine and 5-hydroxymethyl-2'-deoxycytidine is not rescued by the addition of thymidine in U87-MG cells. This result indicates that 5-formyl-2'-deoxycytidine and 5-hydroxymethyl-2'-deoxycytidine do not act by inhibiting thymidine synthase.

Example 12: Combined Therapy with Temozolomide

Cell Culture

Glioblastoma multiforme cell lines (U87-MG) were grown in DMEM (Sigma, Cat.Nr. D6429) supplemented with 10% Fetal Bovine Serum. All cells were maintained in a 5% CO2, humidified, water-jacketed incubator at 37° C. Cells were passed between 70 and 90% confluence.

Survival Assay

In a 96-well plate, 4000 cells in 100 µl of corresponding medium were seeded. The following day, drugs, diluted in DMSO, were added in 8 concentrations in triplicate. Drugs were added as a 4-fold dilution series starting from 100 µM. Cells were incubated with the drugs for 72 hours. Cell proliferation was assessed by MTT assay according to the manufacturer's protocol (ATCC, Cat. Nr. 30-1010K). Cell survival was normalized to the survival of cells treated with DMSO only. Experiment was performed three times, data represent mean of these experiments.

As shown in FIG. 7, a human glioblastoma multiforme cell line that is resistant to temozolomide was treated with temozolomide alone, 5-formyl-2'-deoxycytidine (d5fC) or a combination of d5fC and temozolomide. The combination of temozolomide and d5fC is more effective at treating human glioblastoma multiforme than either chemical alone.

As shown in FIG. 8, a human glioblastoma multiforme cell line that is resistant to temozolomide was treated with temozolomide alone, 5-hydroxymethyl-2'-deoxycytidine (d5hmC) or a combination of d5hmC and temozolomide. The combination of temozolomide and d5hmC is more effective at treating human glioblastoma multiforme than either chemical alone.

Thus, 5-hydroxymethyl-2'-deoxycytidine and 5-formyl-2'-deoxycytidine act synergistically with temozolomide.

Example 13: Uridine Analogues

The cytotoxic effects of 5-methoxymethyl-2'-deoxyuridine and 5-acetoxymethyl-2'-deoxyuridine were evaluated.

Cell Culture

U87-MG cell lines were grown in DMEM (Sigma, Cat.Nr. D6429) supplemented with 10% Fetal Bovine Serum. All cells were maintained in a 5% CO2, humidified, water-jacketed incubator at 37° C. Cells were passed between 70 and 90% confluence.

Survival Assay

In a 96-well plate, 4000 cells in 100 µl of corresponding medium were seeded. The following day, drugs, diluted in DMSO, were added in 8 concentrations in triplicate. Drugs were added as a 4-fold dilution series starting from 100 µM. Cells were incubated with the drugs for 72 hours. Cell proliferation was assessed by MTT assay according to the manufacturer's protocol (ATCC, Cat. Nr. 30-1010K). Cell survival was normalized to the survival of cells treated with DMSO only. Experiment was performed three times, data represent mean of nine wells±SEM.

As shown in FIG. 9, the U87-MG, glioblastoma multiforme, cell line is unable to survive a treatment with increasing concentrations of 5-methoxymethyl-2-deoxyuridine or 5-acetoxymethyl-2'-deoxyuridine. Therefore, 5-methoxymethyl-2-deoxyuridine and 5-acetoxymethyl-2'-deoxyuridine are effective anti-cancer agents, particularly against glioblastoma multiforme.

Example 14: Cytotoxicity of 5-Formyl-2'-Deoxycytidine-5'-Triphosphate (HeLa)

Cell Culture

HeLa cell lines were grown in DMEM (Sigma, Cat.Nr. D6429) supplemented with 10% Fetal Bovine Serum. All cells were maintained in a 5% $CO_2$, humidified, water-jacketed incubator at 37° C. Cells were passed between 70 and 90% confluence.

Survival Assay

In a 96-well plate, 4000 cells in 100 µl of corresponding medium were seeded. The following day, drugs, diluted in DMSO, were added in 8 concentrations in triplicate. Drugs were added as a 4-fold dilution series starting from 100 µM. Cells were incubated with the drugs for 72 hours. Cell proliferation was assessed by MTT assay according to the manufacturer's protocol (ATCC, Cat. Nr. 30-1010K). Cell survival was normalized to the survival of cells treated with DMSO only. Experiment was performed three times, data represent mean of nine wells±SEM.

As shown in FIG. 10A, HeLa cervical carcinoma cells are unable to survive a treatment with increasing concentrations of 5-formyl-2'-deoxycytidine-5'-triphosphate. This demonstrates 5-formyl-2'-deoxycytidine-5'-triphosphate's utility in the treatment of human cancers, for instance cervical carcinoma.

Example 15: Cytotoxicity of 5-Formyl-2'-Deoxycytidine-5'-Triphosphate and 5-Hydroxymethyl-2'-Deoxycytidine-5'-Triphosphate (Glioma)

U87-MG cells (Glioma, Grade IV) were treated with either 5-formyl-2'-deoxycytidine-5'-triphosphate or 5-hydroxymethyl-2'-deoxycytidine-5'-triphosphate at a concentration of 100, 25, 6.25, 1.56, 0.39, 0.1, 0.02, or 0.006 µM. After three days of treatment with these compounds, cell survival was assessed by MTT assay as described above (Materials and Methods).

Cell Culture

U87-MG cell lines were grown in DMEM (Sigma, Cat.Nr. D6429) supplemented with 10% Fetal Bovine Serum. All cells were maintained in a 5% CO2, humidified, water-jacketed incubator at 37° C. Cells were passed between 70 and 90% confluence.

Survival Assay

In a 96-well plate, 4000 cells in 100 µl of corresponding medium were seeded. The following day, drugs, diluted in DMSO, were added in triplicate at a concentration of 100, 25, 6.25, 1.56, 0.39, 0.1, 0.02, or 0.006 µM. Cells were incubated with the drugs for 72 hours. Cell proliferation was assessed by MTT assay according to the manufacturer's protocol (ATCC, Cat. Nr. 30-1010K). Cell survival was normalized to the survival of cells treated with DMSO only. Experiment was performed three times, data represent mean of at least 3 wells±SD.

As shown in FIG. 10B, both 5-formyl-2'-deoxycytidine-5'-triphosphate and 5-hydroxymethyl-2'-deoxycytidine-5'-triphosphate were cytotoxic to U87-MG, glioma, cells.

Example 16: CDA Expression

The linear and logarithm base 2 transformed CDA expression level of various glioma cell lines was determined. CDA expression levels in the cell lines specified were identified using the GENEVESTIGATOR® database (https://genevestigator.com/gv/), by searching for CDA, organism: homosapiens, platform: Affymetrix Human Genome U133 2.0 Array. The results are shown in FIGS. 11 to 13 and Table 6.

FIG. 11 shows the CDA normalized Log 2 CDA expression levels determined for various cancers. FIG. 12 shows the linear CDA expression levels determined for various cancers. FIGS. 13A and 13B show the CDA normalized Log 2 expression levels in various human brain tumours. FIGS. 14A and 14B show the linear CDA expression levels in various human brain tumours.

Table 6 below shows the CDA expression levels of various cell lines and the $IC_{50}$ values for 2d5hmC and/or 2d5fc in those cell lines. $IC_{50}$ values were obtained as described above (Materials and Methods and Example 1).

Together these results demonstrate that many cancers, including all tested cancers of the central nervous system, do not over-express CDA; rather they express low levels of CDA. The results also demonstrate that there is no correlation between CDA expression and sensitivity to either 5-formyl-2'-deoxycytidine or 5-hydroxymethyl-2'-deoxycytidine

TABLE 6

CDA expression levels (Log2 normalized values) and 2d5hmC and/or 2d5fc $IC_{50}$ values in various cell lines.

| Cell Line | IC50 2d5hmC | IC50 2d5fC | CDA Mean Log2 | CDA Expression SD Log2 | CDA Expression Median Log2 |
|---|---|---|---|---|---|
| U87-MG | 3.027 | 0.334 | 9.84 | 0.42 | 9.94 |
| HCT-116 | 25 | 25 | 11.11 | 0.62 | 10.93 |
| A549 | 25 | 25 | 12 | 1.01 | 11.93 |
| 22Rv1 | 25 | 25 | 8.92 | 0.62 | 9.05 |
| NCI-N87 | 25 | 0.8057 | 11.6 | 0.56 | 11.37 |
| MIA PaCa-2 | 25 | 1.143 | 9.68 | 0.49 | 9.79 |
| A-498 | 25 | 25 | 10.52 | 1.06 | 10.32 |
| U937 | 25 | 0.9536 | 13.82 | 0.45 | 13.89 |
| A375 | 25 | 3.188 | 9.36 | 0.62 | 9.56 |
| HL-60 | 25 | 6.262 | 10.36 | 0.96 | 10.12 |
| SK-OV-3 | 25 | 9.69 | 13.35 | 1.59 | 14.07 |
| MCF-7 | 25 | 0.8657 | 9.26 | 0.39 | 9.2 |
| U2OS | 25 | 8.69 | 10.14 | | 10.14 |
| HeLa | 25 | 0.76 | 13.15 | 0.92 | 13.33 |
| HAP1 | 6.53 | 25 | None | | |
| HEK293 | 25 | 25 | 9.59 | 0.4 | 9.53 |
| ARPE19 | 25 | 25 | 9.99 | 0.7 | 9.94 |
| MRC5 | 25 | 25 | 9.87 | 0.29 | 9.82 |
| H1437 | — | 5.65 | 13.02 | 1.12 | 12.44 |
| H1573 | — | 7.72 | 13.63 | 0.18 | 13.67 |

Table 7 below shows the linear CDA expression levels of various cell lines and the $IC_{50}$ values for 2d5hmC and/or 2d5fc in those cell lines. $IC_{50}$ values were obtained as described above (Materials and Methods and Example 1).

TABLE 7

Linear CDA expression levels and 2d5hmC and/or 2d5fc $IC_{50}$ values in various cell lines.

| Cell Line | IC50 2d5hmC | IC50 2d5fC | CDA Linear Mean | CDA Linear SD | CDA Linear Median |
|---|---|---|---|---|---|
| U87-MG | 3.027 | 0.334 | 951.65 | 276.02 | 989.44 |
| HCT-116 | 25 | 25 | 2481.67 | 1559.27 | 1949.23 |
| A549 | 25 | 25 | 5490.76 | 5549.26 | 3904.87 |
| 22Rv1 | 25 | 25 | 519.39 | 225.08 | 527.89 |
| NCI-N87 | 25 | 0.8057 | 3327.03 | 1464.72 | 2654.16 |
| MIA PaCa-2 | 25 | 1.143 | 860.01 | 261.17 | 881.38 |
| A-498 | 25 | 25 | 1874.54 | 1443.37 | 1301.02 |
| U937 | 25 | 0.9536 | 15148.69 | 4611.68 | 15231.25 |
| A375 | 25 | 3.188 | 700.89 | 226.39 | 753.10 |
| HL-60 | 25 | 6.262 | 1787.26 | 2129.78 | 1112.79 |
| SK-OV-3 | 25 | 9.69 | 15500.02 | 11439.83 | 17236.82 |
| MCF-7 | 25 | 0.8657 | 635.57 | 182.06 | 588.96 |
| U2OS | 25 | 8.69 | 1130.20 | N/A | 1130.20 |
| HeLa | 25 | 0.76 | 10915.38 | 6549.95 | 10272.63 |
| HAP1 | 6.53 | 25 | *** | *** | *** |
| HEK293 | 25 | 25 | 800.57 | 225.25 | 738.45 |
| ARPE19 | 25 | 25 | 1133.42 | 515.09 | 981.92 |
| MRC5 | 25 | 25 | 950.82 | 212.00 | 901.07 |
| H1437 | — | 5.65 | 11861.95 | 14192.00 | 5568.28 |
| H1573 | — | 7.72 | 12779.53 | 1515.78 | 13045.67 |

Example 17: Blood-Brain Barrier Permeability

Blood brain barrier permeability was measured using a Parallel Artificial Membrane Permeability Assay Kit (PAMPA) from BioAssay systems. The manufacturer's instructions were followed to determine permeability.

Manufacturer's instructions: 1. In separate centrifuge tubes, prepare 500 µL of 500 µM Test Compound: mix 25 µL 10 mM Test Compound in DMSO+475 µL PBS. If using the Permeability Controls, dilute them to 500 µM as well: mix 25 µL Permeability Control+475 µL PBS. 2. In separate tubes, prepare 200 µM Equilibrium Standards for each test compound and control: mix 80 µL of 500 µM Test Compound or Control with 120 µL PBS. If the compound is able to permeabilize the membrane and fully reach equilibrium, 200 µM will be the final concentration of solution in the Donor and Acceptor wells. Next, in a separate tube, mix 5 µL DMSO+245 µL PBS to prepare the Blank Control. Set aside the Equilibrium Standards and Blank Control for analysis the next day. 3. Add 300 µL PBS to wells in the acceptor plate. 4. With the donor plate still in its tray, add 5 µL 4% Lecithin in Dodecane directly to the well membranes of the donor plate. Be careful not to puncture the membranes with the pipette tip. 5. Add 200 µL of each 500 µM Test Compound and 500 µM Permeability Controls to duplicate wells of the donor plate. Note: we recommend running all experimental variables in at least duplicate5. Carefully place the donor plate into the acceptor plate wells. Incubate at RT or 37° C. for 18 hours or the desired incubation time period (e.g. 16-24 hours) 6. Carefully remove donor plate and collect the liquid in acceptor plate wells for analysis. This will be referred to as Acceptor Solution 7. Add 100 μL of Acceptor Solution and Equilibrium Standards for each Test Compound and Permeability Control. Also add 100 μL Blank Control to wells of UV plate (Cat # P96UV). 8. Read Absorbance spectrum from 200 nm to 500 nm in 10 nm intervals to determine peak absorbance of test compounds. The Blank Control is to confirm peaks are due to the test compound and not the DMSO in the solution. Peak absorbance for High Permeability, Medium Permeability, and Low Permeability Controls are 280 nm, 270 nm, and 270 nm respectively.

As shown in FIG. 15, 2d5hmC and 2d5fC pass the blood brain barrier.

The invention claimed is:

1. A method of treating or preventing a cancer of the central nervous system in a subject in need thereof, which comprises administering to the subject a compound of Formula (IIa):

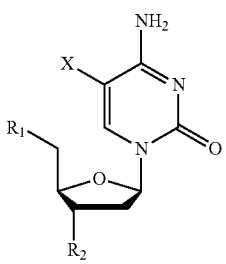

Formula (IIa)

or a stereoisomer, solvate, tautomer or pharmaceutically acceptable salt thereof, wherein:
X is —(CH$_2$)$_n$—X';
n is an integer having a value of from 0 to 6;
X' is —CHO, —OH, —OR, or —OC(=O)R;
R is methyl;
R$_1$ is —OH or —O(P(=O)(OH)O)$_m$H, where m is an integer having a value of from 1 to 3; and
R$_2$ is —OH.

2. The method of claim 1, wherein the compound is a compound of Formula (IIIa) or (IIIc), or a stereoisomer, solvate, tautomer, or pharmaceutically acceptable salt thereof:

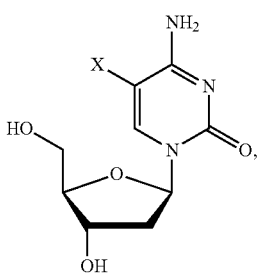

Formula (IIIa)

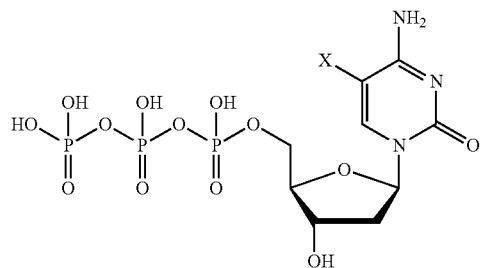

Formula (IIIc)

wherein X is as defined in claim 1.

3. The method of claim 1, wherein X is:
a) —CHO or —CH$_2$OH; or
b) —CH$_2$OCH$_3$ or —CH$_2$OC(=O)CH$_3$.

4. The method of claim 1, wherein X is —CHO or —CH$_2$OH.

5. The method of claim 1, wherein X is CH$_2$OH.

6. The method of claim 1, wherein the compound is 5-formyl-2'-deoxycytidine, 5-hydroxymethyl-2'-deoxycytidine, 5-formyl-2'-deoxycytidine-5'-triphosphate or 5-hydroxymethyl-2'-deoxycytidine-5'-triphosphate, or a stereoisomer, solvate, tautomer, or pharmaceutically acceptable salt thereof.

7. The method of claim 6, wherein the compound is 5-formyl-2'-deoxycytidine or 5-hydroxymethyl-2'-deoxycytidine, or a stereoisomer, solvate, tautomer, or pharmaceutically acceptable salt thereof.

8. The method of claim 7, wherein the compound is 5-hydroxymethyl-2'-deoxycytidine or a stereoisomer, solvate, tautomer, or pharmaceutically acceptable salt thereof.

9. The method of claim 1, wherein the cancer is a brain cancer.

10. The method of claim 1, wherein the cancer is a glioma.

11. The method of claim 1, wherein the cancer is resistant to treatment with gemcitabine, cytarabine, temozolomide, or 5-fluorouracil.

12. The method of claim 1, wherein the compound is administered at a dose of between 10 mg/kg and 405 mg/kg.

13. The method of claim 1, further comprising administering an additional anticancer agent.

14. The method of claim 2, wherein the compound is a compound of Formula (IIIa) or Formula (IIIc).

15. The method of claim 10, wherein the cancer is a glioblastoma.

16. The method of claim 13, wherein the additional anticancer agent is selected from the group consisting of: gemcitabine, cytarabine, temozolomide, 5-fluorouracil, and carmustine.

* * * * *